United States Patent
Culiat

(10) Patent No.: US 12,281,144 B2
(45) Date of Patent: *Apr. 22, 2025

(54) METHODS AND COMPOSITIONS FOR REGENERATING TISSUES

(71) Applicant: NELLONE THERAPEUTICS, INC., Knoxville, TN (US)

(72) Inventor: Cymbeline T. Culiat, Oak Ridge, TN (US)

(73) Assignee: NELLONE THERAPEUTICS, INC., Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/391,146

(22) Filed: Dec. 20, 2023

(65) Prior Publication Data

US 2024/0301020 A1    Sep. 12, 2024

Related U.S. Application Data

(60) Continuation of application No. 17/333,406, filed on May 28, 2021, now Pat. No. 11,891,424, which is a division of application No. 16/813,376, filed on Mar. 9, 2020, now Pat. No. 11,034,741, which is a division of application No. 15/690,093, filed on Aug. 29, 2017, now Pat. No. 10,752,663.

(60) Provisional application No. 62/380,920, filed on Aug. 29, 2016.

(51) Int. Cl.
*A61K 38/17* (2006.01)
*C07K 14/47* (2006.01)

(52) U.S. Cl.
CPC ...... *C07K 14/4705* (2013.01); *A61K 38/1709* (2013.01); *C07K 14/47* (2013.01)

(58) Field of Classification Search
CPC .... A61K 38/17; A61K 38/1709; C07K 14/47; C07K 14/4705
See application file for complete search history.

(56) References Cited

U.S. PATENT DOCUMENTS

| | | | |
|---|---|---|---|
| 7,052,856 | B2 | 5/2006 | Ting |
| 7,687,462 | B2 | 3/2010 | Ting et al. |
| 7,884,066 | B2 | 2/2011 | Ting |
| 7,910,542 | B2 | 3/2011 | Culiat |
| 8,722,625 | B2 | 5/2014 | Culiat |
| 8,877,176 | B2 | 11/2014 | Culiat |
| 9,920,104 | B2 | 3/2018 | Culiat |
| 2006/0025367 | A1 | 2/2006 | Simari |
| 2006/0053503 | A1 | 3/2006 | Culiat |
| 2006/0111313 | A1 | 3/2006 | Ting et al. |
| 2006/0228392 | A1 | 10/2006 | Ting |
| 2006/0292670 | A1 | 12/2006 | Ting et al. |
| 2007/0128697 | A1 | 6/2007 | Ting et al. |
| 2007/0134291 | A1 | 6/2007 | Ting et al. |
| 2009/0087415 | A1 | 4/2009 | Culiat |
| 2011/0236325 | A1 | 9/2011 | Mitchell et al. |
| 2014/0205577 | A1 | 7/2014 | Culiat |
| 2015/0037294 | A1 | 2/2015 | Culiat |
| 2018/0057550 | A1 | 3/2018 | Culiat |
| 2020/0199184 | A1 | 6/2020 | Culiat |

FOREIGN PATENT DOCUMENTS

| | | |
|---|---|---|
| WO | WO 2002/100426 | 12/2002 |
| WO | WO 2004/024893 | 3/2004 |
| WO | WO 2004/072100 | 8/2004 |
| WO | WO 2006/089023 | 8/2006 |
| WO | WO 2008/073631 | 6/2008 |
| WO | WO 2008/109274 | 9/2008 |
| WO | WO 2009/042859 | 4/2009 |
| WO | WO 2009/045800 | 4/2009 |
| WO | WO 2011/091244 | 7/2011 |

OTHER PUBLICATIONS

Aghaloo et al., "A Study of the Role of Nell-1 Gene Modified Goat Bone Marrow Stromal Cells in Promoting New Bone Formation," The American Society of Gene Therapy, 2007, 15(10):1872-1880.
Aghaloo et al., "Nell-1-Induced Bone Regeneration in Calvarial Defects," Am J Pathol, 2006, 169(3):903-915.
Askarinam et al., "Human Perivascular Stem Cells Show Enhanced Osteogenesis and Vasculogenesis with Nel-Like Molecule 1 Protein," 2013, Tissue Engineering: Part A, 19(11-12):1386-1397.
Bareggi et al., "Protein Kinase C (PKC) Isoenzymes Exhibit Specific Expression in the Vertebral Column of Human Fetuses," J Biol Res, 1995, LXXI:83-91.
Bassetto et al., "Regenerative Medicine for Tendon Regeneration and Repair: The Role of Bioscaffolds and Mechanical Loading," 2011, Biomaterials Science and Engineering, Ch. 18, Ed. R. Pignatello, InTech, pp. 369-386.
Bi et al., "Identification of tendon stem/progenitor cells and the role of the extracellular matrix in their niche," Nov. 2007, Nature Medicine, 13:1219-1227.
Briggs, "Tackling Tendon and Ligament Injuries," Jun. 3, 2011, The Horse, 7 pp.
Caudill, "Stem Cell Therapy," The American Quarter Horse Racing Journal, www.americashorsedaily.com, Oct. 15, 2015, 6 pp.
Connizzo et al., "Regulatory Role of Collagen V in Establishing Mechanical Properties of Tendons and Ligaments is Tissue Dependent," Jun. 2015, J Orthopaedic Research, 33:882-888.
Cowan et al., "Nell-1 induced bone formation within the distracted intermaxillary suture," Bone, 2006, 38(1):48-58.
Cowan et al., "Synergistic Effects of Nell-1 and BMP-2 on the Osteogenic Differentiation of Myoblasts," J Bone Mineral Res, Nov. 6, 2007, 22:918-930.

(Continued)

*Primary Examiner* — Xiaozhen Xie
(74) *Attorney, Agent, or Firm* — Womble Bond Dickinson (US) LLP

(57) ABSTRACT

Provided are methods for promoting the healing of injuries to tendons and ligaments by administering a NELL1 protein or a nucleic acid encoding a NELL1 protein to a subject in need thereof. Also provided are NELL1 compositions and methods for promoting tissue regeneration, promoting the healing of wounds, and enhancing fibroblast migration, proliferation, or both migration and proliferation.

24 Claims, 10 Drawing Sheets

Specification includes a Sequence Listing.

(56) References Cited

OTHER PUBLICATIONS

Culiat et al., "Nell1: A Candidate Gene for ENU-Induced Recessive Lethal Mutaitons at the 17R6 Locus and Potential Mouse Models for Human Neonatal Unilateral Coronal Synostosis (UCS)," International Mammalian Genome Society, 15th International Mouse Genome Conference, 2001.

Culiat et al., "Nell1: A Candidate Gene for ENU-Induced Recessive Lethal Mutations at the 17R6 Locus and Potential Mouse Models for Human Neonatal Unilateral Coronal Synostosis (UCS)," Jan. 27-31, 2002, Abstract.

Davis et al., "MMP inhibition as a potential method to augment the healing of skeletal muscle and tendon extracellular matrix," 2013, J Appl Physiol, 115:884-891.

Desai et al., "Characterization of Mouse Nell1: A gene coding for a novel PKC-binding protein," Women in Science Meeting, ORNL, Oak Ridge, TN, May 1, 2006, Abstract.

Desai et al., "Nell1, A gene coding for a novel PKC-binding protein is a candidate for late-gestation recessive lethal mutations at the 17R6 locus," 16th International Mouse Genome Conference, San Antonio, TX, 17-21 Nov. 1, 2002, Abstract.

Desai et al., "Nell1-deficient mice have reduced expression of extracellular matrix proteins causing cranial and vertebral defects," Hum Mol Genet, 2006, 15(8):1329-1341.

Diwan et al., "Current Concepts in Interverterbral Disk Restoration," Orthopedic Clinics of North America, Jul. 2000, 31(3):453-464.

Ekser et al., "Clinical xenotransplantation: the next medical revolution? ," Lancet, 2012, 379:672-683.

Endo et al., "High-throughput, genome-scale protein production method based on the wheat germ cell-free expression system," 2003, Biotechnol. Adv. 21(8):695-713.

Estrada et al., "Comparison of healing in forelimb and hindlimb surgically induced core lesions of the equine superficial digital flexor tendon," 2014, Vet Comp Orthop Traumatol, 27(05):358-365.

Fortier et al., "Regenerative Medicine for Tendinous and Ligamentous Injuries of Sport Horses," 2008, Vet Clin Equine, 24:191-201.

Franke et al., "Systematic Association Mapping Identifies NELL1 as a Novel IBD Disease Gene," PLoS One, Aug. 2007, 8:e691, 13 pp.

Gelfand et al., "Surrogate Endpoints for the Treatment of Venous Leg Ulcers," 2002, J Invest Dermatol, 119:1420-1425.

Godwin et al., "Implantation of bone marrow-derived mesenchymal stem cells demonstrates improved outcome in horses with overstain injury of the superficial digital flexor tendon," 2012, Equine Veterinary Journal, 44:25-32.

Gomez et al., "Effects of 3 biologic dressings on healing of cutaneous wounds on the limbs of horse," 2004, The Canadian Journal of Veterinary Research, 68:49-55.

Haider, "Bone marrow cells for cardiac regeneration and repair: current status and issues," Expert Rev Cardiovasc Ther, 2006, 4(4):557-568.

Hamilton, "Functional role of periostin in development and wound repair: implications for connective tissue disease," 2008, J Cell Commun Signal, 2:9-17.

Hasebe et al., "Efficient Production and Characterization of Recombinant Human NELL 1 Protein in Human Embryonic Kidney 293-F Cells," Mol Biotechnol, Aug. 5, 2011, 51(1):58-66.

Hasebe et al., "The C-terminal region of NELL1 mediates osteoblastic cell adhesion through integrin α3β1," FEBS Letters, 2012, 586:2500-2506.

Hentze et al., "Teratoma formation by human embryonic stem cells: Evaluation of essential parameters for future safety studies," Stem Cell Research, 2009, 2:198-210.

Ituarte et al., "Anti-inflammatory Properties of Nell-1 on Human Articular Chondrocytes In Vivo," ORS 2014 Annual Meeting, Poster No. 0362.

James et al., "A New Function of Nell-1 Protein in Repressing Adipogenic Differentiation," Biochem Biophys Res Commun, Jul. 22, 2011, 411(1):126-131.

James et al., "NELL-1 in the treatment of osteoporotic bone loss," 2015, Nature Communications, 6:7362, 45 pp, including Supplementary Materials.

James et al., "NELL-1 induces Sca-1+ mesenchymal progenitor cell expansion in models of bone maintenance and repair," JCI Insight, 2017, 2(12):e92573, 17 pp.

Jin et al., "Hypermethylation of the nel-like 1 gene is a common and early event and is associated with poor prognosis in early-stage esophageal adenocarcinoma," 2007, Oncogene, 26:6332-6340.

Juneja et al., "Defects in Tendon, Ligament, and Enthesis in Response to Genetic Alterations in Key Proteoglycans and Glycoproteins: A Review," 2013, Arthritis 2013:1-30.

Kuroda et al., "Biochemical Characterization and Expression Analysis of Neural Thrombospondin-1-like Proteins NELL1 and NELL2," Biochem Biophys Res Commun, 1999, 265:79-86.

Kuroda et al., "Involvement of Epidermal Growth Factor-Like Domain of NELL Proteins in the Novel Protein-Protein Interaction with Protein Kinase C," Biochem Biophys Res Commun, 1999, 265:752-757.

Lecker et al., "Multiple types of skeletal muscle atrophy involve a common program of changes in gene expression," 2004, The FASEB Journal, 18(1):39-51.

Lee et al., "Brief Report: Human Perivascular Stem Cells and Nel-Like Protein-1 Synergistically Enhance Spinal Fusion in Osteoporotic Rats," Stem Cells, 2015, 33:3158-3163.

Lee et al., "Effect of Nell-1 Delivery on Chondrocyte Proliferation and Cartilaginous Extracellular Matrix Deposition," 2010, Tissue Engineering: Part A, 16(5):1791-1800.

Lehto et al., "Skeletal Muscle Injury—Molecular Changes in the Collagen During Healing," 1985, Res Exp Med, 185:95-106.

Li et al., "Effects of administration route on migration and distribution of neural progenitor cells transplanted into rats with focal cerebral ischemia, an MRI Study," J Cereb Blood Flow Metab, Mar. 2010, 30(3):653-662.

Li et al., "Nell-1 Enhances Bone Regeneration in a Rat Critical-Sized Femoral Segmental Defect Model," Feb. 2011, Plast Reconstr Surg, 127(2):580-587.

Li et al., "Neural EGFL-like 1 is a Downstream Regulator of Runt-Related Transcription Factor 2 in Chondrogenic Differentiation and Maturation," May 2017, Am J Pathol, 187(5):963-972.

Lin et al., "Coagulation Dysregulation as a Barrier to Xenotransplantation in the Primate," Transpl Immunol, Jun. 2009, 21(2):75-80.

Liu, "Characterizing the Role of the Nell1 Gene in Cardiovascular Development," American Association for the Advancement of Science, San Francisco, CA, Presentation on Feb. 15-17, 2007 (Abstract).

Liu et al., "Characterizing the Role of the Nell1 Gene in Cardiovascular Development," U.S. Department of Energy Journal of Undergraduate Research, 2007.

Liu et al., "Characterizing the role of the Nell1 gene in cardiovascular development," Oak Ridge Science Semester Poster Presentation, ORNL, Oak Ridge, TN, Aug. 11, 2006 (Poster).

Lu et al., "The osteoinductive properties of Nell-1 in a rat spinal fusion model," The Spine Journal, 2007, 7:50-60.

Luce et al., "The neuronal EGF-related genes NELL1 and NELL2 are expressed in hemopoietic cells and developmentally regulated in the B lineage," Gene, 1999, 231:121-126.

Lui, "Stem cell technology for tendon regeneration: current status, challenges, and future research directions," 2015, Stem Cells and Cloning: Advances and Applications, 8:163-174.

Madin et al., "A highly efficient and robust cell-free protein synthesis system prepared from wheat embryos: Plants apparently contain a suicide system directed at ribosomes," Jan. 18, 2000, Proc Natl Acad Sci USA, 97(2):559-564.

Maeda et al., "Brain Specific Human Genes, NELL1 and NELL2, Are Predominantly Expressed in Neuroblastoma and Other Embryonal Neuroephithelial Tumors," Neurol Med Chir (Tokyo), 2001, 41(12):582-588.

Martin, "Wound Healing—Aiming for Perfect Skin Regeneration," Science, Apr. 1997, 276:75-81.

(56) References Cited

OTHER PUBLICATIONS

Matsuhashi et al., "New Gene, nel, Encoding a Mr 93 K Protein With EGF-Like Repeats Is Strongly Expressed in Neural Tissues of Early Stage Chick Embryos," 1995, Developmental Dynamics, 203:212-222.

Mitchell et al., "Nell1 Protein Reduces the No. of Sunburned Cells and Modulates the Inflammatory Response after UV-induced Damage in a 3D Human Skin Model," Mar. 16-20, 2012, 70th Annual Meeting of the American Academy of Dermatology, San Diego, CA.

Morgan et al., "Effects of extracorporeal shock wave therapy on wounds of the distal portion of the limbs in horses," May 1, 2009, J Am Vet Med Assoc, 234(9):1154-1161.

Mori et al., "A Genome-Wide Search Identifies Epigenetic Silencing of Somatostatin, Tachykini-1, and 5 Other Genes in Colon Cancer," 2006, Gastroenterology, 131:797-808.

Nakamura et al., "Oligomerization-induced Conformational Change in the C-terminal Region of Nel-like Molecule 1 (NELL1) Protein is Necessary for the Efficient mediation of Murine MC3T3-E1 Cell Adhesion and Spreading," Journal of Biological Chemistry, Apr. 4, 2014, 289(14):9781-9794.

Nakamura et al., "Structure-Function Analysis of Nel, a Thrombospondin-1-like Glycoprotein Involved in Neural Development and Functions," J Biol Chem, 2012, 287(5):3282-3291.

Naldini, "Ex vivo gene transfer and correction for cell-based therapies," Nature Reviews, Genetics, May 2011, 12:301-315.

Narang et al., "Biological and Biomaterial Approaches for Improved Islet Transplantation," Pharmacol Rev, 2006, 58(2):194-243.

Nemoto et al., "Tenascin-C Expression in Equine Tendon-derived Cells During Proliferation and Migration," 2013, J Equine Sci, 24(2):17-24.

Ngo et al., "Computational Complexity, Protein Structure Prediction, and the Levinthal Paradox," In Merz and La Grand (Eds), The Protein Folding Problem and Tertiary Structure Prediction, Birkhäuser Boston, 1994, pp. 434-506.

Nixon et al., "Effect of adipose-derived nucleated cell fractions on tendon repair in horses with collagenase-induced tendinitis," Jul. 2008, Am J Vet Res, 69(7):928-937.

Norrman et al., "Quantitative Comparison of Constitutive Promoters in Human ES Cells," PLoS One, 2010, 5(8):1-10.

Oke, "Regenerative Therapy Trends and Techniques in Horses," May 18, 2016, Article #37581, pp. 1-4.

Orlic et al., "Transplanted Adult Bone Marrow Cells Repair Myocardial Infarcts in Mice," Ann NY Acad Sci, 2001, 938(1):221-230.

Ott et al., "From cardiac repair to cardiac regeneration-ready to translate?," Expert Opin Biol Ther., 2006, 6(9):867-878.

Pakvasa et al., "Neural EGF-like protein 1 (NELL1-): Signaling crosstalk in mesenchymal stem cells and applications in regenerative medicine," 2017, Genes & Diseases, 4:127-137.

Pauly et al., "BMP2 and BMP7 affect human rotator cuff tendon cells in vitro," 2011, J Shoulder Elbow Surg, pp. 1-10.

Pettit et al., "The development of site-specific drug-delivery systems for protein and peptide biopharmaceuticals," Tibtech, 1998, 16:343-349.

Prieto et al., "Cells as vehicles for therapeutic genes to treat liver diseases," Gene Therapy, 2008, 15:765-771.

Raymon et al., "Application of ex Vivo Gene Therapy in the Treatment of Parkinson's Disease," Experimental Neurology, 1997, 144:82-91.

Reporter, The, Jun. 2006, No. 78, published by Oak Ridge National Laboratory, accessible on line at http://www.oml.gov/info/reporter/no78/June06 dw.htm.

Rich, "Single-Center Study of 83 Horses with Suspensory Injuries Treated with Adipose-Derived Stem and Regenerative Cells," Stem Cell Discovery, 2014, 4:44-53.

Richardson et al., "Stem cells in veterinary medicine—Attempts at regenerating equine tendon after injury," Oct. 2007, Trends in Biotechnology, pp. 1-10.

Rinchik et al., "Functional annotation of mammalian genomic DNA sequence by chemical mutagenesis: A fine-structure genetic mutation map of a 1- to 2-cM segment of mouse chromosome 7 corresponding to human chromosome 11p. 14-p. 15," PNAS, Jan. 22, 2002, 99(2):844-849.

Rosenthal et al., "Growth Factor Enhancement of Cardiac Regeneration," Cell Transplant, 2006, 15(Suppl1):S41-S45.

Rubart et al., "Cell-based Approaches for Cardiac Repair," Ann NY Acad Sci, 2006, 1080:34-38.

Ruszczak, Effect of collagen matrices on dermal wound healing, 2003, Advanced Drug Delivery Reviews, 55:1595-1611.

Santini et al., "Signalling pathways in cardiac rengeneration," Novartis Found Symp, 2006, 274:228-243.

Sawasaki et al., "Construction of an efficient expression vector for coupled transcription/translation in a wheat germ cell-free system," 2000, Nucleic Acids Symposium Series, 44:9-10.

Sawasaki et al., "A cell-free protein synthesis system for high-throughput proteomics," Nov. 12, 2002, Proc Natl Acad Sci USA, 99(23):14652-14657.

Schmitt et al., "BMP2 initiates chondrogenic lineage development of adult human mesenchymal stem cells in high-density culture," Int Soc Differentiation, 2003, 71:567-577.

Schramme et al., "A surgical tendonitis model in horses: Technique, clinical, ultrasonographic and histological characterization," 2010, Vet Comp Orthop Traumatol, 23(04):231-239.

Schumacher et al., "Kinetics of healing of grafted and nongrafted wounds on the distal portion of the forelimbs of horses," 1992, Am J Vet Res 53(9):1568-1571—Abstract only.

Schwarting et al., "Bone Morphogenetic Protein 7 (BMP-7) Influences Tendon-Bone Integration In Vitro," Feb. 2, 2015, PLoS One, 10(2):1-17.

September et al., "Tendon and ligament injuries: the genetic component," 2007, Br J Sports Med, 41:241-246.

Sethi et al., "Neural epidermal growth factor-like 1 protein (NELL-1) associated membranous nephropathy," Kidney International, 2020, 97:163-174.

Shen et al., "BMP2-Induced Inflammation Can Be Suppressed by the Osteoinductive Growth Factor NELL-1," Nov. 2013, Tissue Eng Part A, 19(21-22):2390-2401.

Shen et al., "Knock Down of NELL2 in Wilms' Tumor Cell Line," Journal of the William Jarvie Society, 2006, 49:41, Abstract.

Shen et al., "Nell-1 Promotes Cell Adhesion and Differentiation via Integrin (1," 2012, J of Cellular Biochemistry, 113:3620-3628.

Siu et al., "NELL-1 Promotes Cartilage Regeneration in an In Vivo Rabbit Model," Tissue Eng, Part A, 2012, 18(3-4):252-261.

Siu et al., "Nell-1 Protein Promotes Bone Formation in a Sheep Spinal Fusion Model," 2011, Tissue Eng, Part A, 17(7-8):1123-1135.

Strauer et al., "Stem Cell Therapy in Perspective," Circulation, 2003, 107:929-934.

Sun et al., "Targeted Deletion of Collagen V in Tendons and Ligaments Results in a Classic Ehlers-Danlos Syndrome Joint Phenotype," May 2015, Am J Pathol 185(5):1436-1447.

Tan, "A Review and Update on Tendon and Ligament Injuries in Horses, " Mar. 30, 2016, The Horse, pp. 1-7.

Taylor et al., "Gene expression markers of tendon fibroblasts in normal and diseased tissue compared to monolayer and three dimensional culture systems," 2009, BMC Musculoskeletal Disorders, 10:27, 10 pp.

Tempfer et al., "Perivascular cells of the supraspinatus tendon express both tendon- and stem cell-related markers," Histochem Cell Biol, 2009, 131:733-741.

Theoret, "Wound Repair in the Horse: Problems and Proposed Innovative Solutions," 2004, Clin Tech Equine Pract, 3:134-140.

Thomas, A-Cell Therapy Offers Renewed Hope for Horses Incurring Tendon and Ligament Injuries, Sep. 12, 2005, The Chronicle of the Horse, pp. 134-137.

Ting et al., "Human NELL-1 Expressed in Unilateral Coronoal Synostosis," J Bone Miner Res, 1999, 14(1):80-89.

Trollet et al., "Gene therapy for muscular dystrophy: current progress and future prospects," Expert Opin Biol Ther, 2009, 9(7):849-866.

Tsutsumi et al., "The Novel Gene Encoding a Putative Transmembrane Protein is Mutated in Gnathodiaphyseal Dysplasia (GDD)," Am J Hum Genet, 2004, 74:1255-1261.

(56) References Cited

OTHER PUBLICATIONS

Turner et al., "Human NELL1 Protein Augments Constructive Tissue Remodeling with Biologic Scaffolds," 2013, Cells Tissues Organs, 2013, DOI: 10.1159/000356491.

Watanabe et al., "Cloning and Characterization of Two Novel Human cDNAs (NELL1 and NELL2) Encoding Proteins with Six EGF-like Repeats," Genomics, 1996, 38:273-276.

Watts et al., "A collagenase gel/physical defect model for controlled induction of superficial digial tendonitis," 2012, Equine Veterinary Journal, 44(5):576-586.

Wells, "Additivity of Mutational Effects in Proteins," Am Chem Soc, Sep. 18, 1990, 29(37):8509-8517.

Xue et al., "NELL 1 promotes high-quality bone regeneration in rat femoral distraction osteogenesis model," 2011, Bone, 48:485-495.

Yamamoto et al., "Regulation of bone morphogenetic proteins in early embryonic development," Naturwissenschaften, 2004, 91:519-534.

Yang et al., "In vitro and in vivo induction of bone formation based on ex vivo gene therapy using rat adipose-derived adult stem cells expressing BMP-7," Cytotherapy, 2005, 7(3):273-281.

Yang et al., "Tendon and Ligament Regeneration and Repair: Clinical Relevance and Developmental Paradigm," Sep. 2013, Birth Defects Res C Embryo Today, 99(3):203-222.

Zhang et al., "Bioactivity and circulation time of PEGylated NELL-1 in mice and the potential for osteoporosis therapy," 2014, Biomaterials, 35:6614-6621.

Zhang et al., "Craniosynostosis in transgenic mice overexpressing Nell-1," J Clin Invest, Sep. 2002, 110(6):861-870.

Zhang et al., "Nell-1 induces acrania-like cranioskeletal deformities during mouse embryonic development," Laborabory Investigation, 2006, 86(7):633-644.

Zhang et al., "Overexpression of Nell1, a Craniosynostosis-Associated Gene, Induces Apoptosis in Osteoblasts During Craniofacial Development," J Bone Miner Res, 2003, 18(12):2126-2134.

Zhang et al., "The Nell-1 Growth Factor Stimulates Bone Formation by Purified Human Perivascular Cells," Tissue Engineering: Part A, 2011, 17(19-20):2497-2509.

Zhu et al., "NEL-like molecule-1-modified bone marrow mesenchymal stem cells/poly lactic-co-glycolic acid composite improves repair of large osteochondral defects in mandibular condyle," 2011, Osteoarthritis and Cartilage, 19:743-750.

SEQUENCE LISTING

```
Sequence total quantity: 19
SEQ ID NO: 1            moltype = DNA  length = 3255
FEATURE                 Location/Qualifiers
source                  1..3255
                        mol_type = unassigned DNA
                        organism = Homo sapiens
CDS                     154..2586
SEQUENCE: 1
atatgcgagc gcagcacccg gcgctgccga gccacctccc ccgccgcccg ctagcaagtt   60
tggcggctcc aagccaggcg cgcctcagga tccaggctca tttgcttcca cctagcttcg  120
gtgccccctg ctaggcgggg accctcgaga gcgatgccga tggatttgat tttagttgtg  180
tggttctgtg tgtgcactgc caggacagtg gtgggctttg ggatggaccc tgaccttcag  240
atggatatcg tcaccgagct tgaccttgtg aacaccaccc ttggagttgc tcaggtgtct  300
ggaatgcaca atgccagcaa agcattttta tttcaagaca tagaaagaga gatccatgca  360
```

```
gctcctcatg tgagtgagaa attaattcag ctgttccgga acaagagtga attcaccatt   420
ttggccactg tacagcagaa gccatccact tcaggagtga tactgtccat tcgagaactg   480
gagcacagct attttgaact ggagagcagt ggcctgaggg atgagattcg gtatcactac   540
atacacaatg gaagccaagg acagaggca cttccttacc gcatggcaga tggacaatgg   600
cacaaggttg cactgtcagt tagcgcctct catctcctgc tccatgtgca ctgtaacagg   660
atttatgagc gtgtgataga ccctccagat accaacttc ccccaggaat caatttatgt   720
cttggccagc gcaaccaaaa gcatggctta ttcaaaggga tcatccaaga tgggaagatc   780
atctttatgc cgaatggata tataaacacag tgtccaaatc taaatcacac ttgcccaacc   840
tgcagtgatt tcttaagcct ggtgcaagga ataatgggatt tacaagagct tttggccaag   900
atgactgcaa aactaaatta tgcagagaca agacttagtc aattggaaaa ctgtcattgt   960
gagaagactt gtcaagtgag tggactgctc tatcgagatc aagacttg ggtagatggt  1020
gaccattgca ggaactgcac ttgcaaaagt ggtgccgtgg aatgccgaag gatgtcctgt  1080
ccccctctca attgctcccc agactcccctc ccagtgcaca ttgctggcca gtgctgtaag  1140
gtctgccgac caaaatgtat ctatggagga aaagttcttg cagaaggcca gcggatttta  1200
accaagagct gtcgggaatg ccgaggtgga gttttagtaa aaattacaga aatgtgtcct  1260
cctttgaact gctcagaaaa ggatcacatt cttcctgaga atcagtgctg ccgtgtctgt  1320
agaggtcata acttttgtgc agaaggacct aaatgtggtg aaaactcaga gtgcaaaaac  1380
tggaatacaa aagctacttg tgagtgcaag agtggttaca tctctgtcca ggagactct  1440
gcctactgtg aagatattga tgagtgtgca gctaagatgc attactgtca tgccaatact  1500
gtgtgtgtca accttcctgg gttatatcgc tgtgactgtg tcccaggata cattcgtgtg  1560
gatgacttct cttgtacaga acacgatgaa tgtggcagcg ccagcacaa ctgtgatgag  1620
aatgccatct gcaccaacac tgtccaggga cacagctgca cctgcaaacc gggctacgtg  1680
gggaacggga ccatctgcag agctttctgt gaagagggct gcagatacgg tggaacgtgt  1740
gtggctccca caaatgtgt ctgtccatct ggattcacag aagccactg cgagaaagat  1800
attgatgaat gttcagaggg aatcattgag tgccacaacc attcccgctg cgttaacctg  1860
ccagggtggt accactgtga gtgcagaagc ggtttccatg acgatggac ctattcactg  1920
tccgggagt cctgtattga cattgatgaa tgtgccttaa gaactcacac tgttggaac  1980
gattctgcct gcatcaacct ggcaggggc tttgactgtc tctgcccctc tgggccctcc  2040
tgctctggtg actgtcctca tgaagggggg ctgaagcaca atggccaggt gtggaccttg  2100
aaagaagaca ggtgttctgt ctgctcctgc aaggatgcca agatattctg ccgacggaca  2160
gcttgtgatt gccagaatcc aagtgctgac ctattctgtt gcccagaatg tgacaccaga  2220
gtcacaagtc aatgtttaga ccaaaatggt cacaagctgt atcgaagtgg agacaattgg  2280
acccatagct gtcagcagtg tcggtgtctg aaggagagg tagattgctg gccactcact  2340
tgccccaact tgagctgtga gtatacagct atcttagaag gggaagttg tccccgctgt  2400
gtcagtgacc cctgcctagc tgataacatc acctatgaca tcagaaaaac ttgcctggac  2460
agctatggtg tttcacggct tagtggctca gtgtggacga tggctggatc tcctgcaca  2520
acctgtaaat gcaagaatgg aagagtctgt tgttctgtgg attttgagtg tcttcaaaat  2580
aattgaagta tttacagtgg actcaacgca gaagaatgga cgaaatgacc atccaacgtg  2640
attaaggata ggaatcggta gttttgtttt tttgtttgtt ttgttttttt aaccacagat  2700
aattgccaaa gtttccacct gaggacggtg tttggaggtt gccttttgga cctaccactt  2760
tgctcattct tgctaaccta gtcaggtga cctacagtgc cgtgcattta agtcaatggt  2820
tgttaaaaga agtttcccgt gttgtaaatc atgtttccct tatcagatca tttgcaaata  2880
catttaaatg atctcatggt aaatgttgat gtattttttg gttatttttg tgtactaaca  2940
taatagagag agactcagct cctttttatt atttttgtga ttatggatc aaattctaaa  3000
ataaagttgc ctgttgtgac ttttgtccca tctactgcat acttagtgct gagatccctg  3060
taaaatgttt tgatgaaaat atgtatgtag agtccagtcg cattatacat acatttcata  3120
gtgctgaacc ttcttaaatg cctactcatt cagcttaaac aggctgaagc caagtatgac  3180
aaagagggga agggccaaaa acataatcaa agaataattt taaagagaat tcttgtctct  3240
cttgcaaaaa aaaaa                                                    3255

SEQ ID NO: 2           moltype = AA   length = 810
FEATURE                Location/Qualifiers
source                 1..810
                       mol_type = protein
                       organism = Homo sapiens
SEQUENCE: 2
MPMDLILVVW FCVCTARTVV GFGMDPDLQM DIVTELDLVN TTLGVAQVSG MHNASKAFLF    60
QDIEREIHAA PHVSEKLIQL FRNKSEFTIL ATVQQKPSTS GVILSIRELE HSYFELESSG   120
LRDEIRYHYI HNGKPRTEAL PYRMADGQWH KVALSVSASH LLLHVDCNRI YERVIDPPDT   180
NLPPGINLWL GQRNQKHGLF KGIIQDGKII FMPNGYITQC PNLNHTCPTC SDFLSLVQGI   240
MDLQELLAKM TAKLNYAETR LSQLENCHCE KTCQVSGLLY RDQDSWVGD HCRNCTCKSG    300
AVECRRMSCP PLNCSPDSLP VHIAGQCCKV CRPKCIYGGK VLAEGQRILT KSCRECRGGV   360
LVKITEMCPP LNCSEKDHIL PENQCCRVCR GHNFCAEGPK CGENSECKNW NTKATCECKS   420
GYISVQGDSA YCEDIDECAA KMHYCHANTV CVNLPGLYRC DCVPGYIRVD DFSCTEHDEC   480
GSGQHNCDEN AICTNTVQGH SCTCKPGYVG NGTICRAFCE EGCRYGGTCV APNKCVPSG    540
FTGSHCEKDI DECSEGIIEC HNHSRCVNLP GWYHCECRSG FHDDGTYSLS GESCIDIDEC   600
ALRTHTCWND SACINLAGGF DCLCPSGPSC SGDCPHEGGL KHNGQVWTLK EDRCSVCSCK   660
DGKIFCRRTA CDCQNPSADL FCCPECDTRV TSQCLDQNGH KLYRSGDNWT HSCQQCRCLE   720
GEVDCWPLTC PNLSCEYTAI LEGECCPRCV SDPCLADNIT YDIRKTCLDS YGVSRLSGSV   780
WTMAGSPCTT CKCKNGRVCC SVDFECLQNN                                    810

SEQ ID NO: 3           moltype = DNA   length = 3114
FEATURE                Location/Qualifiers
source                 1..3114
                       mol_type = unassigned DNA
                       organism = Homo sapiens
CDS                    154..2445
SEQUENCE: 3
atatgcgagc gcagcacccg gcgctgccga gccacctccc ccgccgcccg ctagcaagtt    60
```

```
tggcggctcc aagccaggcg cgcctcagga tccaggctca tttgcttcca ccctagcttcg    120
gtgcccctg  ctaggcgggg accctcgaga gcgatgccga tggatttgat tttagttgtg     180
tggttctgtg tgtgcactgc caggacagtg gtgggctttg ggatggaccc tgaccttcag    240
atggatatgc tcaccgagct tgaccttgtg aacaccaccc ttggagttgc tcaggtgtct    300
ggaatgcaca atgccagcaa agcattttta tttcaagaca tagaaagaga gatccatgca    360
gctcctcatg tgagtgagaa attaattcag ctgttccgga acaagagtga attcaccatt    420
ttggccactg tacagcagaa gccatccact tcaggagtga tactgtccat tcgagaactg    480
gagcacagct attttgaact ggagagcagt ggcctgaggg atgagattcg gtatcactac    540
atacacaatg ggaagccaag gacagaggca cttccttacc gcatggcagg tggacaattgg   600
cacaaggttg cactgtcagt tagcgcctct catctcctgc tccatgtcga ctgtaacagg    660
atttatgagc gtgtgataga ccctccagat accaaccttc ccccaggaat caatttatgg    720
cttggccagc gcaaccaaaa gcatggctta ttcaaaggga tcatccaaga tgggaagatc    780
atcttttatgc cgatggata  tataacacag tgtccaaatc taaatcacac ttgccctgcc    840
tgcagtgatt tcttaagcct ggtgcaagga ataatggatt tacaagagct tttggccaag    900
atgactgcaa aactaaatta tgcagagaca agacttagtc aattggaaaa ctgtcattgt    960
gagaagactt gtcaagtgag tggactgctc tatcgagatc aagactcttg ggtagatggt   1020
gaccattgca ggaactgcac ttgcaaaagt ggtgccgtgg aatgccgaag gatgtcctgt   1080
cccctctca  attgctcccc agactccctc ccagtgcaca ttgctggcca gtgctgtaag   1140
gtctgccgac caaaatgtat ctatggagga aaagttcttg caggaaggcc agcggatttta  1200
accaagagct gtcgggaatg ccgaggtgga gttttagtaa aaattacaga aatgtgtcct   1260
cctttgaact gctcagaaaa ggatcacatt cttcctgaga atcagtgctg ccgtgtctgt   1320
agaggtcata acttttgtgc agaagaacct aaatgtggtg aaaactcaga gtgcaaaaac  1380
tggaatacaa aagctacttg tgagtgcaag agtggttaca tctctgtcca gggagactgt   1440
gcctactgtg aagatattga tgagtgtgca gctaagatgc attactgtca tgccaatact   1500
gtgtgtgtca accttcctgg gttatatcgc tgtgactgtg tcccaggata cattcgtgtg   1560
gatgacttct cttgtacaga acacgatgaa tgtggcaggg gccagcacaa ctgtgatgag   1620
aatgccatct gcaccaacac tgtccaggga cacagctgca cctgcaaacc gggctacgtg   1680
gggaacggga ccatctgcag agcttttctgt gaagagggct gcagatacgg tggaacgtgt   1740
gtggctccca caaatgtgt  ctgtccatct ggattcacag gaagccactg cgagaaagac   1800
attgatgaat gtgccttaag aactcacacc tgttggaacg attctgcctg catcaacctg   1860
gcaggggggct ttgactgtct ctgcccctct gggcccctcct gctctggtga ctgtcctcat   1920
gaaggggggc tgaagcacaa tggccaggtg tggaccttga agaagacag  tgttctgtc    1980
tgctcctgca aggatggcaa gatattctgc gacggacact tgtgattg   ccagaatcca   2040
agtgctgacc tattctgttg cccagaatgt gacaccagag tcacaagtca atgtttagac   2100
caaaatggtc acaagctgta tcgaagtgga gacaattgga cccatagctg tcagcagtgc   2160
cggtgtctgg aaggagaggt agattgctgg ccactcactt gccccaactt gagctgtgag   2220
tatacagcta tcttagaagg ggaatgttgt cccgctgtg  tcagtgaccc ctgcctagct   2280
gataacatca ccctatgacat cagaaaaact tgcctgacaa gctatggtgt ttcacggctt   2340
agtgcggctgt tgttctgtgga ttttgagtgt cttcaaaata attgaagtat ttacagtgga   2460
ctcaacgcag aagaatggac gaaatgacca tccaacgtga ttaaggatag aatcggtag   2520
tttggttttt ttgtttgttt tgttttttta accacagata attgccaaag tttccacctg   2580
aggacggtgt ttggaggttg ccttttggac ctaccactttt gctcattctt gctaacctag   2640
tctaggtgac ctacagtgcc gtgcatttaa gtcaatggtt gttaaaagaa gtttcccgtg   2700
ttgtaaatca tgtttcccttt atcagatcat ttgcaaatac atttaaatga tctcatggta   2760
aatgttgatg tattttttgg tttatttttgt gtactaacat aatagagaga gactcagctc   2820
ctttttattta tttttgttgat ttatggatca aattctaaaa taagtttgcc tgttgtgact   2880
tttgtcccat ctactgcata cttagtgctg agatccctgt aaaatgtttt gatgaaaata   2940
tgtatgtaga gtccagtcgc attatacata catttcatag tgctgaacct tcttaaatgc   3000
ctactcattc agcttaaaca ggctgaagcc aagtatgaca agaggggaa  gggccaaaaa   3060
cataatcaaa gaataatttt aaagagaatt cttgtctctc ttgcaaaaaa aaaa          3114
```

```
SEQ ID NO: 4             moltype = AA    length = 763
FEATURE                  Location/Qualifiers
source                   1..763
                         mol_type = protein
                         organism = Homo sapiens
SEQUENCE: 4
MPMDLILVVW  FCVCTARTVV  GFGMDPDLQM  DIVTELDLVN  TTLGVAQVSG  MHNASKAFLF    60
QDIEREIHAA  PHVSEKLIQL  FRNKSEFTIL  ATVQQKPSTS  GVILSIRELE  HSYFELESSG   120
LRDEIRYHYI  HNGKPRTEAL  PYRMADGQWH  KVALSVSASH  LLLHVDCNRI  YERVIDPPDT   180
NLPPGINLWL  GQRNQKHGLF  KGIIQDGKII  FMPNGYITQC  PNLNHTCPTC  SDFLSLVQGI   240
MDLQELLAKM  TAKLNYAETR  LSQLENCHCE  KTCQVSGLLY  RDQDSWVDGD  HCRNCTCKSG   300
AVECRRMSCP  PLNCSPDSLP  VHIAGQCCKV  CRPKCIYGGK  VLAEGQRILT  KSCRECRGGV   360
LVKITEMCPP  LNCSEKDHIL  PENQCCRVCR  GHNFCAEGPK  CGENSECKNW  NTKATCECKS   420
GYISVQGDSA  YCEDIDECAA  KMHYCHANTV  CVNLPGLYRC  DCVPGYIRVD  DFSCTEHDEC   480
GSGQHNCDEN  AICTNTVQGH  SCTCKPGYVG  NGTICRAFCE  EGCRYGGTCV  APNKCVCPSG   540
FTGSHCEKDI  DECALRTHTC  WNDSACINLA  GGFDCLCPSG  PSCSGDCPHE  GGLKHNGQVW   600
TLKEDRCSVC  SCKDGKIFCR  RTACDCQNPS  ADLFCCPECD  TRVTSQCLDQ  NGHKLYRSGD   660
NWTHSCQQCR  CLEGEVDCWP  LTCPNLSCEY  TAILEGECCP  RCVSDPCLAD  NITYDIRKTC   720
LDSYGVSRLS  GSVWTMAGSP  CTTCKCKNGR  VCCSSVDFECL  QNN                     763

SEQ ID NO: 5             moltype = DNA    length = 2791
FEATURE                  Location/Qualifiers
source                   1..2791
                         mol_type = unassigned DNA
                         organism = Equus caballus
CDS                      1..2376
SEQUENCE: 5
```

```
atgggctttg ggatggaccc cgaccttcaa atggatatta tcaccgagct cgacctcgtg    60
aacaccaccc ttggagtcac tcaggtgtcc ggactgcaca atgccagcaa agcattttta   120
tttcaagatg tagagagaga gatccatgca gccccacacg tgagtgagaa attaattcag   180
ctgttccgga ataagagtga attcaccttt ttggccactg tgcagcagaa gccgtcaact   240
tcaggagtga tactgtccat tcgagaactg gaaaacagtt attttgaact ggagagcagt   300
ggcctgagag atgagattcg atatcactac acacacaagg ggaagccag gacagaggca    360
cttccctacc ggatggcgga cggacggtgg cacaaggtgg cgctgtcagt tagcgcctct   420
catctcctgc tccacatcga ctgcaacagg atttatgaac gtgtgataga cactcctgag   480
accaacctcc ccccaggaag caatttgtgg ctgggtcagc gaaaccaaaa gcacggctta   540
ttcaaaggaa tcatccaaga tggaaaaatc atcttcatgc cgaatggata cataacacag   600
tgtccgaacc tgaatcgcac ttgcccaacg tgcagtgatt tcttaagcct ggtgcaagga   660
atcatggatt tacaagagct tctggccaag atgactgcga aactaaatta tgcagagaca   720
cgacttagtc aattggaaaa ctgccactgc gagaagacct gtcaagtgag tggactgctc   780
tatagagacc aggactcctg ggttgatggc gatcactgca ggaactgcac gtgcaaaagc   840
ggcgctgtgg aatgtcggag gatgtcttgt ccccctctca attgctcccc agactccctc   900
cctgtgcacg ttgccggcca gtgctgtaag gtctgccgac caaatgtat  ctacgggagg   960
aaagtccttg cagaaggcca gcggatttta accaagagct gtcgggaatg ccgaggtgga  1020
gttttagtga aaattacaga agcgtgccct cctttgaact gctcagacaa ggatcacatt  1080
ctcccagaga atcagtgctg cagcgtctgc agaggtcata acttttgtgc ggaaggacct  1140
aaatgtggtg aaaattcaga gtgcaaaaac tggaatacaa aagctacttg cgagtgcaag  1200
aatggttata tctctgtcca gggggactcc gcctactgtg aagatatcga tgagtgtgct  1260
gctaagatgc attactgtcg tgccaatact gtgtgtgtca acctgccgg  gttatatcgg  1320
tgtgactgtg tcccgggata cattcgcgtg gatgatttct cttgtacaga acatgacgaa  1380
tgtggcagcg gcagcacaa  ctgtgatgag aatgccatct gcaccaacac tgtccaggga  1440
cacagctgca cctgcaaacc gggctacgtg gggaatggga ccagctgcag agcgttctgc  1500
gaagagggct gcagatatgg cgggacatgc gtggctccta acaaatgtgt ctgtcctcct  1560
ggattcacag gaagccactg tgagaaagat attgatgaat gtacagaggg aatcattgag  1620
tgccacaacc attcccgctg cgttaacctg ccagggtggt accactgtga gtgcagaagc  1680
ggtttccatg acgatgggac ctattcactg tccggggagt cctgtattga cattgatgaa  1740
tgtgccttaa gaactcacac ctgttggaat gattctgcct gcatcaactt ggcaggggc   1800
ttcgactgcc tgtgtccctc agggccatcc tgctctggtg actgccccca cgaaggagga  1860
ctgaagcgca acgggcaggt gtggaccctg aaagaagaca ggtgttctgt gtgttcctgc  1920
aaggatggga agatattctg ccgacggaca gcttgtgatt gccagaatcc aagcgttgac  1980
ctttctgtt  gcccagagtg tgacaccagg gtcacaagtc aatgtttaga ccaaaatgga  2040
cacaagctct atcgaagtgg agacaattgg actcacagtg gtcagcagtg ccggtgtctg  2100
gaaggagagg tagattgctg gccactcact tgccccagat tgagctgtga gtacacagcc  2160
atcttggaag gggagtgttg tccacgctgt gtcagcgacc cctgcctggc ggataacatc  2220
gtctatgaca tcagagaaac ttgcctggac agctatggag tttcaaggct tagtggctca  2280
gtgtggacat tggctggatc tccctgcacg acctgcaaat gcaagaatgg aagtgtctgc  2340
tgttctgtgg attttgagtg tcttcataat aattgaagga tttaaaatgg actcatgatc  2400
gccagagaaa aatggacaaa tgaccatcca tgatgatgaa agaacaggag ttggtgtttt  2460
ttttaccaca gacaattacc aaagtctccg tctgaggaag gtgtttgcag gttgcctttt  2520
ggacctccca ctctgctcat tcttgctaac ctagtctagg tgacctacag tgtcatttcag 2580
tctatggttg ttaaaagaag ttttccgtgt tgtaaatcac gtttcccta  ccaggtcatt  2640
gcaaatacat ttaaatgatt tcatggtaaa tgttgatgta ttttttgggt ttatttttgtg 2700
tactaacata atagagattc agctgctttt atttattttt tcttgactt  tttggatcaaa 2760
ttcaacaaat aaagttgcct gttgtgattt t                                 2791
```

SEQ ID NO: 6    moltype = AA  length = 791
FEATURE      Location/Qualifiers
source       1..791
          mol_type = protein
          organism = Equus caballus
SEQUENCE: 6

```
MGFGMDPDLQ MDIITELDLV NTTLGVTQVS GLHNASKAFL FQDVEREIHA APHVSEKLIQ    60
LFRNKSEFTF LATVQQKPST SGVILSIREL ENSYFELESS GLRDEIRYHY THKGKPRTEA   120
LPYRMADGRW HKVALSVSAS HLLLHIDCNR IYERVIDTPE TNLPPGSNLW LGQRNQKHGL   180
FKGIIQDGKI IFMPNGYITQ CPNLRTCPT  CSDFLSLVQG IMDLQELLAK MTAKLNYAET   240
RLSQLENCHC EKTCQVSGLL YRDQDSWVDG DHCRNCTCKS GAVECRRMSC PPLNCSPDSL   300
PVHVAGQCCK VCRPKCIYGG KVLAEGQRIL TKSCRECRGG VLVKITEACP PLNCSDKDHI   360
LPENQCCSVC RGHNFCAEGP KCGENSECKN WNTKATCECK NGYISVQGDS AYCEDIDECA   420
AKMHYCRANT CVCVNLPGLYR CDCVPGYIRV DDFSCTEHDE CGSGQHNCDE NAICTNTVQG  480
HSCTCKPGYV GNGTSCRAFC EEGCRYGGTC VAPNKCVCPS GFTGSHCEKD IDECTEGIIE   540
CHNHSRCVNL PGWYHCECRS GFHDDGTYSL SGESCIDIDE CALRTHTCWN DSACINLAGG   600
FDCLCPSGPS CSGDCPHEGG LKRNGQVWTL KEDRCSVCSC KDGKIFCRRT ACDCQNPSVD   660
LFCCPECDTR VTSQCLDQNG HKLYRSGDNW THSCQQCRCL EGEVDCWPLT CPRLSCEYTA   720
ILEGECCPRC VSDPCLADNI VYDIRETCLD SYGVSRLSGS VWTLAGSPCT TCKCKNGSVC   780
CSVDLECLHN N                                                       791
```

SEQ ID NO: 7    moltype = DNA length = 2285
FEATURE      Location/Qualifiers
source       1..2285
          mol_type = unassigned DNA
          organism = Equus caballus
CDS         1..2235
SEQUENCE: 7

```
atgggctttg ggatggaccc cgaccttcaa atggatatta tcaccgagct cgacctcgtg    60
aacaccaccc ttggagtcac tcaggtgtcc ggactgcaca atgccagcaa agcattttta   120
tttcaagatg tagagagaga gatccatgca gccccacacg tgagtgagaa attaattcag   180
```

-continued

```
ctgttccgga ataagagtga attcaccttt ttggccactg tgcagcagaa gccgtcaact    240
tcaggagtga tactgtccat tcgaaactg gaaaacagtt attttgaact ggagagcagt    300
ggcctgagag atgagattcg atatcactac acacacaagg ggaagcccag gacagaggca    360
cttccctacc ggatggcgga cggacggtgg cacaaggtgg cgctgtcagt tagcgcctct    420
catctcctgc tccacatcga ctgcaacagg atttatgaac gtgtgataga cactcctgag    480
accaacctcc ccccaggaag caatttgtgg ctgggtcagc gaaaccaaaa gcacggctta    540
ttcaaaggaa tcatccaaga tggaaaaatc atcttcatgc cgaatggata cataacacag    600
tgtccgaacc tgaatcgcac ttgcccaacg tgcagtgatt tcttaagcct ggtgcaagga    660
atcatggatt tacaagagct tctggccaag atgactgcga aactaaatta tgcagagaca    720
cgacttagtc aattggaaaa ctgccactgc gagaagacct gtcaagtgag tggactgctc    780
tatagagacc aggactcctg ggttgatggc gatcactgta ggaactgcac gtgcaaaagc    840
ggcgctgtgg aatgtcggag gatgtcttgt cccctctca attgctcccc agactccctc    900
cctgtgcacg ttgccggcca gtgctgtaag gtctgccgac aaaatgtat ctacggaggg    960
aaagtccttg cagaaggcca gcggatttta accaagagct gtcgggaatg ccgaggtgga   1020
gtttagtga aaattacaga agcgtgccct cctttgaact gctcagacaa ggatcacatt   1080
ctcccagaga atcagtgctg cagcgtctgc agaggtcata acttttgtgc ggaaggacct   1140
aaatgtggtg aaaattcaga gtgcaaaaac tggaatacaa agctacttg cgagtgcaag   1200
aatggttata tctctgtcca gggggactcc gcctactgtg aagatatcga tgagtgtgct   1260
gctaagatgc attactgtcg tgccaatact gtgtgtgtca acctgcctgg gttatatcgg   1320
tgtgactgtg tcccgggata cattcgcgtg atgatttct cttgtacaga acatgacgaa   1380
tgtggcagcg ggcagcacaa ctgtgatgag aatgccatct gcaccaacac tgtccaggga   1440
cacagctgca cctgcaaacc gggctacgtg gggaatggga cagctgcag agcgttctgc   1500
gaagagggct gcagatatgg cgggacatgc gtggctccta caaatgtgt ctgtccttct   1560
ggattcacag gaagccactg tgagaaagac attgatgaat gtgccttaag aactcacacc   1620
tgttggaatg attctgcctg catcaacttg cagggggctc gactgcct gtgtccctca   1680
gggccatcct gctctggtga ctgcccccac gaaggaggac tgaagcgcaa cgggcaggtg   1740
tggacccctga agaagacag tgttctgtg tgttcctgca aggatgggaa gatattctgc   1800
cgacggacag cttgtgattg ccagaatcca agcgttgacc ttttctgttg cccagagtgt   1860
gacaccaggg tcacaagtca atgtttagac caaaatggac acaagctcta tcgaagtgga   1920
gacaattgga ctcacagctg tcagcagtgc cggtgtctgg aaggagaggt agattgctgg   1980
ccactcactt gccccagatt gagctgtgag tacacagcca tcttggaagg ggagtgttgt   2040
ccacgctgtg tcagcgaccc ctgcctggcg gataacatcg tctatgacat cagagaaact   2100
tgcctggaca gctatggagt ttcaaggctt agtggctcag tgtggacatt ggctggatct   2160
ccctgcacga cctgcaaatg caagaatgga agtgtctgct gttctgtgga tttggagtgt   2220
cttcataata attgaaggat ttaaaatgga ctcatgatcc ccagagaaaa atggacaaat   2280
gacca                                                             2285

SEQ ID NO: 8            moltype = AA  length = 744
FEATURE                 Location/Qualifiers
source                  1..744
                        mol_type = protein
                        organism = Equus caballus
SEQUENCE: 8
MGFGMDPDLQ MDIITELDLV NTTLGVTQVS GLHNASKAFL FQDVEREIHA APHVSEKLIQ    60
LFRNKSEFTF LATVQQKPST SGVILSIREL ENSYFELESS GLRDEIRYHY THKGKPRTEA   120
LPYRMADGRW HKVALSVSAS HLLLHIDCNR IYERVIDTPE TNLPPGSNLW LGQRNQKHGL   180
FKGIIQDGKI IFMPNGYITQ CPNLNRTCPT CSDFLSLVQG IMDLQELLAK MTAKLNYAET   240
RLSQLENCHC EKTCQVSGLL YRDQDSWVDG DHCRNCTCKS GAVECRRMSC PPLNCSPDSL   300
PVHVAGQCCK VCRPKCIYGG KVLAEGQRIL TKSCRECRGG VLVKITEACP PLNCSDKDHI   360
LPENQCCSVC RGHNFCAEGP KCGENSECKN WNTKATCECK NGYISVQGDS AYCEDIDECA   420
AKMHYCRANT VCVNLPGLYR CDCVPGYIRV DDFSCTEHDE CGSGQHNCDE NAICTNTVQG   480
HSCTCKPGYV GNGTSCRAFC EEGCRYGGTC VAPNKCVCPS GFTGSHCEKD IDECALRTHT   540
CWNDSACINL AGGFDCLCPS GPSCSGDCPH EGGLKRNGQV WTLKEDRCSV CSCKDGKIFC   600
RRTACDCQNP SVDLFCCPEC DTRVTSQCLD QNGHKLYRSG DNWTHSCQQC RCLEGEVDCW   660
PLTCPRLSCE YTAILEGECC PRCVSDPCLA DNIVYDIRET CLDSYGVSRL SGSVWTLAGS   720
PCTTCKCKNG SVCCSVDLEC LHNN                                         744

SEQ ID NO: 9            moltype = DNA  length = 2812
FEATURE                 Location/Qualifiers
source                  1..2812
                        mol_type = unassigned DNA
                        organism = Mus musculus
CDS                     40..2472
SEQUENCE: 9
gcgttggtgc gccctgcttg gcgggggggcc tccggagcga tgccgatgga tgtgattta     60
gttttgtggt tctgtgtgtg caccgccagg acagtgctgg gctttgggat ggaccctgac   120
cttcagatga acatcatcac tgaacttgac cttgtgaaca ccaccctggg cgtcactcag   180
gtggctggac tacacaatgc cagtaaggca tttctgtttc aagatgtaca gagagagatc   240
cactcagccc ctcatgtgag tgagaagctg atccagctat tccggaataa gagtgagttt   300
acctttttgg ctacagtgca gcagaagccg tccacctcag gggtgatact gtcgatccgg   360
gagctggaac acagctattt tgaactggag agcagtggcc aagagaaga gatacgctat   420
cattacatcc atggcggcaa gcccaggact gaggcccttc cctaccgcat ggccgatgga   480
cagtggcaca aggtcgcgct gtctgtgagc gcctctcacc tcctactcca tgtcgactgc   540
aataggattt atgagcgtgt gatatgtcct ccggagacca accttcctcc aggaagcaat   600
ctatggcttg gcaacgtaa tcaaaagcat ggctttttca aaggaatcc caagatggc   660
aagatcatct tcatgccgaa cggcttcatc acacagtgcc caacctaaa tcgcacttgc   720
ccaacatgcg tgatttcct gagcctggtt caaggaataa tggatttgca agagcttttg   780
gccaagatga ctgcaaaact gaattatgca gagacgagac ttggtcaact ggaaaattgc   840
cactgtgaga agacctgcca agtgagtggg ctgctctaca gggaccaaga ctcctgggta   900
```

-continued

```
gatggtgaca actgcaggaa ctgcacatgc aaaagtggtg ctgtggagtg ccgaaggatg      960
tcctgtcccc cactcaactg ttccccagac tcacttcctg tgcatatttc tggccaatgt     1020
tgtaaagttt gcagaccaaa atgtatctat ggaggaaaag ttcttgctga gggcagcgg      1080
attttaacca agacctgccg ggaatgtcga ggtggagtct tggtaaaaat cacagaagct     1140
tgccctcctt tgaactgctc agagaaggat catattcttc cggagaacca gtgctgcagg     1200
gtctgccgag gtcataactt ctgtcagaa gcacctaagt gtggagaaaa ctcggaatgc      1260
aaaaattgga atacaaaagc gacttgtgag tgcaagaatg gatacatctc tgtccagggc     1320
aactctgcat actgtgaaga tatcgatgag tgtgcagcaa agatgcacta ctgtcatgcc     1380
aacacggtgt gtgtcaactt gccggggtta tatgctctgt actgcatccc aggatacatc     1440
cgtgtggatg acttctcttg tacggagcat gatgattgtg gcagcggaca acacaactgt     1500
gacaaaaatg ccatcgtac aacacagtc cagggacaca gctgtacctg ccagccaggc      1560
tacgtgggaa atggtactgt ctgcaaagca ttctgtgaag ggttgcag atacggaggt      1620
acctgtgtgg cccctaacaa atgtgtctgt ccttctggat tcacaggaag ccactgtgag    1680
aaagatattg atgaatgtgc agagggattc gttgagtgcc acaaccactc ccgctgcgtt    1740
aaccttccag ggtggtacca ctgtgagtgc agaagcggtt tccatgacga tgggacctat    1800
tcactgtccg gggagtcctg cattgatatt gatgaatgtg cctaagaac tcacacttgt     1860
tggaatgact ctgcctgcat aacttagca ggaggatttg actgcctgtg tcctctggg      1920
ccctcctgct ctggtgactg tccccacgaa gggggctga agcataatgg gcaggtgtgg     1980
attctgagag aagacaggtg ttcagtctgt tcctgtaagg atgggaagat attctgccgg    2040
cggacagctt gtgattgcca gaatccaaat gttgaccttt tctgctgccc agagtgtgac    2100
accagggtca ctagccaatg tttagatcaa agcggacaga agctctatcg aagtggagac    2160
aactggaccc acagctgcca gcagtgccga tgtctgaagg agaggcaga ctgctggcct    2220
ctagcttgcc ctagtttgag ctgtgaatac acagccatct tgaaggaga gtgttgtccc    2280
cgctgtgtca gtgaccctg cctgctgat aatattgcct atgacatcag aaaaacttgc     2340
ctggacagct ctggtatttc gaggctgagc ggcgcagtgt ggacaatggc tggatctccc    2400
tgtacaacct gtcaatgcaa gaatgggaga gtctgctgc ctgtggatct ggtgtgtctt    2460
gagaataact gaagatttta aatgggactca tcacatgaga aaatggacaa aatgaccatc    2520
caacctgagg aagaggaggg gctgatttct ttttcttttt aaccacagtc aattaccaaa    2580
gtctccatca gaggaaggcg tttgggttgc ctttaccact ttgctcatcc ttgctgacct    2640
agtctagatg cctgcagtac cgtgtatttc ggtcgatgt tgttgagtct ccgtgctgta    2700
aatcacattt cccttgtcag atcatttaca gatacattta aaggattcca tgataaatgt    2760
taaagtacct tttgttatt ttgtgtacca acataataga gacttggcac ca            2812
```

```
SEQ ID NO: 10            moltype = AA   length = 810
FEATURE                  Location/Qualifiers
source                   1..810
                         mol_type = protein
                         organism = Mus musculus
SEQUENCE: 10
MPMDVILVLW FCVCTARTVL GFGMDPDLQM DIITELDLVN TTLGVTQVAG LHNASKAFLF     60
QDVQREIHSA PHVSEKLIQL FRNKSEFTFL ATVQQKPSTS GVILSIRELE HSYFELESSG   120
PREEIRYHYI HGGKPRTEAL PYRMADGQWH KVALSVSASH LLLHVDCNRI YERVIDPPET   180
NLPPGSNLWL GQRNQKHGFF KGIIQDGKII FMPNGFITQC PNLNRTCPTC SDFLSLVQGI   240
MDLQELLAKM TAKLNYAETR LGQLENCHCE KTCQVSGLLY RDQDSWVDGD NCRNCTCKSG   300
AVECRRMSCP PLNCSPDSLP VHISGQCCKV CRPKCIYGGK VLAEGQRILT KTCERCRGGV   360
LVKITEACPP LNCSEKDHIL PENQCCRVCR GHNFCAEAPK CGENSECKNW NTKATCECKN   420
GYISVQGNSA YCEDIDECAA KMHYCHANTV CVNLPGLYRC DCIPGYIRVD DFSCTEHDDC   480
GSGQHNCDKN AICTNTVQGH SCTCQPGYVG NGTVCKAFCE EGCRYGGTCV APNKCVPSG    540
FTGSHCEKDI DECAEGFVEC HNHSRCVNLP GWYHCECRSG FHDDGTYSLS GESCIDIDEC   600
ALRTHTCWND SACINLAGGF DCLCPSGPSC SGDCPHEGGL KHNGQVWILR EDRCSVCSCK   660
DGKIFCRRTA CDCQNPNVDL FCCPECDTRV TSQCLDQSGQ KLYRSGDNWT HSCQQCRCLE   720
GEADCWPLAC PSLSCEYTAI FEGECCPRCV SDPCLADNIA YDIRKTCLDS SGISRLSGAV   780
WTMAGSPCTT CQCKNGRVCC SVDLVCLENN                                    810
```

```
SEQ ID NO: 11            moltype = DNA   length = 2915
FEATURE                  Location/Qualifiers
source                   1..2915
                         mol_type = unassigned DNA
                         organism = Rattus norvegicus
CDS                      59..2491
SEQUENCE: 11
aagcactggt tcttgttag cgttggtgcg ccctgcttgg cggggttct ccggagcgat       60
gccgatggat gtgattttag ttttgtggtt ctgtgtatgc accgccagga cagtgttggg    120
ctttgggatg gaccctgacc ttcagctgga catcatctca gactcgacc tggtgaacac     180
caccctggga gtcacgcagg tggctggact gcacaacgcc agtaaagcat tctatttca    240
agatgtacag agagagatcc attcggcccc tcacgtgagt gagaagctga tccagctatt    300
ccggaataag agcgagttca ccttttttggc tacagtgcag cagaaaccat ccacctcagg   360
ggtgatactg tccatccggg agctggagca cagctatttt gaactggaga gcagtggccc   420
aagagaagag atacgctacc attacataca tggtggaaag cccaggactg aggccctcc    480
ctaccgcatg gcagacggac aatggcacaa ggtcgcgctg tcagtgagcg cctctcacct   540
cctgctccac atcactgca ataggattta cgagcgtgtg atagaccctc cggagaccaa    600
ccttcctcca ggaagcaatc tgtggcttgg caacgtaac caaaagcatg gctttttcaa    660
aggaatcatc caagatggta agatcatctt catgccgaat ggtttcatca cacagtgtcc    720
caacctcaat cgcacctgcc caacatgcag tgacttcctg agctggtc aagaaataat     780
ggatttgcaa gagcttttgg ccaagatgac tgcaaaactg aattatgcag agacgagact   840
tggtcaactg gaaattgcc actgtgagaa gacctgccaa gtgagtgggc tgctctacag    900
ggaccaagac tcctgggtgg atggtgacaa ctgtgggaac tgcacgtgca aaagtggtgc    960
cgtggagtgc cgcaggatgt cctgtccccc gctcaactg tccccggact cacttcctgt   1020
gcacatttcc ggccagtgtt gtaaagtttg cagaccaaaa tgtatctatg gaggaaaagt   1080
```

```
                                                               -continued
tcttgctgag ggccagcgga ttttaaccaa gacctgccgg gaatgtcgag gtggagtctt   1140
ggtaaaaatc acagaagctt gccctccttt gaactgctca gcaaaggatc atattcttcc   1200
agagaatcag tgctgcaggg tctgcccagg tcataacttc tgtgcagaag cacctaagtg   1260
cggagaaaac tcgaatgcaa aaattggaa tacaaaagca acctgtgagt gcaagaatgg    1320
atacatctct gtccagggca actctgcata ctgtgaagat attgatgagt gtgcagctaa   1380
aatgcactat tgtcatgcca acaccgtgtg tgtcaacttg ccggggttgt atcgctgtga   1440
ctgcgtccca gggtacatcc gtgtggatga cttctcttgt acggagcatg atgattgtgg   1500
cagcggacaa cacaactgcg acaaaaatgc catctgtacc aacacagtcc agggacacag   1560
ctgcacctgc cagccgggtt acgtgggaaa tggcaccatc tgcaaagcat tctgtgaaga   1620
gggttgcaga tacggaggta cctgtgtggc tcctaacaag tgtgtctgtc cttctggatt   1680
cacgggaagc cactgtgaga agatattga tgaatgcgca gagggattcg ttaatgccca    1740
caactactcc cgctgtgtta acctgccagg gtggtaccac tgtgagtgca gagcggtt    1800
ccatgacgat gggacctact cactgtccgg ggagtcctgc attgatatcg atgaatgtgc   1860
cttaagaact cacacttgtt ggaatgactc tgcctgcatc aacttagcag aggatttga    1920
ctgcctgtgt ccctctgggc cctcctgctc tggtgactgt ccccacgaag gagggctgaa   1980
gcataatggg caggtgtgga ttctgagaga agacaggtgt tcagtctgtt cctgcaagga   2040
tgggaagata ttctgccggc ggacagcttg tgattgccaa aatccaaatg ttgacccttt   2100
ttgctgccca gagtgcgata ccagggtcac cagctaatgt ttagatcaaa gtggacagaa   2160
gctctatcga agtggagaca actggaccca cagctgccaa cagtgccgat gtctggaagg   2220
agaggcagac tgctggcctc tggcttgcc tagtttgggc tgtgaataca cagccatgtt    2280
tgaagggag tgttgtcccc gatgtgtcag tgaccctgc ctggctggta atattgccta     2340
tgacatcaga aaaacttgcc tggacagttt tggtgttcg aggctgagcg gagccgtcga    2400
gacaatggct ggatctcctt gtacaacctg caaatgcaag aatggggagag tctgctgctc   2460
tgtggatctg gagtctattg agaataactg aagattttaa atggactcgt cacgtgagaa   2520
aatgggcaaa atgatcatcc cacctgagga agaagaggg ctgatttctt tttctttta    2580
accacagtca attaccaaag tctccatctg aggaaggcgt tggattgcc tttgccactt    2640
tgctcatcct tgctgaccta gtctagatgc ctgcagtacc gtgcatttcg gtcgatggtt   2700
gttgagtctc agtgttgtaa atcgcatttc cctcgtcaga tcatttacag atacatttaa   2760
agggggttcca tgataaatgt taatgtaact tttgtttatt ttgtgtactg acataataga   2820
gacttggcac catttattta ttttttcttga ttttttggatc aaattctaaa aataaagttg   2880
cctgttgcga aaaaaaaaa aaaaaaaaaa aaaaa                                2915

SEQ ID NO: 12              moltype = AA  length = 810
FEATURE                    Location/Qualifiers
source                     1..810
                           mol_type = protein
                           organism = Rattus norvegicus
SEQUENCE: 12
MPMDVILVLW FCVCTARTVL GFGMDPDLQL DIISELDLVN TTLGVTQVAG LHNASKAFLF    60
QDVQREIHSA PHVSEKLIQL FRNKSEFTFL ATVQQKPSTS GVILSIRELE HSYFELESSG   120
PREEIRYHYI HGGKPRTEAL PYRMADGQWH KVALSVSASH LLLHIDCNRI YERVIDPPET   180
NLPPGSNLWL GQRNQKHGFF KGIIQDGKII FMPNGFITQC PNLNRTCPTC SDFLSLVQGI   240
MDLQELLAKM TAKLNYAETR LGQLENCHCE KTCQVSGLLY RDQDSWVDGD NCGNCTCKSG   300
AVECRRMSCP PLNCSPDSLP VHISGQCCKV CRPKCIYGGK VLAEGQRILT KTCRECRGGV   360
LVKITEACPP LNCSAKDHIL PENQCCRVCP GHNFCAEAPK CGENSECKNW NTKATCECKN   420
GYISVQGNSA YCEDIDECAA KMHYCHANTV CVNLPGLYRC DCVPGYIRVD DFSCTEHDDC   480
GSGQHNCDKN AICTNTVQGH SCTCQPGYVG NGTICKAFCE EGCRYGGTCV APNKCVCPSG   540
FTGSHCEKDI DECAEGFVEC HNYSRCVNLP GWYHCECRSG FHDDGTYSLS GESCIDIDEC   600
ALRTHTCWND SACINLAGGF DCLCPSGPSC SGDCPHEGGL KHNGQVWILR EDRCSVCSCK   660
DGKIFCRRTA CDCQNPNVDL FCCPECDTRV TSQCLDQSGQ KLYRSGDNWT HSCQQCRCLE   720
GEADCWPLAC PSLGCEYTAM FEGECCPRCV SDPCLAGNIA YDIRKTCLDS FGVSRLSGAV   780
WTMAGSPCTT CKCKNGRVCC SVDLECIENN                                    810

SEQ ID NO: 13              moltype = AA  length = 810
FEATURE                    Location/Qualifiers
source                     1..810
                           mol_type = protein
                           organism = Felis catus
SEQUENCE: 13
MPRDVILVVW FCVCTARTVV GFGTDPDLQV DIIAELDLVN TTAGVTQVSG LHNASKAYLF    60
QETEREIHAA PHVSEKLIQL FRNKSEFSFL ATVQQKPSTS GVILSIRELE HSYFELESSG   120
LRDEIRYHYI HNGKPRTEAL PYRMADGQWH KVALSISASH LLLHVDCNRI YERVIDPPET   180
NLPPGSNVWL GQRNQKHGLF KGIIQDGKII FMPNGYITQC PNLNRTCPTC SDFLSLVQGI   240
MDLQELLAKM TAKLNYAETR LNQLENCHCE KTCQVSGLLY RDQDSWVDGD HCRNCTCKSG   300
AVECRRMSCP PLNCSPDSLP VHIAGQCCKV CRPKCIYGGK VLAEGQRILT KSCRECRGGV   360
LVKITDACPP LNCSEKDHIL PENQCCSVCR GHNFCAEGPT CGENSECKNW NTKATCECKN   420
GYISVQGDSA YCEDIDECAA KMHYCHANTV CVNLPGLYRC DCVPGYIRVD DFSCTEHDEC   480
GSGQHNCDEN AICTNTVQGH SCTCKPGYVG NGTICRAFCE EGCRYGGTCV SPNKCVCPSG   540
FTGSHCEKDI DECTEGIIEC HNHSRCVNLP GWYHCECRSG FHDDGTYSLS GESCIDIDEC   600
ALRTHTCWND SACINLAGGF DCLCPSGPSC SGDCPHEGGL KRNGQVWTLK EDRCSVCSCK   660
DGKIFCRRTA CDCQNPSVDL FCCPECDTRV TSQCLDQNGH KLYRSGDNWT HSCQQCRCLE   720
GEVDCWPLTC PNLSCEYTAM LEGECCPRCV SDPCLADNIA YDIRKTCLDS YGISRLSGAV   780
WTMAGSPCTT CKCKNGSVCC SVDLECLHNN                                    810

SEQ ID NO: 14              moltype = AA  length = 763
FEATURE                    Location/Qualifiers
source                     1..763
                           mol_type = protein
                           organism = Felis catus
```

```
SEQUENCE: 14
MPRDVILVVW  FCVCTARTVV  GFGTDPDLQV  DIIAELDLVN  TTAGVTQVSG  LHNASKAYLF   60
QETEREIHAA  PHVSEKLIQL  FRNKSEFSFL  ATVQQKPSTS  GVILSIRELE  HSYFELESSG  120
LRDEIRYHYI  HNGKPRTEAL  PYRMADGQWH  KVALSISASH  LLLHVDCNRI  YERVIDPPET  180
NLPPGSNVWL  GQRNQKHGLF  KGIIQDGKII  FMPNGYITQC  PNLNRTCPTC  SDFLSLVQGI  240
MDLQELLAKM  TAKLNYAETR  LNQLENCHCE  KTCQVSGLLY  RDQDSWVGDG  HCRNCTCKSG  300
AVECRRMSCP  PLNCSPDSLP  VHIAGQCCKV  CRPKCIYGGK  VLAEGQRILT  KSCRECRGGV  360
LVKITDACPP  LNCSEKDHIL  PENQCCSVCR  GHNFCAEGPT  CGENSECKNW  NTKATCECKN  420
GYISVQGDSA  YCEDIDECAA  KMHYCHANTV  CVNLPGLYRC  DCVPGYIRVD  DFSCTEHDEC  480
GSGQHNCDEN  AICTNTVQGH  SCTCKPGYVG  NGTICRAFCQ  EGCRYGGTCV  SPNKCVCPSG  540
FTGSHCEKDI  DECALRTHTC  WNDSACINLA  GGFDCLCPSG  PSCSGDCPHE  GGLKRNGQVW  600
TLKEDRCSVC  SCKDGKIFCR  RTACDCQNPS  VDLFCCPECD  TRVTSQCLDQ  NGHKLYRSGD  660
NWTHSCQQCR  CLEGEVDCWP  LTCPNLSCEY  TAMLEGECCP  RCVSDPCLAD  NIAYDIRKTC  720
LDSYGISRLS  GAVWTMAGSP  CTTCKCKNGS  VCCSVDLECL  HNN                    763

SEQ ID NO: 15            moltype = AA  length = 901
FEATURE                  Location/Qualifiers
source                   1..901
                         mol_type = protein
                         organism = Canis lupus
                         note = Canis familiaris
SEQUENCE: 15
MTSTSFLLWL  GCVHNTKFPF  PLVLVTRAIV  VVVVEVVGVG  SPGVRIRSTG  CDILLLYEVL   60
EHLLGIRFLC  VDQGENSCHH  GQCACRLQVI  VPKALMSVFE  AKTAVCFFPV  VGFGTDPDLQ  120
MDIITELDLV  NISLGVTQVS  GLHNASKAYV  FQDTAREIHA  APHVSEKLIQ  LFRNKSDFTF  180
LATVQQKPST  SGVILSIREL  EHSYFELESS  GLRDEIRYHM  HNGKPRTEA   PYRLADGQW   240
HKVALSVSAS  HLLLHIDCNR  IYERVIDPPE  TNLPPGSNLW  LGQRNQKHGF  FKGIIQDGKI  300
IFMPNGYITQ  CPNLNRTCPT  CSDFLSLVQG  IMDLQELLAK  MTAKLNYAET  RLSQLENCHC  360
EKTCQVSGLL  YRDQDSWVDG  DHCRNCTCKG  GAVECRRMSC  PPLNCSPDSL  PVHIAGQCCK  420
VCRPKCIYGG  RVLAEGQRIL  TKSCRECRGG  VLVKITDACP  PLNCSEKDHI  LPENQCCSVC  480
RGHNFCAEGP  KCGENSECKN  WNTKATCECK  NGYISVQGDS  AYCEDIDECA  AKMHYCHANT  540
VCVNLPGLYR  CDCVPGYIRV  DDFSCTEHDE  CGSGQHNCDE  NAICTNTVRG  HSCTCKPGYV  600
GNGTICRAFC  QEGCRYGGSC  VSPNKCVCPS  GFTGSHCEKD  IDECTEGIIE  CHNHSRCVNL  660
PGWYHCECRS  GFHDDGTYSL  SGESCIDIDE  CALRTHTCWN  DSACINLAGG  FDCLCPSGPS  720
CSGDCPHEGG  LKRNGQVWTL  KEDRCSVCSC  KDGKILCRRT  ACDCQNPSVD  LFCCPECDTR  780
VTSQCLDQNG  HKLYRSGDNW  THSCQQCRCL  EGEVDCWPLT  CPNLSCEYTA  ILEGECCPRC  840
VSDPCLADNI  AYDIRKTCLD  SYGISRLSGS  VWTMAGSPCT  TCKCKNGSVC  CSVDLECLHN  900
N                                                                      901

SEQ ID NO: 16            moltype = AA  length = 810
FEATURE                  Location/Qualifiers
source                   1..810
                         mol_type = protein
                         organism = Ovis aries
SEQUENCE: 16
MPRGVILVVC  FCVCAARTVV  GFGMDPDLQL  DIITELDLVN  TTLGVTQVSG  LHNTSKAFLF   60
QDAEREIHAA  PHVSEKLIQL  FRNKSEFTFL  ATVQQKPSTS  GVILSIRELE  HSYFELESSG  120
LRDEIRYHYM  HSGRPRTEAL  PYRLADGQWH  RVALSVSASH  LLLHIDCNRI  YERVIDPPET  180
NLPPGSNLWL  GQRNQKHGLF  KGIIQDGKII  FMPNGYITQC  PNLNRTCPTC  SDFLSLVQGI  240
MDLQELLAKM  TAKLNYAETR  LSQLENCHCE  KTCQVSGLLY  RDQDSWVGDG  HCRNCTCKSG  300
AVECRRMSCP  PLNCSPDSLP  VHIAGQCCKV  CRPKCIYGGK  VLAEGQRILS  KNCQECRGGV  360
LVKITEACPL  LNCSEKDHIL  PENQCCSVCR  GHNFCAEGPK  CGENSECKNW  NTKATCECKN  420
GYISVQGDSA  YCEDIDECAA  KMHYCHANTV  CVNLPGLYRC  DCVPGYIRVD  DFSCTEHDDC  480
GSGQHNCDEN  AICTNTVQGH  SCTCKPGYVG  NGTICRAFCE  EGCRYGGTCM  APNKCVCPSG  540
FTGSHCEKDI  DECAEGIIEC  HSHSRCVNLP  GWYHCECRSG  FHDDGTYSLS  GESCVDIDEC  600
ALRTHTCWND  SACINLAGGF  DCLCPSGPSC  SGDCPHEGGL  KRNGQVWTLK  EDRCSVCSCK  660
DGKIFCRRTA  CDCQNPSVDL  FCCPECDTRV  TSQCLDQNGN  KLYRSGDNWT  HSCQQCRCLE  720
GEVDCWPLTC  PSLSCEYTTI  LEGECCPRCV  SDPCLADNIA  YDIRKTCLDS  YGLSRLSGSV  780
WTMAGSPCTT  CKCKNGSVCC  SVDLECLHNN                                     810

SEQ ID NO: 17            moltype = AA  length = 610
FEATURE                  Location/Qualifiers
source                   1..610
                         mol_type = protein
                         organism = Homo sapiens
SEQUENCE: 17
FGMDPDLQMD  IVTELDLVNT  TLGVAQVSGM  HNASKAFLFQ  DIEREIHAAP  HVSEKLIQLF   60
RNKSEFTILA  TVQQKPSTSG  VILSIRELEH  SYFELESSGL  RDEIRYHYIH  NGKPRTEALP  120
YRMADGQWHK  VALSVSASHL  LLHVDCNRIY  ERVIDPPDTN  LPPGINLWLG  QRNQKHGLFK  180
GIIQDGKIIF  MPNGYITQCP  NLNHTCPTCS  DFLSLVQGIM  DLQELLAKMT  AKLNYAETRL  240
SQLENCHCEK  TCQVSGLLYR  DQDSWVDGDH  CRNCTCKSGA  VECRRMSCPP  LNCSPDSLPV  300
HIAGQCCKVC  RPKCIYGGKV  LAEGQRILTK  SCRECRGGVL  VKITEMCPPL  NCSEKDHILP  360
ENQCCSVCRG  HNFCAEGPKC  GENSECKNWN  TKATCECKSG  YISVQGDSAY  CEDIDECAAK  420
MHYCHANTVC  VNLPGLYRCD  CVPGYIRVDD  FSCTEHDECG  SGQHNCDENA  ICTNTVQGHS  480
CTCKPGYVGN  GTICRAFCEE  GCRYGGTCVA  PNKCVCPSGF  TGSHCEKDID  ECSEGIIECH  540
NHSRCVNLPG  WYHCECRSGF  HDDGTYSLSG  ESCIDIDECA  LRTHTCWNDS  ACINLAGGFD  600
CLCPSGPSCS                                                             610

SEQ ID NO: 18            moltype = AA  length = 610
```

```
FEATURE              Location/Qualifiers
source               1..610
                     mol_type = protein
                     organism = Equus caballus
SEQUENCE: 18
FGMDPDLQMD  IITELDLVNT  TLGVTQVSGL  HNASKAFLFQ  DVEREIHAAP  HVSEKLIQLF   60
RNKSEFTFLA  TVQQKPSTSG  VILSIRELEN  SYFELESSGL  RDEIRYHYTH  KGKPRTEALP  120
YRMADGRWHK  VALSVSASHL  LLHIDCNRIY  ERVIDTPETN  LPPGSNLWLG  QRNQKHGLFK  180
GIIQDGKIIF  MPNGYITQCP  NLNRTCPTCS  DFLSLVQGIM  DLQELLAKMT  AKLNYAETRL  240
SQLENCHCEK  TCQVSGLLYR  DQDSWVDGDH  CRNCTCKSGA  VECRRMSCPP  LNCSPDSLPV  300
HVAGQCCKVC  RPKCIYGGKV  LAEGQRILTK  SCRECRGGVL  VKITEACPPL  NCSDKDHILP  360
ENQCCSVCRG  HNFCAEGPKC  GENSECKNWN  TKATCECKNG  YISVQGDSAY  CEDIDECAAK  420
MHYCRANTVC  VNLPGLYRCD  CVPGYIRVDD  FSCTEHDECG  SGQHNCDENA  ICTNTVQGHS  480
CTCKPGYVGN  GTSCRAFCEE  GCRYGGTCVA  PNKCVCPSGF  TGSHCEKDID  ECTEGIIECH  540
NHSRCVNLPG  WYHCECRSGF  HDDGTYSLSG  ESCIDIDECA  LRTHTCWNDS  ACINLAGGFD  600
CLCPSGPSCS                                                              610

SEQ ID NO: 19        moltype = AA  length = 599
FEATURE              Location/Qualifiers
source               1..599
                     mol_type = protein
                     organism = Bos taurus
SEQUENCE: 19
MALCSFSVVG  FGLDPDLQLD  IITELDLVNT  TLGVTQVSGL  HNTSKAFLFQ  DAEREIHAAP   60
HVSEKLIQLF  RNKSEFTFLA  TVQQKPSTSG  VILSIRELEH  SYFELESSGL  RDEIRYHYVH  120
SGRPRTEALP  YRLADGQWHR  VALSVSASHL  LLHIDCNRIY  ERVIDPPETN  LPPGSNLWLG  180
QRNQKHGLFK  GIIQDGKIIF  MPNGYITQCP  NLNRTCPTCS  DFLSLVQGIM  DLQELLAKMT  240
AKLNYAETRL  SQLENCHCEK  TCQVSGLLYR  DQDSWVDGDH  CRNCTCKSGA  VECRRMSCPP  300
LNCSPDSLPV  HIAGECCKVC  RPKCIYGGKV  LAEGQRILSK  SCQECRGGVL  VKITEACPLL  360
NCSEKDHILP  ENQCCSVCRG  HNFCAEGPKC  GENSECKNWN  TKATCECKNG  YISVQGDSAY  420
CEDIDECAAK  MHYCHANTVC  VNLPGLYRCD  CVPGYIRVDD  FSCTEHDDCG  SGQHNCDENA  480
ICTNTVQGHS  CTCKPGYVGN  GTICRGMPEV  GPPRALLNSL  DLGFLSFSKE  ALAVGMITLE  540
GNIVAKSFTD  DETLVERGRE  KVIALLFSWL  HKEKLSLENL  RDIYCKANSL  VGLDHLPQR   599
```

METHODS AND COMPOSITIONS FOR REGENERATING TISSUES

CROSS REFERENCED APPLICATIONS

This application is a continuation of U.S. patent application Ser. No. 17/333,406, filed May 28, 2021 and granted as U.S. Pat. No. 11,891,439, which is a divisional of U.S. patent application Ser. No. 16/813,376, filed Mar. 9, 2020 and granted as U.S. Pat. No. 11,034,741, which is a divisional of U.S. patent application Ser. No. 15/690,093, filed Aug. 29, 2017 and granted as U.S. Pat. No. 10,752,663, which claims the benefit of U.S. Provisional Application No. 62/380,920, filed Aug. 29, 2016, each of which is incorporated herein by reference in its entirety.

REFERENCE TO A SEQUENCE LISTING SUBMITTED ELECTRONICALLY AS AN XML FILE

The instant application contains a Sequence Listing which has been submitted in XML format via USPTO Patent Center and is hereby incorporated by reference in its entirety. Said XML copy, created on Apr. 30, 2024, is named N88509_1060US_D2C2_SL, and is 44.0 KB in size.

FIELD OF THE INVENTION

This application generally relates to the healing of injuries, including those involving tendons and/or ligaments, with a regenerative protein or a nucleic acid encoding the same.

BACKGROUND OF THE INVENTION

The healing of an injury involves a multistep process whereby injured tissue is repaired, specialized tissue is regenerated, and new tissue is reorganized into a functional unit. Wound healing is generally divided into the inflammatory phase, the proliferative phase, and the maturation and remodeling phase. An impairment in any one of these phases can lead to complications. Particular tissues can be more difficult to heal properly due in part to their cellular makeup, limited vasculature, and/or location in highly mobile parts of the body. Injuries to tendons and ligaments, for example, can be particularly challenging to properly heal.

Tendons are soft connective tissues that connect muscle to bone or cartilage, while ligaments connect bone to bone to hold the skeleton and stabilize the joints. They are composed primarily of packed collagen fibers that impart different mechanical properties based on the shape and how they are organized. There is very little cellularity in these tissues—mostly fibroblasts secreting the extracellular material (ECM). Ligaments have a lower collagen content (~75%) with a random pattern, while tendons have more collagen (80-90%) and are highly organized. The ECM of both tissues are composed of Types I and III collagen, with ligaments having a lesser proportion of Type I (90%) and more of type III (10%) in comparison to tendons which have 95-99% Type 1 and 1-5% Type III. Another key difference between these two types of connective tissue is the presence of elastin in ligaments, which is very minimal in tendons. (Lui (2015) *Stem Cells and Cloning: Advances and Applications* 8:163-174).

Considerable basic studies have been devoted to the understanding of the development, structure, and function of these important tissues, because traumatic tendon/ligament injuries are extremely difficult to heal completely. These injuries often result in permanent disability and chronic pain in human patients, while in veterinary animals such as horses or dogs, damage to key tendon and ligaments can adversely affect the quality of life so severely that euthanasia is necessary. Treating tendon/ligament injuries is clinically challenging in both human and veterinary medicine because of the innate poor tissue healing response, likely due to the primary characteristics of these soft tissues including: a) a low proportion of resident progenitor and stem cells; b) limited vasculature or blood vessel supply; and c) a tendency for persistent inflammation because these are located in highly mobile body parts. The constant motion of the injured sites can hinder healing. Even in cases where healing occurs, a fibrovascular scar is formed which does not possess the biomechanical and biochemical properties of normal/original tendon and/or ligament, thereby resulting in significant loss of function for the individual and increased re-injury rates. (Lui (2015); Ross (2014) *Stem Cell Discovery* 4:44-53)

The three most common tendon injuries in man are tearing of the rotator cuff, injuries to the hand flexor tendon, and injuries to the Achilles tendon. These are often treated by surgical repair, physical therapy/rehabilitation and cryotherapy. In 2004, it was estimated that 45% of 32 million musculoskeletal injuries involved tendons and ligaments, and that the incidence was rapidly rising due to increased sports activities and an aging population. (September et al. (2007) *Br J Sports Med* 41:241-246)

The most common tendon and/or ligament injuries in racehorses and performance horses affect the suspensory ligament running behind the cannon bone, and the superficial and deep digital flexor tendons (SDFT and DDFT) running behind the back of the knee (or hock) all the way down to the navicular bone in each foot, acting as a sling for the fetlock to bear weight. (Briggs (2011) *The Horse* Jun. 3, 2011, pp. 1-7). Injuries can be inflammation, sprains, strains, disruptions or tears and lacerations. Tendon/ligament injuries are estimated to be ~46% of all sport horse injuries, and 90% of tendon/ligament injuries are to the SDFT. SDFT damage is confirmed by a veterinarian with a physical exam for lameness and ultrasound. A horse can manifest lameness, heat, sensitivity to touch, tendon swelling or thickening, or a bowed or convex profile. Lameness correlates the degree of inflammation. (Tan (2016) *The Horse* Mar. 30, 2016, pp. 1-7). DDFT injuries are common in the hoof capsule and tendon sheath and are classified as tendon enlargements, changes in shape, focal core lesions, mineralization and marginal tears. Tears are best detected with ultrasound, MRI or tenoscopy.

Ligament injuries in horses are often proximal suspensory desmitis (PSD) in the limbs that result in acute lameness. Hind limb PSD occurs frequently in high-level dressage horses and is not very responsive to conservative therapy which consists of repeated bandaging, administration of anti-inflammatories and analgesics (only 14% return without lameness for less than one year).

The repair or regeneration of tendon/ligament injuries have been a consistent target of the increasing number of regenerative medicine technologies, such as stem cells, platelet rich plasma (PRP), bone marrow aspirate concentrate, growth factors, and bioengineered scaffolds. Techniques such as extracorporeal shock wave therapy, low level laser therapy and mechanical stimulation have also been employed. (Thomas (2005) *The Chronicle of the Horse* 134-137; Fortier and Smith (2008) *Vet Clin Equine* 24:191-201; Briggs (2011); Yang et al. (2013) *Birth Defects Res C*

*Embryo Today* 99(3):203-222; Lui (2015); Tan (2016); Basetto et al. (2011) Biomaterials Science and Engineering, Ch. 18, Ed. R. Pignatello, InTech, 2011, pp. 369-386) More effective treatments to restore or regenerate tendon/ligament tissues after injury are needed.

SUMMARY OF THE INVENTION

Compositions comprising a variant NELL1 peptide or a nucleic acid encoding the same are provided. The variant NELL1 peptide lacks at least one of the carboxy-terminal von Willebrand factor, type C (VWC) domains of a NELL1 protein. In some embodiments of the invention, the variant NELL1 peptide lacks both carboxy-terminal VWC domains. In some of these embodiments, the variant NELL1 peptide lacks the carboxy-terminal 179 amino acid residues. In particular aspects of the invention, the variant NELL1 peptide has at least 75% sequence identity to the disclosed SEQ ID NO: 17 or 18 and one of the following properties: enhanced efficacy in tissue regeneration, promotion of wound healing, easier purification, higher yield, and less aggregate formation, when compared to a full-length NELL1 protein. In some of these embodiments, the variant NELL1 peptide comprises or consists essentially of SEQ ID NO: 17 or 18. Also provided herein are pharmaceutical compositions and kits comprising the variant NELL1 peptide or a nucleic acid encoding the same.

The variant NELL1 peptides or nucleic acids encoding the same find use in regenerating injured tissues, promoting the maturation of a progenitor cell, enhancing the migration and/or proliferation of fibroblast cells, and promoting the healing of a wound, such as an injury to a tendon or a ligament. In particular aspects of the invention, the wound is an open wound. In certain embodiments, the wound comprises an injury to skeletal muscle, cartilage, bone, skin, tendon, ligament or a combination thereof. In some aspects, the variant NELL1 peptide or nucleic acid encoding the same is administered locally to the wound. In particular embodiments, the subject in need of promotion of healing of a wound is a mammal, such as a human or a horse. The variant NELL1 peptide or nucleic acid encoding the same can be administered to the wound about two days after the injury.

Methods for promoting the healing of an injury to a tendon or ligament in a subject in need thereof are provided herein. These presently disclosed methods involve the administration of an effective amount of a NELL1 peptide or a nucleic acid encoding a NELL1 peptide to the subject. The subject can be a mammal, such as a human or a horse. The methods find use in treating various injuries in humans, including injuries to Achilles tendons. Horses, especially racehorses, are particularly prone to tendon and ligament injuries, such as the superficial digital flexor tendon or deep digital flexor tendon, and the presently disclosed methods are useful in promoting the healing of these injuries. The NELL1 peptide or nucleic acid encoding the same can be administered via local injection to the area surrounding the injured tendon or ligament or can be incorporated into a matrix, such as a wound dressing and applied directly to the injured tissue. The NELL1 peptide or nucleic acid encoding the same can be administered to the tendon or ligament injury about seven days after the injury.

Methods for enhancing the migration and/or proliferation of fibroblast cells with a NELL1 peptide or a nucleic acid encoding the same are also provided herein. In particular aspects of the invention, the fibroblast cell is a dermal fibroblast or a ligament fibroblast. In some embodiments, the migration of the fibroblasts towards a wound area is enhanced with a NELL1 peptide or a nucleic acid encoding the same.

The foregoing is a summary and thus contains, by necessity, simplifications, generalizations, and omissions of detail; consequently, those skilled in the art will appreciate that the summary is illustrative and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

FIGS. 2A and 2B) and horse NEL1 variant protein aa3-612 (FIGS. 2C and 2D). FIGS. 2A and 2C depict sodium dodecyl sulfate polyacrylamide gel electrophoresis (SDS-PAGE), whereas FIGS. 2B and 2D depict Western Blots using mouse anti-GST antibody (1 µg/ml) to the GST tag attached to the NELL1 protein, followed by Jackson anti-mouse IgG-HRP (1500×). The lanes in FIG. 2A are as follows: M=molecular markers (kilodaltons or kDa) 10 µl/lane; lane 1=NELL1 protein aa3-791 (5 µl/lane); and lanes 2-5 are loading control proteins at 0.1 µg/lane, 0.2 µg/lane, 0.5 µg/lane, and 1.0 µg/lane, respectively. The lanes in FIG. 2B are as follows: M=molecular markers (kDa); lane 1 is NELL1 aa3-791 protein (5 µl); and lane 2 is GST protein. The lanes in FIG. 2C are as follows: M=molecular markers 10 µl/lane (kDa); lane 1=NELL1 protein aa3-612 (5 µl/lane); and lanes 2-5 are loading control proteins at 0.1 µg/lane, 0.2 µg/lane, 0.5 µg/lane, and 1.0 µg/lane, respectively. The lanes in FIG. 2D are as follows: M=molecular markers (kDa); lane 1 is NELL1 aa3-612 protein (5 µl); and lane 2 is GST protein.

FIG. 3A demonstrates a dose-dependent increase in wound healing on Type 1 diabetic human dermal fibroblasts in an in vitro wound scratch assay with Nell1 variant protein (aa3-612). There is increased migration of the diabetic dermal fibroblasts into the wound area when treated with 100 ng/ml (line b), 200 ng/ml (line c), and 300 ng/ml (line d) of the protein, compared to the untreated controls (line a). FIGS. 3B, 3C, and 3D demonstrates an increased wound healing effect on Type 1 diabetic human dermal fibroblasts, normal human dermal fibroblasts, and normal human ligament fibroblasts, respectively, in an in vitro wound scratch assay by 300 ng/ml of NELL1 variant protein (aa3-612; line C), compared to the full-length NELL1 protein at the same dose (line B) and the untreated control (line A).

DETAILED DESCRIPTION OF THE INVENTION

I. Introduction

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes and are not to be construed as limiting the subject matter described. Finally, for the purposes of the instant disclosure all identifying sequence Accession numbers may be found in the NCBI Reference Sequence (RefSeq) database and/or the NCBI GenBank archival sequence database unless otherwise noted.

II. NELL1

The neural epidermal growth-factor-like (nel) gene was first detected in neural tissue from an embryonic chicken cDNA library, and its human ortholog neural epidermal growth-factor-like 1 (NEL-like 1, NELL1) was discovered later in B-cells. Studies have reported the presence of NELL1 in various fetal and adult organs, including, but not limited to, skeletal and cardiac muscle, skin, the brain, kidneys, colon, thymus, lung, and small intestine.

The human NELL1 gene encodes an 810-amino acid polypeptide. Generally, the arrangement of the functional domains of the NELL1 protein bears resemblance to thrombospondin-1 (THBS1) and consists of a thrombospondin N-terminal domain (TSPN) and several von Willebrand factor, type C (VWC), and epidermal growth-factor (EGF) domains. A domain is a region of a protein with a characteristic primary structure and function.

Additional studies have shown that there are at least two human NELL1 transcript variants encoding different isoforms. In humans, the nel-like 1 isoform 1 precursor transcript variant (set forth in SEQ ID NO: 1) represents the longer transcript (set forth in GenBank Acc. No. NM_006157) and encodes the longer isoform 1 (set forth in SEQ ID NO: 2).

Figure 1:
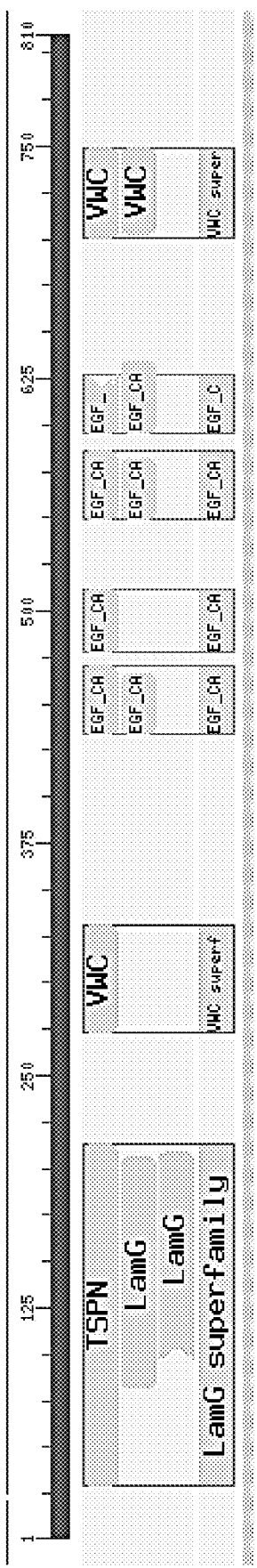
FIG. 1 shows the general structure of the human nel-like 1 isoform 1 (SEQ ID NO: 2).
Figures 2A, 2B:
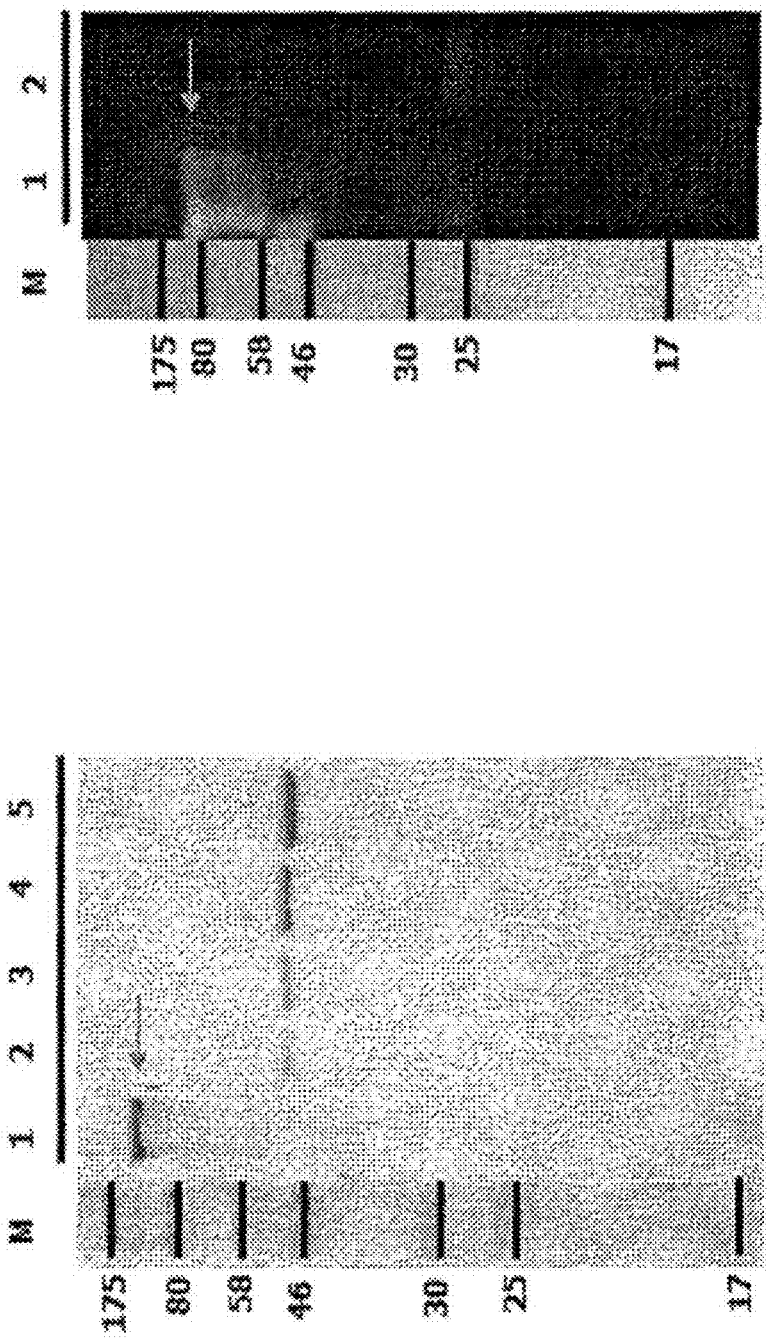
FIGS. 2A-2D depict purified recombinant horse NELL1 protein aa3-791 (full-length.
Figure 2C:
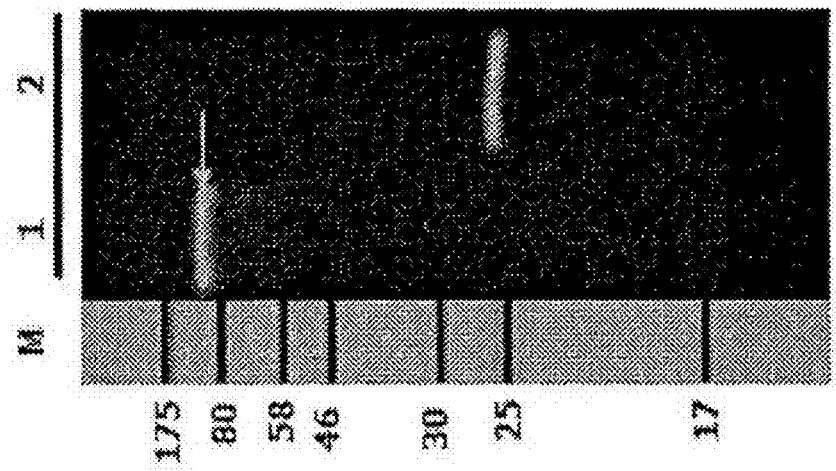
Figure 2D:
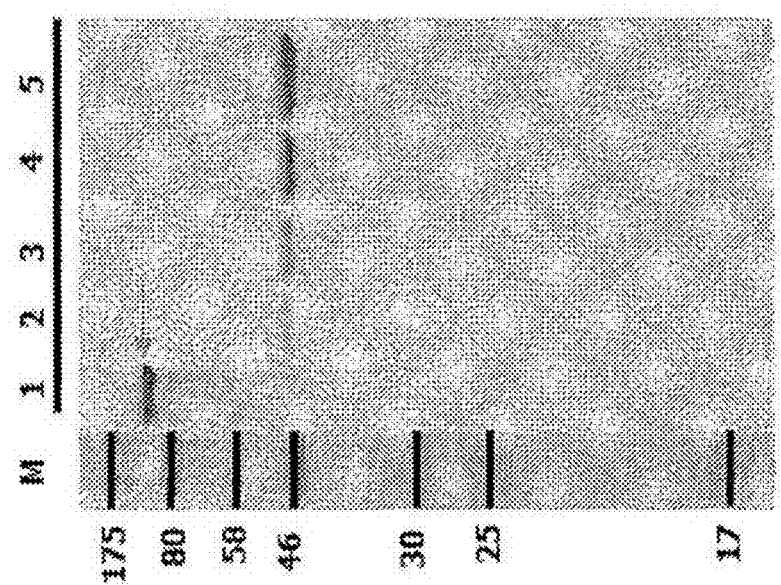

FIG. 1 shows the general structure of human nel-like 1 isoform 1 (SEQ ID NO: 2). The conserved domains reside in seven regions of the isoform 1 peptide and include: (1) a TSPN domain/Laminin G superfamily domain; (2) a VWC domain; (3) four EGF-like domains; and (4) a VWC domain. NELL1 also comprises a secretion signal peptide domain (amino acid residues 1-16 of SEQ ID NO: 2) that is generally involved in transport of the protein outside cell organelles where it is processed for secretion outside the cell.

The first conserved domain region comprises amino acids (amino acids 29 to 213 of SEQ ID NO: 2) that are most similar to a thrombospondin N-terminal-like domain. Thrombospondins are a family of related, adhesive glycoproteins, which are synthesized, secreted and incorporated into the (ECM) of a variety of cells, including alpha granules of platelets following thrombin activation and endothelial cells. They interact with a number of blood coagulation factors and anticoagulant factors, and are involved in cell adhesion, platelet aggregation, cell proliferation, angiogenesis, tumor metastasis, vascular smooth muscle growth and tissue repair. The first conserved domain also comprises amino acids (amino acids 82 to 206; amino acids 98 to 209 of SEQ ID NO: 2) that are similar to a Laminin G-like domain. Laminin G-like (LamG) domains usually are $Ca^{2+}$ mediated receptors that can have binding sites for steroids, β1-integrins, heparin, sulfatides, fibulin-1, and α-dystroglycans. Proteins that contain LamG domains serve a variety of purposes, including signal transduction via cell-surface steroid receptors, adhesion, migration and differentiation through mediation of cell adhesion molecules.

Studies show that NELL1 signaling involves an integrin-related molecule and tyrosine kinases that are triggered by NELL1 binding to a NELL1 specific receptor and a subsequent formation of an extracellular complex. As thus far understood, in human NELL1 (hNELL1), the laminin G domain comprises about 128 amino acid residues that show a high degree of similarity to the laminin G domain of extracellular matrix (ECM) proteins; such as human laminin α3 chain (hLAMA3), mouse laminin α3 chain (mLAMA3), human collagen 11 α3 chain (hCOLA1), and human thrombospondin-1 (hTSP1). This complex facilitates either activation of tyrosine kinases, inactivation of tyrosine phosphatases, or intracellular recruitment of tyrosine-phosphorylated proteins. The ligand bound integrin (cell surface receptors that interact with ECM proteins such as, for example, laminin 5, fibronectin, vitronectin, TSP1/2) transduces the signals through activation of the focal adhesion kinase (FAK) followed by indirect activation of the Ras-MAPK cascade, and then leads to osteogenic differentiation through Runx2; the laminin G domain is believed to play a role in the interaction between integrins and a 67 kDa laminin receptor (Shen et al. (2012) *J Cell Biochem* 113: 3620-3628).

The second conserved domain (amino acids 273 to 331 of SEQ ID NO: 2) and seventh conserved domain (amino acids 701 to 749 of SEQ ID NO: 2) are similar to von Willebrand factor type C (VWC) domains, also known as chordin-like repeats. An additional VWC domain is also found from amino acid residues 634 to 686 of SEQ ID NO: 2. VWC domains occur in numerous proteins of diverse functions and have been associated with facilitating protein oligomerization.

The third conserved domain (amino acids 434 to 466 of SEQ ID NO: 2), fourth conserved domain (amino acids 478 to 512 of SEQ ID NO: 2), fifth conserved domain (amino acids 549 to 586 of SEQ ID NO: 2), and sixth conserved domain (amino acids 596 to 627 of SEQ ID NO: 2) are similar to a calcium-binding EGF-like domain. Calcium-binding EGF-like domains are present in a large number of membrane-bound and extracellular (mostly animal) proteins. Many of these proteins require calcium for their biological function. Calcium-binding sites have been found to be located at the N-terminus of particular EGF-like domains, suggesting calcium-binding may be crucial for numerous protein-protein interactions. Six conserved core cysteines form three disulfide bridges as in non-calcium-binding EGF domains whose structures are very similar. The calcium-binding EGF-like domains of NELL1 bind protein kinase C beta, which is typically involved in cell signaling pathways in growth and differentiation.

The nel-like 1 isoform 2 precursor transcript variant (set forth in GenBank Acc. No. NM_201551 and SEQ ID NO: 3) lacks an alternate in-frame exon compared to variant 1. The resulting isoform 2 (set forth in SEQ ID NO: 4), which has the same N-and C-termini as isoform 1 but is shorter compared to isoform 1, has six conserved regions including a TSPN domain/LamG superfamily domain (amino acids 29 to 213 of SEQ ID NO: 4); VWC domains (amino acids 273 to 331 of SEQ ID NO: 4; amino acids 654 to 702 of SEQ ID NO: 4); and calcium-binding EGF-like domains (amino acids 478 to 512 of SEQ ID NO: 4; amino acids 434 to 466 of SEQ ID NO: 4; amino acids 549 to 580 of SEQ ID NO: 4).

NELL1 and its orthologs are found across several species including *Homo sapiens* (man), *Bos taurus* (cow; the nucleic acid sequence of which is set forth in GenBank Acc. No. XM_002699102 and the amino acid sequence is set forth in SEQ ID NO: 19), *Equus caballus* (horse; the nucleic acid sequence of isoforms 1 and 2 are set forth in GenBank Acc. Nos. XM_001504986 and XM_001504987, respectively, and in SEQ ID NO: 5 and 7, respectively; the amino acid sequences are set forth in SEQ ID NO: 6 and 8, respectively), *Macaca mulatta* (rhesus monkey; the nucleic acid sequence of isoforms 1, 2, 3, and 4 are set forth in GenBank Acc. Nos. XM_002799606, XM_001092428, XM_001092540, and XM_001092655, respectively), *Mus musculus* (mouse; the nucleic acid sequence of which is set forth in GenBank Acc. No. NM_001037906 and in SEQ ID NO: 9; the amino acid sequence of which is set forth in SEQ ID NO: 10), *Rattus norvegicus* (rat; the nucleic acid sequence of which is set forth in GenBank Acc. No. NM_031069 and in SEQ ID NO: 11; the amino acid sequence of which is set forth in SEQ ID NO: 12), *Pan troglodytes* (chimpanzee; the nucleic acid sequence of which is set forth in GenBank Acc. No. XM_508331.2), *Felis catus* (cat; the amino acid sequences of isoform 1 and 2 are set forth in GenBank Acc. Nos. XP_003993117.1 and XP_003993118.1, and SEQ ID NOs: 13 and 14, respectively, *Canis lupis familiaris* (dog; the amino acid sequence is set forth in GenBank Acc. No. XP_534090 and SEQ ID NO: 15), and *Ovis aries* (sheep; the amino acid sequence is set forth in GenBank Acc. No. XP_004019490 and SEQ ID NO: 16).

NELL1 is a signaling protein that mediates tissue growth and maturation in a variety of tissues such as bone, cartilage, heart and skeletal muscle—during fetal development and the healing of acute injuries in adult tissues (Desai et al. (2006) *Hum Mol Genet* 15(8): 1329-1341; Siu et al. (2011) *Tissue Eng Part A* 17(7-8): 1123-1135; Siu et al. (2012) *Tissue Eng Part A* 18(3-4):252-261; Xue et al. (2011) *Bone* 48(3):485-495; Li et al. (2011) *Plast Reconstr Surg* 127(2):580-587; Turner et al. (2013) *Cells Tissues and Organs* 198(4):249-265). During early development, NELL1 regulates the production of many components of the extracellular matrix (ECM) which collectively serve as an architectural framework and communication highway to mediate new tissue formation.

In vitro studies on three-dimensional human skin models exposed to UV radiation demonstrated that NELL1 reduces levels of key pro-inflammatory molecules (e.g. IL1-B, IL8) after adult tissue injury (Mitchell et al. (2012) Abstract, 70$^{th}$ Annual Meeting of the American Academy of Dermatology, San Diego, CA, March 16-20). Human genome-wide association studies have also suggested that in certain genetic populations NELL1 plays a role in controlling severe inflammatory conditions (Franke et al. (2007) *PLOS ONE* 2(8):e691).

Multiple effects of NELL1 are believed to contribute to its ability to heal injuries to tendons and/or ligaments. Such effects include its pro-angiogenic activity, which stimulates blood vessel formation in areas having poor blood supply. NELL1 accomplishes this via effects on VEGF and perivascular stem cells (Askarinam et al. (2013) *Tissue Eng A* 19(11-12):1386-1397). The effect of NELL1 in perivascular cells is particularly important in tendon regeneration because the capillaries of tendons contain perivascular stem cells that express tendon-and stem/precursor cell-like characteristics which could be the source of the formation/regeneration of new tendon tissue (Tempfer et al. (2009) *Histochem Cell Biol* 131(6):733-741). While not being held by any theory or mechanism of action, it is believed that NELL1 can also stimulate the proliferation and migration of tendon precursor stem cells, fibroblasts or perivascular stem cells, contributing to the healing of tendons (Nemoto et al. (2013) *J Equine Sci* 24(2): 17-24).

NELL1 induces the production of molecules in the extracellular matrix that are key structural components of tendons and ligaments or molecules that regulate the production of components and their assembly/organization into the correct functional architecture. Some of the known genes in the NELL1 pathway directly impact tendon or ligament development, structure, function, repair and regeneration after injuries. This list includes tenascin C, collagen V, Bmp7, periostin or osteoblast specific factor 2, and Prg4 (lubricin). Tenascin C is a glycoprotein abundant in tissues with high tensile strength and subject to compression stress. It is believed to be a key factor in tendon healing due to its ability to promote fibroblast/tendon cell proliferation and migration. Tenascin C is a genetic determinant of Achilles heel tendinopathies and ruptures and is linked to tissue response to mechanical loading, probably by regulating cell-ECM interactions (September et al. (2007); Taylor et al. (2009) *BMC Musculoskeletal Disorders* 10(27):1-10; Juneja & Veillette (2013) *Arthritis* 2013:1-30; Nemoto et al. (2013)). Collagen V, specifically Col5a1 and Col5a3, is a component of fibrillary collagen that regulates collagen fiber assembly and diameter in tendons and ligaments (September et al. (2007); Connizzo et al. (2015) *J Orthopaedic Research* 33:882-888; Sun et al. (2015) *Am J Pathol* 185:1436-1447). Bmp7 is a bone morphogenetic protein that serves as a growth factor promoting cell growth and differentiation. It facilitates tendon-bone integration. Other studies show it increases collagen type 1 production and cell activity (Pauly et al. (2012) *J Shoulder Elbow Surg* 21(4):464-473; Schwarting et al. (2015) *PLOS One* 10(2):1-17). Periostin or osteoblast specific factor 2 is a matricellular protein that is abundant in collagen rich connective tissue, where it is essential for proper ECM synthesis, collagen 1 fibrillogenesis, and tendon crosslinking. (Hamilton et al. (2008) *J Cell Commun Signal* 2:9-17; Juneja & Veilette (2013)). Prg4 (lubricin) is a proteoglycan that plays a role in boundary lubrication in articulating joints and tendon gliding. Its absence leads to decreased lubrication, which causes tissue damage, matrix remodeling and dystrophic calcification. (Juneja & Veillete (2013)). NELL1 modulates the inflammatory response via the downregulation of cytokines such as IL-1 beta and IL8 (Mitchell et al. (2012)). Tendon and ligament injuries are prone to prolonged inflammation because the injured sites are often subjected to constant motion. NELL1 downregulates matrix metalloproteinases (e.g. MMP1), which degrade the collagen in tendon ECM.

MMPs are needed to maintain ECM homeostasis, but tendon injury can lead to an imbalance or dysregulation so that high levels can further degrade tendon architecture and function. (Mitchell et al. (2012); Davis et al. (2013) *J Applied Physiol* 115(6):884-891).

Disclosed herein is the discovery that NELL1 also enhances the migration and/or the proliferation of fibroblast cells (e.g., ligament fibroblasts, dermal fibroblasts from normal individuals and type 1 diabetic patients). This effect can serve to promote wound healing by increasing the numbers of fibroblasts within a wound area, thus enhancing the contraction and closure of the wound. The proliferation and migration of fibroblasts into the provisional wound matrix/fibrin clot are critical processes that are triggered early in wound healing (e.g., few days after injury in human skin) and have significant roles in supporting other biological processes throughout normal wound healing, including the degradation of the fibrin clot, secretion of new extracellular matrix and collagen-rich structures to support the activities of other cells, and wound contraction. The presently disclosed methods and compositions utilize a NELL1 peptide or a nucleic acid molecule encoding the same to promote the healing of injuries to tendons or ligaments or to enhance the migration and/or proliferation of fibroblasts. Certain NELL1 variants also find broader use in regenerating tissues, promoting healing of wounds, and promoting the maturation of progenitor cells.

A peptide, polypeptide, or protein is a sequence of subunit amino acids, amino acid analogs, or peptidomimetics. A peptidomimetic is a small protein-like chain designed to mimic a peptide. A peptidomimetic typically arises from modification of an existing peptide in order to alter the molecule's properties.

A peptide, polypeptide or protein can also be amino acid polymers in which one or more amino acid residue is an artificial chemical analogue of a corresponding naturally occurring amino acid, as well as to naturally-occurring amino acid polymers. A polypeptide, peptide or protein is inclusive of modifications including, but not limited to, glycosylation, lipid attachment, sulfation, gamma-carboxylation of glutamic acid residues, hydroxylation, phosphorylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing events and events brought about by human manipulation which do not occur naturally. Circular, branched and branched circular polypeptides may be synthesized by non-translation natural processes and by entirely synthetic methods, as well.

A NELL1 peptide, NELL1 polypeptide, or NELL1 protein is a naturally-occurring NELL1 protein, or a variant or fragment thereof that retains the ability to promote the healing of injuries to tendons and/or ligaments. In some embodiments, the NELL1 peptide exhibits any one of the activities selected from the group consisting of: stimulation of ECM production (e.g., through the upregulation of at least one of tenascins, proteoglycans, elastin, glycosaminoglycans, including epidermal hyaluronic acid, and collagens), reduction in the levels of inflammatory mediators (e.g., IL-1β and IL-8), reduction in the levels of matrix metalloproteinases (e.g., MMP1), and enhancing the migration and/or proliferation of fibroblasts. In other embodiments, the NELL1 peptide can also exhibit at least one of the activities selected from the group consisting of: binding to PKC-beta, stimulation of differentiation of a precursor cell (e.g., skeletal satellite cell, osteoblast precursor, perivascular stem cell, or tendon precursor stem cell) to maturity, and stimulation of angiogenesis. To determine whether a peptide exhibits any one of these activities, any method known in the art useful for measuring these activities can be used.

Suitable assays for determining if a given peptide can stimulate ECM production and reduce the levels of inflammatory mediators or MMPs include assays that measure transcript levels (e.g., quantitative polymerase chain reaction) or levels of the protein (e.g., enzyme-linked immunoassay) directly or indirectly (by measuring the activity of the protein), including those that are described elsewhere herein.

Suitable assays for assessing the binding of NELL1 to PKC beta is described in e.g., Kuroda et al. (1999) *Biochem Biophys Res Comm* 265:752-757. For example, protein-protein interactions can be analyzed by using the yeast two-hybrid system. Briefly, a NELL1 protein can be fused with GAL4 activating domain and the regulatory domain of PKC can be fused with the GAL4 DNA-binding domain.

In other embodiments, the NELL1 peptide stimulates the differentiation of precursor cells, such as skeletal satellite cells, osteoblast precursors, perivascular stem cells, and tendon precursor stem cells, to maturity. The maturity of cells can be assessed cellularly (histology) and molecularly (expression of cell-specific proteins or extracellular matrix materials).

Suitable assays for determining if a peptide is capable of promoting the healing of tendon and/or ligament injuries include those known in the art (Nemoto et al. (2013); Taylor et al. (2009); Yanming et al. (2007) *Nature Medicine* 13:1219-1227; Tempfer et al. (2009)) and disclosed elsewhere herein.

Suitable assays for determining if a NELL1 peptide can promote the migration and/or proliferation of fibroblasts include wound scratch assays known in the art and described elsewhere herein.

The NELL1 peptide may be a naturally-occurring (i.e., wild-type) NELL1 protein or an active variant or fragment thereof. Naturally refers to as found in nature; wild-type; innately or inherently. A naturally-occurring NELL1 peptide may be purified from a natural source or may be a peptide that has been recombinantly or synthetically produced that has the same amino acid sequence as a NELL1 peptide found in nature.

A polynucleotide can be a singular nucleic acid, as well as plural nucleic acids, and refers to a nucleic acid molecule or construct, e.g., messenger RNA (mRNA), complementary DNA (cDNA), plasmid DNA (pDNA), or short interfering RNA (siRNA). A polynucleotide can be single-stranded or double-stranded, linear or circular and can be comprised of DNA, RNA, or a combination thereof. A polynucleotide can comprise a conventional phosphodiester bond or a non-conventional bond (e.g., an amide bond, such as found in peptide nucleic acids (PNA)). A nucleic acid can be any one or more nucleic acid segments, e.g., DNA or RNA fragments, present in a polynucleotide. The polynucleotide can contain modified nucleic acids, such as phosphorothioate, phosphate, ring atom modified derivatives, and the like. The polynucleotide can be a naturally occurring polynucleotide (i.e., one existing in nature without human intervention), a recombinant polynucleotide (i.e., one existing with human intervention), or a synthetically derived polynucleotide.

An isolated material can refer to a nucleic acid, peptide, polypeptide, or protein, which is: (1) substantially or essentially free from components that normally accompany or interact with it as found in its naturally occurring environment. Substantially free or essentially free refer to considerably or significantly free of, or more than about 95% free of, or more than about 99% free of. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868, each of which is incorporated by reference herein. Likewise, a naturally occurring nucleic acid (for example, a promoter) becomes isolated if it is introduced by non-naturally occurring means to a locus of the genome not native to that nucleic acid.

Fragments and variants of native (i.e., naturally-occurring) NELL polypeptides can be employed in the various methods and compositions of the invention. A fragment is intended a portion of a polynucleotide or a portion of a polypeptide. Fragments of a polynucleotide may encode polypeptide fragments that retain the biological activity of the native polypeptide. A fragment of a polynucleotide that encodes a biologically active portion of a NELL1 polypeptide will encode at least 15, 25, 30, 50, 100, 150, 200, 250, 300, 350, 400, 450, 500, 550, 600, 650, 700, 750, or 800 contiguous amino acids, or up to the total number of amino acids present in a full-length NELL1 polypeptide. In certain embodiments, the NELL1 fragment is 610 amino acids in length.

A fragment of a native NELL1 polypeptide can be prepared by isolating a portion of a polynucleotide encoding the portion of the NELL1 polypeptide and expressing the encoded portion of the polypeptide (e.g., by recombinant expression in vitro). Polynucleotides that encode fragments of a NELL1 polypeptide can comprise nucleotide sequences comprising at least 15, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, or 2400 contiguous nucleotides, or up to the number of nucleotides present in a full-length NELL1 nucleotide sequence. In some embodiments, the fragment lacks the first amino acid residue, or the first 2, 3, 4, 5, 6, 7, 8, 9, 10, 20, 21, 22, 23, 24, 25, 26, 27, 28, 29, 30, 35, 40, or 45 amino acid residues from the amino terminal end of the NELL1 protein. In some embodiments, the fragment lacks the last 5, 10, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 220, 230, 240, 250, 260 or more amino acid residues. In certain embodiments, the fragment of a NELL1 protein lacks the most carboxy-terminal 179 amino acid residues from the end of the protein. In other embodiments, the NELL1 protein fragment lacks the first two amino acid residues from the amino terminal end and the last 179 amino acid residues from the carboxy terminal end of the protein. In some embodiments, the NELL1 protein fragment has 610 amino acid residues.

The inventors determined that removal of 179 amino acid residues from the carboxy-terminus of the *Equus caballus* NELL1 isoform 1 protein unexpectedly provided a higher yield and easier purification during manufacture of the protein. Without being bound by any theory or mechanism of action, it is believed that the removal of the carboxy-terminal domains led to decreased formation of aggregates of the protein. Although NELL1 protein naturally oligomerizes into trimers, which are functional, aggregates of NELL1 protein refer to large, higher-ordered macromolecular complexes that prevent or reduce the function of the protein or make the protein products difficult to extract and purify. The NELL1 protein lacking the C-terminal 179 amino acid residues is also unexpectedly more efficacious than full-length NELL1 protein in horse body wound healing studies and fibroblast wound scratch assays. Thus, in specific embodiments, the NELL1 protein fragment lacks the last 179 amino acid residues from the carboxy terminus. In some of these embodiments, the NELL1 protein fragment also lacks the first two amino acid residues from the amino terminus. The sequence of this horse NELL1 fragment is set forth in SEQ ID NO: 18. In other embodiments, the NELL1 protein fragment lacks the first 21 amino acid residues from the amino terminus and the last 179 amino acid residues from the carboxy terminus. The sequence of this human NELL1 fragment is set forth in SEQ ID NO: 17. In certain embodiments, the NELL1 protein fragment lacks at least one of the two carboxy-terminal VWC domains (located at amino acid residues 634-686 and 701-749 of SEQ ID NO: 2). In some of these embodiments, the NELL1 protein fragment lacks both of these carboxy-terminal VWC domains. Compositions comprising these NELL1 fragments are contemplated herein and methods for using these NELL1 fragments for regenerating tissues (e.g., bone, cartilage, heart, vasculature, skeletal muscle), promoting the maturation of progenitor cells for various tissues (e.g., bone, cartilage, heart, vasculature, skeletal muscle, tendons, ligaments), and promoting the migration and/or proliferation of fibroblasts are also contemplated herein.

In those embodiments wherein a variant NELL1 protein lacks at least one C-terminal VWC domain, the variant NELL1 protein exhibits at least one of the following characteristics: enhanced efficacy in tissue regeneration and/or promotion of wound healing, easier purification, higher yield, less aggregate formation, and enhanced efficacy in fibroblast migration and/or proliferation, when compared to a full-length NELL1 protein. An easier purification includes a purification process whereby a single polypeptide species is substantially separated from other polypeptide species or a natural or synthetic milieu comprising the single polypeptide species and other polypeptide species that comprises fewer steps required for substantial separation or wherein the time required for at least one of the steps in the separation is reduced. An easier purification also refers to a purification process which results in a higher yield of the substantially purified or separated polypeptide species. The terms "substantially purified" or "substantially separated" when used in reference to a single polypeptide species refers to a level of purification whereby the single polypeptide species represents at least about 70% of a total population of polypeptide species within a sample, including but not limited to at least about 75%, 80%, 85%, 86%, 87%, 88%, 89%, 90%, 91%, 92%, 93%, 94%, 95%, 96%, 97%, 98%, 99%, or greater of a total population of polypeptide species within a sample. A yield of a protein product from a purification process refers to the overall concentration of the polypeptide within a solution. The higher the concentration of the polypeptide within the solution, the more yield is obtained. If a polypeptide is present within a solution at <0.1

µg/µl, the protein is considered difficult to produce and purify. Thus, in some embodiments, a variant NELL1 protein that lacks at least one C-terminal VWC domain exhibits the ability to be purified using conventional purification means known in the art, such as those methods described elsewhere herein, to a concentration greater than 0.1 µg/µl. In some of these embodiments, a variant NELL1 protein has the ability to be purified using conventional purification means known in the art to a concentration of about 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30 µg/µl, or greater. In certain embodiments, a variant NELL1 protein lacking at least one C-terminal VWC domain exhibits both a higher yield and a greater purity as compared to a full-length NELL1 protein following a purification process.

Variant sequences have a high degree of sequence similarity. For polynucleotides, conservative variants include those sequences that, because of the degeneracy of the genetic code, encode the amino acid sequence of a NELL1 polypeptide. Variants such as these can be identified with the use of well-known molecular biology techniques, such as, for example, polymerase chain reaction (PCR) and hybridization techniques. Variant polynucleotides also include synthetically derived nucleotide sequences, such as those generated, for example, by using site-directed mutagenesis. In some embodiments, the variant polynucleotide still encodes a NELL1 polypeptide or a fragment thereof. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide can also be evaluated by comparison of the percent sequence identity between the polypeptide encoded by a variant polynucleotide and the polypeptide encoded by the reference polynucleotide. Thus, variants include, for example, polynucleotides that encode a polypeptide with a given percent sequence identity to a native NELL1 polypeptide. Percent sequence identity between any two polypeptides can be calculated using sequence alignment programs and parameters described herein. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

A variant polypeptide is a polypeptide derived from the native polypeptide by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. The activity of variant NELL1 polypeptides can be assessed using the methods disclosed herein to determine if the variant is biologically active. Such variants may result from, for example, genetic polymorphism or from human manipulation. Biologically active variants of a native NELL1 polypeptide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native polypeptide as determined by sequence alignment programs and parameters described elsewhere herein. A biologically active variant of a polypeptide may differ from that polypeptide by as few as 1-15 amino acid residues, as few as 1-10, such as 6-10, as few as 5, as few as 4, 3, 2, or even 1 amino acid residue.

Biologically active variants of the NELL1 fragments disclosed herein (i.e., those lacking at least one of the two VWC domains at the carboxy terminus of NELL1) are also contemplated herein and may have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the active NELL1 fragment (e.g., SEQ ID NO: 17 or 18).

Polypeptides may be altered in various ways including amino acid substitutions, deletions, truncations, and insertions. Methods for such manipulations are generally known in the art. For example, amino acid sequence variants of native NELL1 polypeptides can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the polypeptide of interest may be found in the model of Dayhoff et al. (1978) *Atlas of Protein Sequence and Structure* (Natl. Biomed. Res. Found., Washington, D.C.). Conservative substitutions, such as exchanging one amino acid with another having similar properties, may be preferable.

Generally, the mutations made in the polynucleotide encoding the variant NELL1 polypeptide should not place the sequence out of reading frame, and/or create complementary regions that could produce secondary mRNA structure. Sec, EP Patent Application Publication No. 75,444.

Variant NELL1 polynucleotides and polypeptides also encompass sequences and polypeptides derived from a mutagenic and recombinogenic procedure such as DNA shuffling. With such a procedure, one or more different NELL1 coding sequences can be manipulated to create peptides that can be evaluated to determine if it retains NELL1 activity. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Variant NELL1 polynucleotides and polypeptides also encompass sequences and polypeptides derived from gene editing systems, such as CRISPR/Cas system.

Sequence identity in the context of two polynucleotides or polypeptide sequences makes reference to the residues in the two sequences that are the same when aligned for maximum correspondence over a specified comparison window. When percentage of sequence identity is used in reference to polypeptides it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have sequence similarity or similarity. Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

Percentage of sequence identity is the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3; % identity and % similarity for an amino acid sequence using GAP Weight of 8 and Length Weight of 2, and the BLOSUM62 scoring matrix; or any equivalent program thereof. An equivalent program is any sequence comparison program that, for any two sequences in question, generates an alignment having identical nucleotide or amino acid residue matches and an identical percent sequence identity when compared to the corresponding alignment generated by GAP Version 10.

The NELL1 peptide may be made synthetically, i.e. from individual amino acids, or semi-synthetically, i.e. from oligopeptide units or a combination of oligopeptide units and individual amino acids. Suitable methods for synthesizing proteins are described by Stuart and Young in "*Solid Phase Peptide Synthesis,*" Second Edition, Pierce Chemical Company (1984), *Solid Phase Peptide Synthesis, Methods Enzymol.,* 289, Academic Press, Inc, New York (1997).

The NELL1 peptide may also be prepared by methods that are well known in the art. One such method includes isolating or synthesizing DNA encoding the NELL1 peptide, and producing the recombinant protein by expressing the DNA, optionally in a recombinant vector, in a suitable host cell. Suitable methods for synthesizing DNA are described by Caruthers et al. (1985) *Science* 230:281-285; and *DNA Structure, Part A: Synthesis and Physical Analysis of DNA,* Lilley, D. M. J. and Dahlberg, J. E. (Eds.), *Methods Enzymol.,* 211, Academic Press, Inc., New York (1992).

In some embodiments of the presently disclosed methods, a nucleic acid molecule encoding a NELL1 peptide is administered to a subject in need thereof in order to regenerate tissue, promote the healing of an injury (e.g., tendon or ligament injury), or to enhance migration and/or proliferation of fibroblasts. As used herein, the terms "encoding" or "encoded" when used in the context of a specified nucleic acid mean that the nucleic acid comprises the requisite information to direct translation of the nucleotide sequence into a specified polypeptide.

In some embodiments of the presently disclosed methods, the NELL1 nucleic acid molecule is operably linked to at least one regulatory element. A regulatory element is a nucleic acid sequence(s) capable of effecting the expression of nucleic acid(s), or the peptide or protein product thereof. Non-limiting examples of regulatory elements include promoters, enhancers, polyadenylation signals, transcription or translation termination signals, ribosome binding sites, or other segments of DNA where regulatory proteins, such as, but not limited to, transcription factors, bind preferentially to control gene expression and thus protein expression.

Regulatory elements may be operably linked to the nucleic acids, peptides, or proteins of the described invention. When two or more elements are operably linked, there exists a a functional linkage between the elements. For example, when a promoter and a protein coding sequence are operably linked, the promoter sequence initiates and mediates transcription of the protein coding sequence. The regulatory elements need not be contiguous with the nucleic acids, peptides, or proteins whose expression they control as long as they function to direct the expression thereof. Thus, for example, intervening untranslated yet transcribed sequences may be present between a promoter sequence and a nucleic acid of the described invention and the promoter sequence may still be considered operably linked to the coding sequence.

In certain embodiments, the NELL1 nucleic acid molecule is a recombinant expression cassette or is part of an expression system. The term "recombinant expression cassette" refers to a nucleic acid construct, generated recombinantly or synthetically, with a series of specified nucleic acid elements which permit transcription of a particular nucleic acid (e.g., protein coding sequence) in a host cell. The recombinant expression cassette can be incorporated into a plasmid, chromosome, mitochondrial DNA, virus, or nucleic acid fragment. Typically, the recombinant expression cassette portion of an expression vector includes, among other sequences, a nucleic acid to be transcribed, a promoter, and a transcription termination signal such as a poly-A signal.

The expression cassette or cloning vector can be generated using molecular biology techniques known in the art and utilizing restriction enzymes, ligases, recombinases, and nucleic acid amplification techniques such as polymerase chain reaction that can be coupled with reverse transcription.

In some embodiments, the NELL1 protein is produced using a cell-free expression system such as the wheat germ in vitro translation system.

In some embodiments, the NELL1 nucleic acid molecule is in a host cell that can be used for propagation of the nucleic acid molecule or for expression of the NELL1 peptide and subsequent isolation and/or purification. A host cell is any cell that contains a heterologous nucleic acid molecule. A heterologous polypeptide or nucleotide sequence is a polypeptide or a sequence that originates from a different species, or if from the same species, is substantially modified from its native form in composition and/or genomic locus by deliberate human intervention. The host cell typically supports the replication and/or expression of the vector. Host cells may be prokaryotic cells such as, but not limited to, *Escherichia coli,* or eukaryotic cells such as, but not limited to, yeast, insect, amphibian, plant (e.g., *Nicotiana tabacum* (tobacco), *Oryza sativa* (rice), *Arabidopsis thaliana* (cress)), or mammalian cells. The term as used herein means any cell which may exist in culture or in vivo as part of a unicellular organism, part of a multicellular organism, or a fused or engineered cell culture. A cloning host cell is a host cell that contains a cloning vector.

A recombinant cell or vector is one that has been modified by the introduction of a heterologous nucleic acid or the cell that is derived from a cell so modified. Recombinant cells express genes that are not found in identical form within the native (non-recombinant) form of the cell or express native genes that are otherwise abnormally expressed, under-expressed or not expressed at all as a result of deliberate human intervention. The alteration of a cell or vector by naturally occurring events (e.g., spontaneous mutation, natural transformation transduction/transposition), such as those occurring without deliberate human intervention, does not result in a recombinant cell or vector.

The NELL1 nucleic acid molecule can be introduced into a host cell for propagation of production of NELL1 using any method known in the art, including transfection, transformation, or transduction, so long as the nucleic acid molecule gains access to the interior of the cell. The insertion or introduction of a nucleic acid into a cell refers to transfection or transformation or transduction and includes the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The NELL1 nucleic acid molecule can be introduced to allow for stable transformation or transient transformation. Stable transformation is intended to mean that the nucleotide construct introduced into a cell integrates into a genome of the cell. Transient transformation is intended to mean that a polynucleotide is introduced into the cell and does not integrate into a genome of the cell.

The NELL1 protein can be administered by a cell based gene therapy. For example, autologous, allogeneic or xenogeneic donor cells are genetically modified in vitro to express and secrete NELL1 protein. The genetically modified donor cells are then subsequently implanted into the subject in need of delivery of NELL1 protein in vivo. Examples of suitable cells include, but are not limited to, tenocytes, endothelial cells, fibroblasts (including tendon-derived fibroblasts), or stem/precursor cells, such as adult stem cells, embryonic stem cells, cord blood stem cells, perivascular stem cells, or tendon/stem progenitor cells (TSPCs).

III. Methods

The presently disclosed methods involve the regeneration of tissue, promotion of healing of an injury (e.g., tendon or ligament injury), or the enhancement of fibroblast migration and/or proliferation in a subject in need thereof. NELL1 peptides also find use in enhancing fibroblast migration and/or proliferation in an in vitro or ex vivo setting, for example in a wound scratch assay.

The regeneration of tissue refers to the process of renewal and growth of cells and extracellular matrix components within a particular tissue that results in the production of tissue that has a cellular component and architecture that allows for the normal functions of the particular tissue type. As described elsewhere herein, NELL1 has been demonstrated to stimulate the regeneration of tissues such as bone, cartilage, and skeletal muscle, which is believed to be attributed to at least one of the following effects of NELL1 protein: stimulation of the differentiation of precursor cells to maturity, pro-angiogenic activity, stimulation of ECM production, and reduction in levels of MMPs and inflammatory mediators. As disclosed herein, NELL1 also enhances the migration and/or proliferation of fibroblast cells, which can also contribute to tissue regeneration, particularly in response to a wound or within an area of injury.

As disclosed herein, the administration of NELL1 to fibroblast cells results in an increased migration rate and greater cell numbers within an area of tissue injury. The greater cell numbers can be a result of an enhanced migration rate and/or an increase in proliferation of the fibroblasts. Thus, a NELL1 protein can enhance the migration and/or proliferation of fibroblast cells. An enhancement of fibroblast migration refers to an increase in the rate of movement of fibroblasts from one region to another, for example, chemotactic movement towards a chemical signal or movement towards an area of injury (i.e., a wound). Thus, NELL1 proteins find use in methods of enhancing the migration and/or proliferation of fibroblast cells, in vivo or in vitro. In vitro settings in which NELL1 proteins can enhance the migration and/or proliferation of fibroblast cells include wound scratch assays whereby a confluent or substantially confluent layer of fibroblast cells grown in culture are disturbed through the introduction of a "scratch" or removal of a portion of the fibroblast monolayer, followed by a period of culturing the cells such that the fibroblasts begin to repopulate the "wounded" area either through migration of the fibroblasts into the wounded area or proliferation of the fibroblasts, or a combination of the two.

The promotion of the healing of a wound refers to an increase in the speed with which an injury (i.e., wound) heals or an improved outcome. Healing of an injury is considered to be promoted, for example, if the time of healing of an injury treated with NELL1 compared to an injury not treated with NELL1 is decreased by about 10%, about 25%, about 50%, or about 75%. Alternatively, healing of an injury is considered to be promoted if the extent of re-acquisition of tendon and/or ligament function of an injury treated with NELL1 compared to an injury not treated with NELL1 is improved by about 10%, about 25%, about 50%, or about 75%. Conversely, healing of an injury is considered to be promoted if the degree and/or amount of scar tissue resulting from an injury treated with NELL1 as compared to an injury not treated with NELL1 is reduced by about 10%, about 25%, about 50%, or about 75%. Promotion of healing of an injury to a tendon or ligament can also be considered if there is an improvement in the composition (e.g., proportion and amount of collagen types) and/or architecture (e.g., correct alignment of collagen fibrils/fibers/bundles) of at least about 10%, about 25%, about 50%, or about 75% of an injury treated with NELL1 compared to an injury not treated with NELL1.

The NELL1 peptide or nucleic acid molecule encoding the same is administered to a subject in need thereof to regenerate tissue, particularly to promote healing of an injury (e.g., a tendon and/or ligament injury), or to enhance the migration and/or proliferation of fibroblasts (e.g., dermal fibroblasts, ligament fibroblasts). The terms "subject", "individual", and "patient" are used interchangeably to refer to a member of a species that comprises tendons and ligaments. In certain embodiments, the subject is a mammal, including but not limited to, mouse, rat, cat, goat, sheep, horse, hamster, ferret, pig, dog, platypus, guinea pig, rabbit and a primate, such as, for example, a monkey, ape, or human. In some of these embodiments, the subject is a human or a horse, such as a racehorse. Subjects in need of treatment with a NELL1 peptide or nucleic acid molecule include those having an injury or those that are prone to injuries or an impaired healing process. Subjects that are prone to the development of injuries to a ligament and/or tendon include racehorses and athletes. Subjects in need of treatment with a NELL1 peptide or nucleic acid molecular encoding the same include those that have or are prone to impaired wound healing, impaired neovascularization, or impaired angiogenesis, including but not limited to those subjects with diabetes (type 1 or type 2), vascular diseases, hypercholesterolemia, and aging.

An injury or wound refers to damage or harm to a structure or function of the body caused by intrinsic and/or extrinsic factors. Non-limiting intrinsic or extrinsic factors that can cause an injury or wound include those of chemical, mechanical, thermal, bacterial, or physical means and encompass those that occur as the result of surgical procedures, overuse, or environmental conditions. The wound can be an open wound in which the skin is broken (e.g., lacerations, abrasions, puncture wound) or a closed wound. Particular wounds that can be healed with NELL1 include, but are not limited to, bone injuries (e.g., complete or partial fractures), skin wounds, and skeletal muscle injuries.

Intrinsic factors that can contribute to the development of injuries to tendons and/or ligaments include genetic susceptibility, overuse, poor biomechanics, poor nutrition, and obesity. The extrinsic factors are often related to sports and include excessive forces or loading, poor training techniques, environmental conditions, and surgical procedures. The injury to the tendon and/or ligament can be a closed wound or an open wound, where the skin is lacerated, cut or punctured. The injury can include inflammation, a sprain, strain, tearing, stretching, or laceration of the tendon or ligament.

A tendon is a band of connective tissue that connects muscles to bones or cartilage. A ligament is a band of connective tissue that connects bones to other bones to form joints.

Injuries to tendons include tendinitis (acute tendon injury accompanied by inflammation), tendinosis (chronic tendon injury with degeneration at the cellular level and no inflammation), and other tendinopathies exhibiting chronic tendon injury with no etiological implications. With tendinosis, damage to collagen, cells, and the vascular components of the tendon can occur, such as irregularities of collagen fibrils (e.g., disorientation, degeneration, thinning, non-uniformity in length or diameter, increase in the amount of glycosaminoglycans between the fibrils), rounded tenocytes or other cell abnormalities, and the ingrowth of blood vessels.

The healing of an injury to any type of tendon can be promoted with NELL1, including a hand flexor tendon, a tendon within the rotator cuff, and an Achilles tendon, and within horses, a superficial digital flexor tendon (SDFT) and a deep digital flexor tendon (DDFT) of either the hindlimb(s) or forelimb(s).

Likewise, the healing of an injury to any type of ligament can be promoted with NELL1, including an anterior cruciate ligament (ACL), posterior cruciate ligament (PCL), lateral collateral ligament (LCL), medial collateral ligament (MCL), and in horses, a suspensory ligament of either the hindlimb(s) or forelimb(s). A common ligament injury in horses that can be healed according to the presently disclosed methods is proximal suspensory desmitis, an inflammation of the suspensory ligament just below the hock.

The NELL1 peptide or nucleic acid encoding the same can be administered to subjects in need thereof in the form of a composition further comprising a carrier. The term "carrier" as used herein describes a material that does not cause significant irritation to an organism and does not abrogate the biological activity and properties of the composition of the described invention. Carriers must be of sufficiently high purity and of sufficiently low toxicity to render them suitable for administration to a subject being treated. The carrier can be inert, or it can possess pharmaceutical benefits.

A pharmaceutical composition is a composition that is employed to prevent, reduce in intensity, cure or otherwise treat a target condition or disease.

A pharmaceutically acceptable carrier refers to one or more compatible solid or liquid filler, diluents or encapsulating substances which are suitable for administration to a human or other vertebrate animal.

The formulations may be presented conveniently in unit dosage form and may be prepared by any of the methods well known in the art of pharmacy. All methods include the step of bringing into association the NELL1 peptide or nucleic acid encoding the same ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The NELL1 peptide or nucleic acid encoding the same may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly(orthoesters) and poly(anhydrides). Depot injectable formulations also are prepared by entrapping the drug in liposomes or microemulsions which are compatible with body tissues.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions, may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono-or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring the addition of the sterile liquid carrier, for example, saline, water-for-injection, a semi-liquid foam, or gel, immediately prior to use. Extemporaneous injection solutions and suspensions may be prepared from sterile powders, granules and tablets of the kind previously described. Alternatively, a NELL1 peptide or nucleic acid encoding the same is dissolved in a buffered liquid solution that is frozen in a unit-dose or multi-dose container and later thawed for injection or kept/stabilized under refrigeration until use. Any label on, or associated with, the container(s) indicates that the enclosed composition is used for promoting the healing of injuries to tendons and/or ligaments.

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. In some embodiments, the use of a long-term sustained release implant may be particularly suitable for treatment of chronic conditions. Long-term sustained release implants are well-known to those of ordinary skill in the art and include some of the release systems described above.

In some embodiments wherein the pharmaceutical composition is in the form of an implant, the NELL1 peptide or a nucleic acid encoding the same is impregnated into drug eluting devices, scaffolds or matrices that are implanted into an injured area to deliver NELL1 in a controlled release fashion. The protein can also be linked to sutures that are used for tendon and/or ligament surgeries. In those instances wherein the NELL1 peptide is delivered by genetically modified donor cells, the cells can be incorporated into a matrix containing an appropriate microenvironment to maintain, for a given time, the viability and growth of the genetically modified donor cells.

Non-limiting examples of suitable matrices include, but are not limited to, wound dressings, collagen matrix, patches, and hydrogels. The matrix can be applied to the injured tendon and/or ligament that has been exposed post-surgically, for example. After the injured tendon and/or ligament is healed, the matrix can be removed or the matrix incorporating the NELL1 peptide or nucleic acid encoding the same can be replaced intermittently throughout the healing process. In some embodiments, a rapidly degradable (e.g., 3-5 days in horses and 1-2 weeks in rats) scaffold or dressing is used to deliver NELL1 (e.g., calcium alginate). Rapidly degradable scaffolds or dressings allow for the release of a burst of NELL1 in the first phase of healing and activates tissue regeneration instead of scarring pathways. In certain embodiments, the scaffold or dressing is simpler (e.g., consisting essentially of collagen type A), rather than a complex biological carrier, such as those made from urinary bladder or intestinal linings that may comprise various growth factors and collagens. In some embodiments, the wound dressing or matrix used to deliver NELL1 comprises or consists essentially of calcium alginate.

The NELL1 peptide or nucleic acid encoding the same can be administered to a subject by dispensing, supplying, applying, or giving the NELL1 peptide or nucleic acid encoding the same to the subject. Administration may be in vivo or administration directly to tissue ex vivo. Generally, NELL1 peptides, nucleic acid molecules encoding the same, or compositions comprising the NELL1 peptide or nucleic acid may be administered systemically either orally, buccally, parenterally, topically, by inhalation or insufflation (i.e., through the mouth or through the nose), or rectally in dosage unit formulations, optionally containing the conventional nontoxic pharmaceutically acceptable carriers, adjuvants, and vehicles as desired, or may be locally administered by means such as, but not limited to, injection, implantation, grafting, or topical application. Additional administration may be performed, for example, intravenously, transmucosally, transdermally, intramuscularly, subcutaneously, intraperitoneally, intrathecally, intralymphatically, intralesionally, or epidurally.

Any suitable route of administration may be used to deliver the NELL1 peptide or nucleic acid molecule encoding the same for the purposes of tissue regeneration, such as promoting the healing of an injury to a tendon and/or ligament. In certain embodiments, the NELL1 peptide or nucleic acid encoding the same is administered locally to the site of injury or of desired tissue regeneration or fibroblast migration and/or proliferation. In some of these embodiments, the NELL1 peptide, NELL1 nucleic acid molecule, or a composition comprising the NELL1 peptide or NELL1 nucleic acid molecule are administered parenterally. The term "parenteral" as used herein refers to introduction into the body by way of an injection (i.e., administration by injection), including, for example, subcutaneously (i.e., an injection beneath the skin beneath the dermis into the subcutaneous tissue or "superficial fascia"), intramuscularly (i.e., an injection into a muscle), intravenously (i.e., an injection into a vein), intrathecally (i.e., an injection into the space around the spinal cord or under the arachnoid membrane of the brain), intrasternal injection or infusion techniques. A parenterally administered composition is delivered using a needle, e.g., a surgical needle. Injectable preparations, such as sterile injectable aqueous or oleaginous suspensions, may be formulated according to the known art using suitable dispersing or wetting agents and suspending agents. According to some such embodiments, the NELL1 peptide or nucleic acid molecule encoding the same is administered by injection.

In certain embodiments, the NELL1 peptide or nucleic acid molecule is administered as a spray onto a tissue, such as a tendon or ligament that has been exposed surgically (e.g., tendon splitting procedures to case strain). The NELL1 peptide or nucleic acid molecule can also be administered via adhesion to novel materials such as nanoparticles. Lyophilized NELL protein, which may or not be reconstituted as a liquid or a gel, can be placed directly onto an injured tendon or ligament.

Administering can be performed, for example, once, a plurality of times, and/or over one or more extended periods. Generally, an effective dose of the NELL1 peptide or nucleic acid encoding the same is administered to a subject one or more times. In certain preferred embodiments, the course of treatment will comprise multiple doses of the NELL1 peptide or nucleic acid encoding the same over a period of weeks or months. More specifically, the NELL1 peptide or nucleic acid encoding the same may be administered once every day, every two days, every three days, every four days, every five days, every six days, every week, every ten days, every two weeks, every three weeks, every month, every six weeks, every two months, every ten weeks or every three months. In this regard, it will be appreciated that the dosages may be altered or the interval may be adjusted based on patient response and clinical practices.

An effective amount of a pharmaceutical composition of the invention is any amount that is effective to achieve its purpose. The effective amount, usually expressed in mg/kg can be determined by routine methods during pre-clinical and clinical trials by those of skill in the art.

The NELL1 peptide or nucleic acid encoding the same can be administered immediately after the injury to a tissue (e.g., the tendon and/or ligament) occurred or the administration can be delayed post-injury for about three hours, 12 hours, one day, two days, three days, four days, five days, six days, seven days, eight days, nine days, ten days, two weeks, three weeks, or longer.

The NELL1 peptide or nucleic acid encoding the same can be administered prior to, along with, or subsequent to another treatment for healing the injury (e.g., tendon and/or ligament injury). Non-limiting examples of other treatments include surgery, rehabilitation, cryotherapy, administration of precursor cells, extracellular matrix materials (synthetic or purified), anti-inflammatory agents, and analgesics.

NELL1 can be combined with cells that are important in the formation of new tissues. For example, for tendons and ligaments tenocytes, tendon-derived fibroblasts, tendon stem/progenitor cells (TSPCs) and perivascular stem cells, as well as adult stem cells, such as mesenchymal stem cells, adipose derived stem cells, and bone marrow aspirate, can be used. The combination of NELL1 with cells can be delivered as an injectable mixture or in a complex scaffold (synthetic or natural scaffold) that degrades in the injured site and acts both as a starting architectural guide for new tissue to form and also for releasing correct signals that draw into the injured site growth factors and cells needed for healing. This can be either novel scaffolds or existing commercial products (e.g. mesenchymal stem cells) that have already demonstrated activity in healing injuries, such as those to tendons and/or ligaments but whose activity can be boosted by the addition of NELL1 for more severe or challenging traumatic tissue damage. (Yanming et al. 2007; Tempfer et al. 2009; Nemoto et al. 2013)

NELL1 can be added to formulations or products that are acellular extracellular matrix materials either extracted from natural sources (e.g. linings of urinary bladder, small intestinal submucosa etc.) or manufactured as a synthetic. Acellular products for regenerative medicine that contain extracellular matrix material may not have all the needed signals for tissue regeneration and the addition of NELL1 can enhance the ability of some of these materials to effect cell differentiation and tissue maturation.

In practicing combination therapy, the NELL1 peptide or nucleic acid encoding the same and the additional treatment or therapeutic agent may be administered to the subject simultaneously, either in a single composition, or as two or more distinct compositions using the same or different administration routes. Alternatively, the NELL1 peptide or nucleic acid encoding the same may precede, or follow, the additional treatment or therapeutic agent by, e.g., intervals ranging from minutes to weeks. In at least one embodiment, the NELL1 peptide or nucleic acid encoding the same and the additional treatment or therapeutic agent are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the NELL1 peptide or nucleic acid encoding the same and the additional treatment or therapeutic agent. In some of these embodiments, the NELL1 peptide or nucleic acid is administered along with platelet derived plasma (PRP).

IV. Articles of Manufacture

The invention includes kits comprising a NELL1 peptide or nucleic acid encoding the same comprising one or more containers. The kit can contain a unit dosage of a NELL1 peptide or nucleic acid encoding the same, and may also contain one or more additional agents, such as those agents that promote wound healing, stimulate the regeneration of a tissue, or promote the migration or proliferation of fibroblast cells.

The components of the kit may be provided in one or more liquid solutions, such as a sterile aqueous solution. Alternatively, the components of the kit may be provided in a lyophilized form that is suitable for reconstitution with an aqueous or non-aqueous liquid. Such a liquid may be provided in a separate container.

The kit can further comprise a label or package insert associated with the container(s) providing information regarding the use of the kit, such as for regenerating tissues, promoting the healing of wounds, or promoting the migration or proliferation of fibroblast cells.

IV. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In addition, ranges provided in the specification and appended claims include both end points and all points between the end points. Therefore, a range of 2.0 to 3.0 includes 2.0, 3.0, and all points between 2.0 and 3.0.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

General methods in molecular genetics and genetic engineering useful in the present invention are described in the current editions of Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, CA), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, CA), Culture of Animal Cells: A Manual of Basic Technique, 2nd Ed. (R. I. Freshney. 1987. Liss, Inc. New York, NY), and Gene Transfer and Expression Protocols, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference, regardless of whether the phrase "incorporated by reference" is or is not used in relation to the particular reference. The foregoing detailed description and the examples that follow have been given for clarity of understanding. No unnecessary limitations are to be understood therefrom. The invention is not limited to the exact details shown and described. Variations obvious to one skilled in the art are included in the invention defined by the claims. Any section headings used herein are for organizational purposes and are not to be construed as limiting the subject matter described.

V. Sequence Summary and Sequences

The following Table 1 provides a summary of the included sequences.

TABLE 1

Nucleotide and amino acid sequences disclosed herein.

| SEQ ID NO. | Description |
|---|---|
| 1 | *Homo sapiens* NELL1 isoform 1 transcript variant (nucleotide) |
| 2 | *Homo sapiens* NELL1 isoform 1 (amino acid) |
| 3 | *Homo sapiens* NELL1 isoform 2 transcript variant (nucleotide) |
| 4 | *Homo sapiens* NELL1 isoform 2 (amino acid) |
| 5 | *Equus caballus* NELL1 isoform 1 (nucleotide) |
| 6 | *Equus caballus* NELL1 isoform 1 (amino acid) |
| 7 | *Equus caballus* NELL1 isoform 2 (nucleotide) |
| 8 | *Equus caballus* NELL1 isoform 2 (amino acid) |
| 9 | *Mus musculus* NELL1 (nucleotide) |
| 10 | *Mus musculus* NELL1 (amino acid) |
| 11 | *Rattus norvegicus* NELL1 (nucleotide) |
| 12 | *Rattus norvegicus* NELL1 (amino acid) |
| 13 | *Felis catus* NELL1 isoform 1 (amino acid) |
| 14 | *Felis catus* NELL1 isoform 2 (amino acid) |
| 15 | *Canis lupis familiaris* NELL1 (amino acid) |
| 16 | *Ovis aries* NELL1 (amino acid) |
| 17 | *Homo sapiens* NELL1 fragment (amino acid) |
| 18 | *Equus caballus* NELL1 fragment (amino acid) |
| 19 | *Bos taurus* NELL1 (amino acid) |

```
Homo sapiens NELL1 isoform 1 nucleotide sequence (SEQ ID NO: 1) and
translated amino acid sequence (SEQ ID NO: 2)
atatgcgagc gcagcacccg gcgctgccga gccacctccc ccgccgcccg ctagcaagtt      60
tggcggctcc aagccaggcg cgcctcagga tccaggctca tttgcttcca cctagcttcg    120
gtgccccctg ctaggcgggg accctcgaga gcg atg ccg atg gat ttg att tta    174
                                     Met Pro Met Asp Leu Ile Leu
gtt gtg tgg ttc tgt gtg tgc act gcc agg aca gtg gtg ggc ttt ggg    222
Val Val Trp Phe Cys Val Cys Thr Ala Arg Thr Val Val Gly Phe Gly
atg gac cct gac ctt cag atg gat atc gtc acc gag ctt gac ctt gtg    270
Met Asp Pro Asp Leu Gln Met Asp Ile Val Thr Glu Leu Asp Leu Val
aac acc acc ctt gga gtt gct cag gtg tct gga atg cac aat gcc agc    318
Asn Thr Thr Leu Gly Val Ala Gln Val Ser Gly Met His Asn Ala Ser
aaa gca ttt tta ttt caa gac ata gaa aga gag atc cat gca gct cct    366
Lys Ala Phe Leu Phe Gln Asp Arg Glu Ile His Ala Ala Pro
cat gtg agt gag aaa tta att cag ctg ttc cgg aac aag agt gaa ttc    414
His Val Ser Glu Lys Leu Ile Gln Leu Phe Arg Asn Lys Ser Glu Phe
acc att ttg gcc act gta cag cag aag cca tcc act tca gga gtg ata    462
Thr Ile Leu Ala Thr Val Gln Gln Lys Pro Ser Thr Ser Gly Val Ile
ctg tcc att cga gaa ctg gag cac agc tat ttt gaa ctg gag agc agt    510
```

-continued

```
Leu Ser Ile Arg Glu Leu Glu His Ser Tyr Phe Glu Leu Glu Ser Ser
ggc ctg agg gat gag att cgg tat cac tac ata cac aat ggg aag cca    558
Gly Leu Arg Asp Glu Ile Arg Tyr His Tyr Ile His Asn Gly Lys Pro
agg aca gag gca ctt cct tac cgc atg gca gat gga caa tgg cac aag    606
Arg Thr Glu Ala Leu Pro Tyr Arg Met Ala Asp Gly Gln Trp His Lys
gtt gca ctg tca gtt agc gcc tct cat ctc ctg ctc cat gtc gac tgt    654
Val Ala Leu Ser Val Ser Ala Ser His Leu Leu Leu His Val Asp Cys
aac agg att tat gag cgt gtg ata gac cct cca gat acc aac ctt ccc    702
Asn Arg Ile Tyr Glu Arg Val Ile Asp Pro Pro Asp Thr Asn Leu Pro
cca gga atc aat tta tgg ctt ggc cag cgc aac caa aag cat gga tta    750
Pro Gly Ile Asn Leu Trp Leu Gly Gln Arg Asn Gln Lys His Gly Leu
ttc aaa ggg atc atc caa gat ggg aag atc atc ttt atg ccg aat gga    798
Phe Lys Gly Ile Ile Gln Asp Gly Lys Ile Ile Phe Met Pro Asn Gly
tat ata aca cag tgt cca aat cta aat cac act tgc cca acc agt        846
Tyr Ile Thr Gln Cys Pro Asn Leu Asn His Thr Cys Pro Thr Cys Ser
gat ttc tta agc ctg gtg caa gga ata atg gat tta caa gag ctt ttg    894
Asp Phe Leu Ser Leu Val Gln Gly Ile Met Asp Leu Gln Glu Leu Leu
gcc aag atg act gca aaa cta aat tat gca gaa aga ctt agt caa        942
Ala Lys Met Thr Ala Lys Leu Asn Tyr Ala Glu Thr Arg Leu Ser Gln
ttg gaa aac tgt cat tgt gag aag act tgt caa gtg agt gga ctg ctc    990
Leu Glu Asn Cys His Cys Glu Lys Thr Cys Gln Val Ser Gly Leu Leu
tat cga gat caa gac tct tgg gta gat ggt gac tgc agg aac tgc       1038
Tyr Arg Asp Gln Asp Ser Trp Val Asp Gly Asp His Cys Arg Asn Cys
act tgc aaa agt ggt gcc gtg gaa tgc cga agg atg tcc tgt ccc cct   1086
Thr Cys Lys Ser Gly Ala Val Glu Cys Arg Arg Met Ser Cys Pro Pro
ctc aat tgc tcc cca gac tcc ctc cca gtg cac atc gct ggc cag tgc   1134
Leu Asn Cys Ser Pro Asp Ser Leu Pro Val His Ile Ala Gly Gln Cys
tgt aag gtc tgc cga cca aaa tgt atc tat gga gga aaa gtt ctt gca   1182
Cys Lys Val Cys Arg Pro Lys Cys Ile Tyr Gly Gly Lys Val Leu Ala
gaa ggc cag cgg att tta acc aag agc tgt cgg gaa tgc cga ggt ctg   1230
Glu Gly Gln Arg Ile Leu Thr Lys Ser Cys Arg Glu Cys Arg Gly Leu
gtt tta gta aaa att aca gaa atg tgt cct cct ttg aac tgc tca gaa   1278
Val Leu Val Lys Ile Thr Glu Met Cys Pro Pro Leu Asn Cys Ser Glu
aag gat cac att ctt cct gag aat cag tgc tgc cgt gtc tgt aga ggt   1326
Lys Asp His Ile Leu Pro Glu Asn Gln Cys Cys Arg Val Cys Arg Gly
cat aac ttt tgt gca gaa gga cct aaa tgt ggt gaa aac tca gag tgc   1374
His Asn Phe Cys Ala Glu Gly Pro Lys Cys Gly Glu Asn Ser Glu Cys
aaa aac tgg aat aca aaa gct act tgc gag tgc aag agt ggt tac atc   1422
Lys Asn Trp Asn Thr Lys Ala Thr Cys Glu Cys Lys Ser Gly Tyr Ile
tct gtc cag gga gac tct gcc tac tgt gaa gat att gat gag tgt gca   1470
Ser Val Gln Gly Asp Ser Ala Tyr Cys Glu Asp Ile Asp Glu Cys Ala
gct aag atg cat tac tgt cat gcc aat act gtg tgt gtc aac ctt cct   1518
Ala Lys Met His Tyr Cys His Ala Asn Thr Val Cys Val Asn Leu Pro
ggg tta tat cgc tgt gac tgt gtc cca gga tac att cgt gtg gat gac   1566
Gly Leu Tyr Arg Cys Asp Cys Val Pro Gly Tyr Ile Arg Val Asp Asp
ttc tct tgt aca gaa cac gat gaa tgt ggc agc ggc cag cac aac tgt   1614
Phe Ser Cys Thr Glu His Asp Glu Cys Gly Ser Gly Gln His Asn Cys
gat gag aat gcc atc tgc acc aac act gtc cag gga cac agc tgc acc   1662
Asp Glu Asn Ala Ile Cys Thr Asn Thr Val Gln Gly His Ser Cys Thr
tgc aaa ccg ggc tac gtg ggg aac ggg acc atc tgc aga gct ttc tgt   1710
Cys Lys Pro Gly Tyr Val Gly Asn Gly Thr Ile Cys Arg Ala Phe Cys
gaa gag ggc tgc aga tac ggt gga acg tgt gtg gct ccc aac aaa tgt   1758
Glu Glu Gly Cys Arg Tyr Gly Gly Thr Cys Val Ala Pro Asn Lys Cys
gtc tgt cca tct gga ttc aca gga agc cac tgc gag aaa gat att gat   1806
Val Cys Pro Ser Gly Phe Thr Gly Ser His Cys Glu Lys Asp Ile Asp
gaa tgt tca gag gga atc att gag tgc cac aac cat tcc cgc tgc gtt   1854
Glu Cys Ser Glu Gly Ile Ile Glu Cys His Asn His Ser Arg Cys Val
aac ctg cca ggg tgg tac cac tgt gag tgc aga agc ggt ttc cat gac   1902
Asn Leu Pro Gly Trp Tyr His Cys Glu Cys Arg Ser Gly Phe His Asp
gat ggg acc tat tca ctg tcc ggg gag tcc tgt att gac att gat gaa   1950
Asp Gly Thr Tyr Ser Leu Ser Gly Glu Ser Cys Ile Asp Ile Asp Glu
tgt gcc tta aga act cac acc tgt tgg aac gat tct gcc tgc atc aac   1998
Cys Ala Leu Arg Thr His Thr Cys Trp Asn Asp Ser Ala Cys Ile Asn
ctg gca ggg ttt gac tgt ctc tgc ccc tcc ggg cca tcc tgt tct       2046
Leu Ala Gly Gly Phe Asp Cys Leu Cys Pro Ser Gly Pro Ser Cys Ser
ggt gac tgt cct cat gaa ggg ggg ctg aag cac aat ggc cag gtg tgg   2094
Gly Asp Cys Pro His Glu Gly Gly Leu Lys His Asn Gly Gln Val Trp
acc ttg aaa gaa gac agg tgt tct gtc tgc tcc tgc aag gat ggc aag   2142
Thr Leu Lys Glu Asp Arg Cys Ser Val Cys Ser Cys Lys Asp Gly Lys
ata ttc tgc cga cgg aca gct tgt gat tgc cag aat cca agt gct gac   2190
Ile Phe Cys Arg Arg Thr Ala Cys Asp Cys Gln Asn Pro Ser Ala Asp
cta ttc tgt tgc cca gaa tgt gac acc aga gtc aca agt caa tgt tta   2238
Leu Phe Cys Cys Pro Glu Cys Asp Thr Arg Val Thr Ser Gln Cys Leu
gac caa aat ggt cac aaa ctg tat cga agt gga gac aat tgg acc cat   2286
Asp Gln Asn Gly His Lys Leu Tyr Arg Ser Gly Asp Asn Trp Thr His
agc tgt cag cag tgt cgg tgt ctg gaa gga gta gat tgc tgg cca       2334
Ser Cys Gln Gln Cys Arg Cys Leu Glu Gly Glu Val Asp Cys Trp Pro
ctc act tgc ccc aac ttg agc tgt gag tat aca gct atc tta gaa ggg   2382
Leu Thr Cys Pro Asn Leu Ser Cys Glu Tyr Thr Ala Ile Leu Glu Gly
```

```
gaa tgt tgt ccc cgc tgt gtc agt gac ccc tgc cta gct gat aac atc   2430
Glu Cys Cys Pro Arg Cys Val Ser Asp Pro Cys Leu Ala Asp Asn Ile
acc tat gac atc aga aaa act tgc ctg gac agt tat ggt gtt tca cgg   2478
Thr Tyr Asp Ile Arg Lys Thr Cys Leu Asp Ser Tyr Gly Val Ser Arg
ctt agt ggc tca gtg tgg acg atg gct gga tct ccc tgc aca acc tgt   2526
Leu Ser Gly Ser Val Trp Thr Met Ala Gly Ser Pro Cys Thr Thr Cys
aaa tgc aag aat gga aga gtc tgt tgt tct gtg gat ttt gag tgt ctt   2574
Lys Cys Lys Asn Gly Arg Val Cys Cys Ser Val Asp Phe Glu Cys Leu
caa aat aat tga agtatttaca gtggactcaa cgcagaagaa tggacgaaat       2626
Gln Asn Asn  *
gaccatccaa cgtgattaag gataggaatc ggtagtttgg ttttttgtt tgttttgttt  2686
ttttaaccac agataattgc caaagtttcc acctgaggac ggtgtttgga ggttgccttt  2746
tggacctacc actttgctca ttcttgctaa cctagtctag gtgacctaca gtgccgtgca  2806
tttaagtcaa tggttgttaa aagaagtttc ccgtgttgta aatcatgttt cccttatcag  2866
atcatttgca aatacattta aatgatctca tggtaaatgt tgatgtattt tttggtttat  2926
tttgtgtact aacataatag agagagactc agctccttt attttatttg ttgatttatg   2986
gatcaaattc taaaataaag ttgcctgttg tgacttttgt cccatctact gcatacttag  3046
tgctgagatc cctgtaaaat gttttgatga aaatatgtat gtagagtcca gtcgcattat  3106
acatacattt catagtgctg aaccttctta aatgcctact cattcagctt aaacaggctg  3166
aagccaagta tgacaagag gggaagggcc aaaaacataa tcaagaata attttaaaga    3226
gaattcttgt ctctcttgca aaaaaaaaa                                    3255
```

*Homo sapiens* NELL1 isoform 1 amino acid sequence (SEQ ID NO: 2)

```
Met Pro Met Asp Leu Ile Leu Val Val Trp Phe Cys Val Cys Thr Ala Arg
Thr Val Val Gly Phe Gly Met Asp Pro Asp Leu Gln Met Asp Ile Val Thr
Glu Leu Asp Leu Val Asn Thr Thr Leu Gly Val Ala Gln Val Ser Gly Met
His Asn Ala Ser Lys Ala Phe Leu Phe Gln Asp Ile Glu Arg Glu Ile His
Ala Ala Pro His Val Ser Glu Lys Leu Ile Gln Leu Phe Arg Asn Lys Ser
Glu Phe Thr Ile Leu Ala Thr Val Gln Gln Lys Pro Ser Thr Ser Gly Val
Ile Leu Ser Ile Arg Glu Leu Glu His Ser Tyr Phe Glu Leu Glu Ser Ser
Gly Leu Arg Asp Glu Ile Arg Tyr His Tyr Ile His Asn Gly Lys Pro Arg
Thr Glu Ala Leu Pro Tyr Arg Met Ala Asp Gly Gln Trp His Lys Val Ala
Leu Ser Val Ser Ala Ser His Leu Leu Leu His Val Asp Cys Asn Arg Ile
Tyr Glu Arg Val Ile Asp Pro Pro Asp Thr Asn Leu Pro Pro Gly Ile Asn
Leu Trp Leu Gly Gln Arg Asn Gln Lys His Gly Leu Phe Lys Gly Ile Ile
Gln Asp Gly Lys Ile Ile Phe Met Pro Asn Gly Tyr Ile Thr Gln Cys Pro
Asn Leu Asn His Thr Cys Pro Thr Cys Ser Asp Phe Leu Ser Leu Val Gln
Gly Ile Met Asp Leu Gln Glu Leu Leu Ala Lys Met Thr Ala Lys Leu Asn
Tyr Ala Glu Thr Arg Leu Ser Gln Leu Glu Asn Cys His Cys Glu Lys Thr
Cys Gln Val Ser Gly Leu Leu Tyr Arg Asp Gln Asp Ser Trp Val Asp Gly
Asp His Cys Arg Asn Cys Thr Cys Lys Ser Gly Ala Val Glu Cys Arg Arg
Met Ser Cys Pro Pro Leu Asn Cys Ser Pro Asp Ser Leu Pro Val His Ile
Ala Gly Gln Cys Cys Lys Val Cys Arg Pro Lys Cys Ile Tyr Gly Gly Lys
Val Leu Ala Glu Gly Gln Arg Ile Leu Thr Lys Ser Cys Arg Glu Cys Arg
Gly Gly Val Leu Val Lys Ile Thr Glu Met Cys Pro Pro Leu Asn Cys Ser
Glu Lys Asp His Ile Leu Pro Glu Asn Gln Cys Cys Arg Val Cys Arg Gly
His Asn Phe Cys Ala Glu Gly Pro Lys Cys Gly Glu Asn Ser Glu Cys Lys
Asn Trp Asn Thr Lys Ala Thr Cys Glu Cys Lys Ser Gly Tyr Ile Ser Val
Gln Gly Asp Ser Ala Tyr Cys Glu Asp Ile Asp Glu Cys Ala Ala Lys Met
His Tyr Cys His Ala Asn Thr Val Cys Val Asn Leu Pro Gly Leu Tyr Arg
Cys Asp Cys Val Pro Gly Tyr Ile Arg Val Asp Asp Phe Ser Cys Thr Glu
His Asp Glu Cys Gly Ser Gly Gln His Asn Cys Asp Glu Asn Ala Ile Cys
Thr Asn Thr Val Gln Gly His Ser Cys Thr Cys Lys Pro Gly Tyr Val Gly
Asn Gly Thr Ile Cys Arg Ala Phe Cys Glu Glu Gly Cys Arg Tyr Gly Gly
Thr Cys Val Ala Pro Asn Lys Cys Val Cys Pro Ser Gly Phe Thr Gly Ser
His Cys Glu Lys Asp Ile Asp Glu Cys Ser Glu Gly Ile Ile Glu Cys His
Asn His Ser Arg Cys Val Asn Leu Pro Gly Trp Tyr His Cys Glu Cys Arg
Ser Gly Phe His Asp Asp Gly Thr Tyr Ser Leu Ser Gly Glu Ser Cys Ile
Asp Ile Asp Glu Cys Ala Leu Arg Thr His Thr Cys Trp Asn Asp Ser Ala
Cys Ile Asn Leu Ala Gly Gly Phe Asp Cys Leu Cys Pro Ser Gly Pro Ser
Cys Ser Gly Asp Cys Pro His Glu Gly Gly Leu Lys His Asn Gly Gln Val
Trp Thr Leu Lys Glu Asp Arg Cys Ser Val Cys Ser Cys Lys Asp Gly Lys
Ile Phe Cys Arg Arg Thr Ala Cys Asp Cys Gln Asn Pro Ser Ala Asp Leu
Phe Cys Cys Pro Glu Cys Asp Thr Arg Val Thr Ser Gln Cys Leu Asp Gln
Asn Gly His Lys Leu Tyr Arg Ser Gly Asp Asn Trp Thr His Ser Cys Gln
```

```
Gln Cys Arg Cys Leu Glu Gly Glu Val Asp Cys Trp Pro Leu Thr Cys Pro
Asn Leu Ser Cys Glu Tyr Thr Ala Ile Leu Glu Gly Glu Cys Cys Pro Arg
Cys Val Ser Asp Pro Cys Leu Ala Asp Asn Ile Thr Tyr Asp Ile Arg Lys
Thr Cys Leu Asp Ser Tyr Gly Val Ser Arg Leu Ser Gly Ser Val Trp Thr
Met Ala Gly Ser Pro Cys Thr Thr Cys Lys Cys Lys Asn Gly Arg Val Cys
Cys Ser Val Asp Phe Glu Cys Leu Gln Asn Asn
```

*Homo sapiens* NELL1 isoform 2 nucleotide sequence (SEQ ID NO: 3) and translated amino acid sequence (SEQ ID NO: 4)

```
atatgcgagc gcagcacccg gcgctgccga gccacctccc ccgccgcccg ctagcaagtt    60
tggcggctcc aagccaggcg cgcctcagga tccaggctca tttgcttcca cctagcttcg   120
gtgcccctg ctaggcgggg accctcgaga gcg atg ccg atg gat ttg att tta    174
                                   Met Pro Met Asp Leu Ile Leu
gtt gtg tgg ttc tgt gtg tgc act gcc agg aca gtg gtg ggc ttt ggg    222
Val Val Trp Phe Cys Val Cys Thr Ala Arg Thr Val Val Gly Phe Gly
atg gac cct gac ctt cag atg gat atc gtc acc gag ctt gac ctt gtg    270
Met Asp Pro Asp Leu Gln Met Asp Ile Val Thr Glu Leu Asp Leu Val
aac acc acc ctt gga gtt gct cag gtg tct gga atg cac aat gcc agc    318
Asn Thr Thr Leu Gly Val Ala Gln Val Ser Gly Met His Asn Ala Ser
aaa gca ttt tta ttt caa gac ata gaa aga gag atc cat gca gct cct    366
Lys Ala Phe Leu Phe Gln Asp Ile Glu Arg Glu Ile His Ala Ala Pro
cat gtg agt gag aaa tta att cag ctg ttc cgg aac aag agt gaa ttc    414
His Val Ser Glu Lys Leu Ile Gln Leu Phe Arg Asn Lys Ser Glu Phe
acc att ttg gcc act gta cag cag aag cca tcc act tca gga gtg ata    462
Thr Ile Leu Ala Thr Val Gln Gln Lys Pro Ser Thr Ser Gly Val Ile
ctg tcc att cga gaa ctg gag cac agc tat ttt gaa ctg gag agt agt    510
Leu Ser Ile Arg Glu Leu Glu His Ser Tyr Phe Glu Leu Glu Ser Ser
ggc ctg agg gat gag att cgg tat cac tac ata cac aat ggg aag cca    558
Gly Leu Arg Asp Glu Ile Arg Tyr His Tyr Ile His Asn Gly Lys Pro
agg aca gag gca ctt cct tac cgc atg gca gat gga caa tgg cac aag    606
Arg Thr Glu Ala Leu Pro Tyr Arg Met Ala Asp Gly Gln Trp His Lys
gtt gca ctg tca gtt agc gcc tct cat ctc ctg ctc cat gtc gac tgt    654
Val Ala Leu Ser Val Ser Ala Ser His Leu Leu Leu His Val Asp Cys
aac agg att tat gag cgt gtg ata gac cct cca gat acc aac ctt ccc    702
Asn Arg Ile Tyr Glu Arg Val Ile Asp Pro Pro Asp Thr Asn Leu Pro
cca gga atc aat tta tgg ctt ggc cag cgc aac caa aag cat ggc tta    750
Pro Gly Ile Asn Leu Trp Leu Gly Gln Arg Asn Gln Lys His Gly Leu
ttc aaa ggg atc atc caa gat ggg aag atc atc ttt atg ccg aat gga    798
Phe Lys Gly Ile Ile Gln Asp Gly Lys Ile Ile Phe Met Pro Asn Gly
tat ata aca cag tgt cca aat cta aat cac act tgc cca acc tgc agt    846
Tyr Ile Thr Gln Cys Pro Asn Leu Asn His Thr Cys Pro Thr Cys Ser
gat ttc tta agc ctg gtg caa gga ata atg gat tta caa gag ctt ttg    894
Asp Phe Leu Ser Leu Val Gln Gly Ile Met Asp Leu Gln Glu Leu Leu
gcc aag atg act gca aaa cta aat tat gca gag aca aga ctt agt caa    942
Ala Lys Met Thr Ala Lys Leu Asn Tyr Ala Glu Thr Arg Leu Ser Gln
ttg gaa aac tgt cat tgt gag aag act tgt caa gtg agt gga ctg ctc    990
Leu Glu Asn Cys His Cys Glu Lys Thr Cys Gln Val Ser Gly Leu Leu
tat cga gat caa gac tct tgg gta gat ggt gac cat tgc agg aac tgc   1038
Tyr Arg Asp Gln Asp Ser Trp Val Asp Gly Asp His Cys Arg Asn Cys
act tgc aaa agt ggt gcc gtg gaa tgc cga agg atg tcc tgt ccc cct   1086
Thr Cys Lys Ser Gly Ala Val Glu Cys Arg Arg Met Ser Cys Pro Pro
ctc aat tgc tcc cca gac tcc ctc cca gtg cac att gct ggc cag tgc   1134
Leu Asn Cys Ser Pro Asp Ser Leu Pro Val His Ile Ala Gly Gln Cys
tgt aag gtc tgc cga cca aaa tgt atc tat gga gga aaa gtt ctt gca   1182
Cys Lys Val Cys Arg Pro Lys Cys Ile Tyr Gly Gly Lys Val Leu Ala
gaa ggc cag cgg att tta acc aag agc tgt cga gaa tgc cga ggt gga   1230
Glu Gly Gln Arg Ile Leu Thr Lys Ser Cys Arg Glu Cys Arg Gly Gly
gtt tta gta aaa att aca gaa atg tgt cct cct ttg aac tgc tca gaa   1278
Val Leu Val Lys Ile Thr Glu Met Cys Pro Pro Leu Asn Cys Ser Glu
aag gat cac att ctt cct gag aat cag tgc tgc cgt gtc tgt aga ggt   1326
Lys Asp His Ile Leu Pro Glu Asn Gln Cys Cys Arg Val Cys Arg Gly
cat aac ttt tgt gca gaa gga cct aaa tgt ggt gaa aac tca gag tgc   1374
His Asn Phe Cys Ala Glu Gly Pro Lys Cys Gly Glu Asn Ser Glu Cys
aaa aac tgg aat aca aaa gct act tgt gag tgc aaa agt ggt tac atc   1422
Lys Asn Trp Asn Thr Lys Ala Thr Cys Glu Cys Lys Ser Gly Tyr Ile
tct gtc cag gga gac tct gcc tac tgt gaa gat att gat gag tgt gca   1470
Ser Val Gln Gly Asp Ser Ala Tyr Cys Glu Asp Ile Asp Glu Cys Ala
gct aag atg cat tac tgt cat gcc aat act gtg tgt gtc aac ctt cct   1518
Ala Lys Met His Tyr Cys His Ala Asn Thr Val Cys Val Asn Leu Pro
ggg tta tat cgc tgt gac tgt gtc cca gga tac att cgt gtg gat gac   1566
Gly Leu Tyr Arg Cys Asp Cys Val Pro Gly Tyr Ile Arg Val Asp Asp
ttc tct tgt aca gaa cac gat gaa tgt ggc agc ggc cag cac aac tgt   1614
Phe Ser Cys Thr Glu His Asp Glu Cys Gly Ser Gly Gln His Asn Cys
gat gag aat gcc atc tgc acc aac act gtg cag gga cac agc tgc acc   1662
Asp Glu Asn Ala Ile Cys Thr Asn Thr Val Gln Gly His Ser Cys Thr
tgc aaa ccg ggc tac gtg ggg aac ggg acc atc tgc aga gct ttc tgt   1710
Cys Lys Pro Gly Tyr Val Gly Asn Gly Thr Ile Cys Arg Ala Phe Cys
gaa gag ggc tgc aga tac ggt gga acg tgt gtg gct ccc aac aaa tgt   1758
Glu Glu Gly Cys Arg Tyr Gly Gly Thr Cys Val Ala Pro Asn Lys Cys
```

-continued

```
gtc tgt cca tct gga ttc aca gga agc cac tgc gag aaa gac att gat    1806
Val Cys Pro Ser Gly Phe Thr Gly Ser His Cys Glu Lys Asp Ile Asp
gaa tgt gcc tta aga act cac acc tgt tgg aac gat tct gcc tgc atc    1854
Glu Cys Ala Leu Arg Thr His Thr Cys Trp Asn Asp Ser Ala Cys Ile
aac ctg gca ggg ggc ttt gac tgt ctc tgc ccc tgg ccc tcc tgc        1902
Asn Leu Ala Gly Gly Phe Asp Cys Leu Cys Pro Ser Gly Pro Ser Cys
tct ggt gac tgt cct cat gaa ggg ggg ctg aag cac aat ggc cag gtg    1950
Ser Gly Asp Cys Pro His Glu Gly Gly Leu Lys His Asn Gly Gln Val
tgg acc ttg aaa gaa gac agg tgt tct gtc tgc tcc aag gat ggc        1998
Trp Thr Leu Lys Glu Asp Arg Cys Ser Val Cys Ser Cys Lys Asp Gly
aag ata ttc tgc cga cgg aca gct tgt gat tgc cag aat cca agt gct    2046
Lys Ile Phe Cys Arg Arg Thr Ala Cys Asp Cys Gln Asn Pro Ser Ala
gac cta ttc tgt tgc cca gaa tgt gac acc aga gtc aca agt caa tgt    2094
Asp Leu Phe Cys Cys Pro Glu Cys Asp Thr Arg Val Thr Ser Gln Cys
tta gac caa aat ggt cac aag ctg tat cga agt gga gac aat tgg acc    2142
Leu Asp Gln Asn Gly His Lys Leu Tyr Arg Ser Gly Asp Asn Trp Thr
cat agc tgt cag cag tgt cgg tgt ctg gaa gga gag gta gat tgc tgg    2190
His Ser Cys Gln Gln Cys Arg Cys Leu Glu Gly Glu Val Asp Cys Trp
cca ctc act tgc ccc aac ttg agc tgt gag tat aca gct atc tta gaa    2238
Pro Leu Thr Cys Pro Asn Leu Ser Cys Glu Tyr Thr Ala Ile Leu Glu
ggg gaa tgt tgt ccc cgc tgt gtc agt gac ccc tgc cta gct gat aac    2286
Gly Glu Cys Cys Pro Arg Cys Val Ser Asp Pro Cys Leu Ala Asp Asn
atc acc tat gac atc aga aaa act tgc ctg gac agc tat ggt gtt tca    2334
Ile Thr Tyr Asp Ile Arg Lys Thr Cys Leu Asp Ser Tyr Gly Val Ser
cgg ctt agt ggc tca gtg tgg acg atg gct gga tct ccc tgc aca acc    2382
Arg Leu Ser Gly Ser Val Trp Thr Met Ala Gly Ser Pro Cys Thr Thr
tgt aaa tgc aag aat gga aga gtc tgt tgt tct gtg gat ttt gag tgt    2430
Cys Lys Cys Lys Asn Gly Arg Val Cys Cys Ser Val Asp Phe Glu Cys
ctt caa aat aat tga agtatttaca gtggactcaa cgcagaagaa tggacgaaat    2485
Leu Gln Asn Asn  *
gaccatccaa cgtgattaag gataggaatc ggtagtttgg ttttttttgtt tgttttgttt    2545
ttttaaccac agataattgc caaagtttcc acctgaggac ggtgtttgga ggttgccttt    2605
tggacctacc actttgctca ttcttgctaa cctagtctag gtgacctaca gtgccgtgca    2665
tttaagtcaa tggttgttaa aagaagtttc ccgtgttgta aatcatgttt ccctatcgg    2725
atcatttgca aatacattta aatgatctca tggtaaatgt tgatgtattt tttggtttat    2785
tttgtgtact aacataatag agagagactc agctcctttt atttattttg ttgatttatg    2845
gatcaaaattc taaaataaag ttgcctgttg tgacttttgt cccatctact gcatacttag    2905
tgctgagatc cctgtaaaat gttttgatga aaatatgtat gtagagtcca gtcgcattat    2965
acatacattt catagtgctg aaccttctta aatgcctact cattcagctt aaacaggctg    3025
aagccaagta tgacaaagag gggaagggcc aaaaacataa tcaaagaata atttttaaaga    3085
gaattcttgt ctctcttgca aaaaaaaaa                                       3114
```

*Homo sapiens* NELL1 isoform 2 amino acid sequence (SEQ ID NO: 4)
```
Met Pro Met Asp Leu Ile Leu Val Val Trp Phe Cys Val Cys Thr Ala Arg
Thr Val Val Gly Phe Gly Met Asp Pro Asp Leu Gln Met Asp Ile Val Thr
Glu Leu Asp Leu Val Asn Thr Thr Leu Gly Val Ala Gln Val Ser Gly Met
His Asn Ala Ser Lys Ala Phe Leu Phe Gln Asp Ile Glu Arg Glu Ile His
Ala Ala Pro His Val Ser Glu Lys Leu Ile Gln Leu Phe Arg Asn Lys Ser
Glu Phe Thr Ile Leu Ala Thr Val Gln Gln Lys Pro Ser Thr Ser Gly Val
Ile Leu Ser Ile Arg Glu Leu Glu His Ser Tyr Phe Glu Leu Glu Ser Ser
Gly Leu Arg Asp Glu Ile Arg Tyr His Tyr Ile His Asn Gly Lys Pro Arg
Thr Glu Ala Leu Pro Tyr Arg Met Ala Asp Gly Gln Trp His Lys Val Ala
Leu Ser Val Ser Ala Ser His Leu Leu Leu His Val Asp Cys Asn Arg Ile
Tyr Glu Arg Val Ile Asp Pro Pro Asp Thr Asn Leu Pro Pro Gly Ile Asn
Leu Trp Leu Gly Gln Arg Asn Gln Lys His Gly Leu Phe Lys Gly Ile Ile
Gln Asp Gly Lys Ile Ile Phe Met Pro Asn Gly Tyr Ile Thr Gln Cys Pro
Asn Leu Asn His Thr Cys Pro Thr Cys Ser Asp Phe Leu Ser Leu Val Gln
Gly Ile Met Asp Leu Gln Glu Leu Leu Ala Lys Met Thr Ala Lys Leu Asn
Tyr Ala Glu Thr Arg Leu Ser Gln Leu Glu Asn Cys His Cys Glu Lys Thr
Cys Gln Val Ser Gly Leu Leu Tyr Arg Asp Gln Asp Ser Trp Val Asp Gly
Asp His Cys Arg Asn Cys Thr Cys Lys Ser Gly Ala Val Glu Cys Arg Arg
Met Ser Cys Pro Pro Leu Asn Cys Ser Pro Asp Ser Leu Pro Val His Ile
Ala Gly Gln Cys Cys Lys Val Cys Arg Pro Lys Cys Ile Tyr Gly Gly Lys
Val Leu Ala Glu Gly Gln Arg Ile Leu Thr Lys Ser Cys Arg Glu Cys Arg
Gly Gly Val Leu Val Lys Ile Thr Glu Met Cys Pro Pro Leu Asn Cys Ser
Glu Lys Asp His Ile Leu Pro Glu Asn Gln Cys Cys Arg Val Cys Arg Gly
His Asn Phe Cys Ala Glu Gly Pro Lys Cys Gly Glu Asn Ser Glu Cys Lys
Asn Trp Asn Thr Lys Ala Thr Cys Glu Cys Lys Ser Gly Tyr Ile Ser Val
Gln Gly Asp Ser Ala Tyr Cys Glu Asp Ile Asp Glu Cys Ala Ala Lys Met
His Tyr Cys His Ala Asn Thr Val Cys Val Asn Leu Pro Gly Leu Tyr Arg
Cys Asp Cys Val Pro Gly Tyr Ile Arg Val Asp Asp Phe Ser Cys Thr Glu
His Asp Glu Cys Gly Ser Gly Gln His Asn Cys Asp Glu Asn Ala Ile Cys
Thr Asn Thr Val Gln Gly His Ser Cys Thr Cys Lys Pro Gly Tyr Val Gly
Asn Gly Thr Ile Cys Arg Ala Phe Cys Glu Glu Gly Cys Arg Tyr Gly Gly
Thr Cys Val Ala Pro Asn Lys Cys Val Cys Pro Ser Gly Phe Thr Gly Ser
His Cys Glu Lys Asp Ile Asp Glu Cys Ala Leu Arg Thr His Thr Cys Trp
Asn Asp Ser Ala Cys Ile Asn Leu Ala Gly Gly Phe Asp Cys Leu Cys Pro
Ser Gly Pro Ser Cys Ser Gly Asp Cys Pro His Glu Gly Gly Leu Lys His
Asn Gly Gln Val Trp Thr Leu Lys Glu Asp Arg Cys Ser Val Cys Ser Cys
```

-continued

```
Lys Asp Gly Lys Ile Phe Cys Arg Arg Thr Ala Cys Asp Cys Gln Asn Pro
Ser Ala Asp Leu Phe Cys Cys Pro Glu Cys Asp Thr Arg Val Thr Ser Gln
Cys Leu Asp Gln Asn Gly His Lys Leu Tyr Arg Ser Gly Asp Asn Trp Thr
His Ser Cys Gln Gln Cys Arg Cys Leu Glu Gly Glu Val Asp Cys Trp Pro
Leu Thr Cys Pro Asn Leu Ser Cys Glu Tyr Thr Ala Ile Leu Glu Gly Glu
Cys Cys Pro Arg Cys Val Ser Asp Pro Cys Leu Ala Asp Asn Ile Thr Tyr
Asp Ile Arg Lys Thr Cys Leu Asp Ser Tyr Gly Val Ser Arg Leu Ser Gly
Ser Val Trp Thr Met Ala Gly Ser Pro Cys Thr Thr Cys Lys Cys Lys Asn
Gly Arg Val Cys Cys Ser Val Asp Phe Glu Cys Leu Gln Asn Asn
```

*Equus caballus* NELL1 isoform 1 nucleotide sequence (SEQ ID NO: 5) and
translated amino acid sequence (SEQ ID NO: 6)

```
atg ggc ttt ggg atg gac ccc gac ctt caa atg gat att atc acc gag      48
Met Gly Phe Gly Met Asp Pro Asp Leu Gln Met Asp Ile Ile Thr Glu
ctc gac ctc gtg aac acc acc ctt gga gtc act cag gtg tcc gga ctg      96
Leu Asp Leu Val Asn Thr Thr Leu Gly Val Thr Gln Val Ser Gly Leu
cac aat gcc agc aaa gca ttt tta ttt caa gat gta gag aga gag atc     144
His Asn Ala Ser Lys Ala Phe Leu Phe Gln Asp Val Glu Arg Glu Ile
cat gca gcc cca cac gtg agt gag aaa tta att cag ctg ttc cgg aat     192
His Ala Ala Pro His Val Ser Glu Lys Leu Ile Gln Leu Phe Arg Asn
aag agt gaa ttc acc ttt ttg gcc act gtg cag cag aag ccg tca act     240
Lys Ser Glu Phe Thr Phe Leu Ala Thr Val Gln Gln Lys Pro Ser Thr
tca gga gtg ata ctg tcc att cga gaa ctg gaa aac agt tat ttt gaa     288
Ser Gly Val Ile Leu Ser Ile Arg Glu Leu Glu Asn Ser Tyr Phe Glu
ctg gag agc agt ggc ctg aga gat gag att cga tat cac tac aca cac     336
Leu Glu Ser Ser Gly Leu Arg Asp Glu Ile Arg Tyr His Tyr Thr His
aag ggg aag ccc agg aca gag gca ctt ccc tac cgg atg gcg gac gga     384
Lys Gly Lys Pro Arg Thr Glu Ala Leu Pro Tyr Arg Met Ala Asp Gly
cgg tgg cac aag gtg gcg ctg tca gtt agc gcc tct cat ctc ctg ctc     432
Arg Trp His Lys Val Ala Leu Ser Val Ser Ala Ser His Leu Leu Leu
cac atc gac tgc aac agg att tat gaa cgt gtg ata gac act cct gag     480
His Ile Asp Cys Asn Arg Ile Tyr Glu Arg Val Ile Asp Thr Pro Glu
acc aac ctc ccc cca gga agc aat ttg tgg ctg ggt cag cga aac caa     528
Thr Asn Leu Pro Pro Gly Ser Asn Leu Trp Leu Gly Gln Arg Asn Gln
aag cac ggc tta ttc aaa gga atc atc caa gat gga aaa atc atc ttc     576
Lys His Gly Leu Phe Lys Gly Ile Ile Gln Asp Gly Lys Ile Ile Phe
atg ccg aat gga tac ata aca cag tgt ccg aac ctg aat cgc act tgc     624
Met Pro Asn Gly Tyr Ile Thr Gln Cys Pro Asn Leu Asn Arg Thr Cys
cca acg tgc agt gat ttc tta agc ctg gtg cag gga atc atg gat ttg     672
Pro Thr Cys Ser Asp Phe Leu Ser Leu Val Gln Gly Ile Met Asp Leu
caa gag ctt ctg gcc aag atg act gcg aaa cta aat tat gca gag aca     720
Gln Glu Leu Leu Ala Lys Met Thr Ala Lys Leu Asn Tyr Ala Glu Thr
cga ctt agt caa ttg gaa aac tgc cac tgc gag aag acc tgt caa gtg     768
Arg Leu Ser Gln Leu Glu Asn Cys His Cys Glu Lys Thr Cys Gln Val
agt gga ctg ctc tat aga gac cag gac tcc tgg gtt gat ggc gat cac     816
Ser Gly Leu Leu Tyr Arg Asp Gln Asp Ser Trp Val Asp Gly Asp His
tgt agg aac tgc acg tgc aaa agg ggc gct gtg gaa tgt cgg agg atg     864
Cys Arg Asn Cys Thr Cys Lys Arg Gly Ala Val Glu Cys Arg Arg Met
tct tgt ccc cct ctc aat tgc tcc cca gac tcc ctc cct gtg cac gtt     912
Ser Cys Pro Pro Leu Asn Cys Ser Pro Asp Ser Leu Pro Val His Val
gcc ggc cag tgc tgt aag gtc tgc cga cca aaa tgt atc tac gga ggg     960
Ala Gly Gln Cys Cys Lys Val Cys Arg Pro Lys Cys Ile Tyr Gly Gly
aaa gtc ctt gca gaa ggc cag cgg att tta acc aag agc tgt cgg gaa    1008
Lys Val Leu Ala Glu Gly Gln Arg Ile Leu Thr Lys Ser Cys Arg Glu
tgc cga ggt gga gtt tta gtg aaa att aca gaa gcg tgc cct cct ttg    1056
Cys Arg Gly Gly Val Leu Val Lys Ile Thr Glu Ala Cys Pro Pro Leu
aac tgc tca gac aag gat cac att ctc cca gag aat cag tgc tgc agc    1104
Asn Cys Ser Asp Lys Asp His Ile Leu Pro Glu Asn Gln Cys Cys Ser
gtc tgc aga ggt cat aac ttt tgt gcg gaa gga cct aaa tgt ggt gaa    1152
Val Cys Arg Gly His Asn Phe Cys Ala Glu Gly Pro Lys Cys Gly Glu
aat tca gag tgc aaa aac tgg aat aca aaa gct act tgc gag tgc aag    1200
Asn Ser Glu Cys Lys Asn Trp Asn Thr Lys Ala Thr Cys Glu Cys Lys
aat ggt tat atc tct gtc cag ggg gac tcc gcc tac tgt gaa gat atc    1248
Asn Gly Tyr Ile Ser Val Gln Gly Asp Ser Ala Tyr Cys Glu Asp Ile
gat gag tgt gct gct aag atg cat tac tgt cgt gcc aat act gtg tgt    1296
Asp Glu Cys Ala Ala Lys Met His Tyr Cys Arg Ala Asn Thr Val Cys
gtc aac ctg cct ggg tta tat cgg tgt gac tgt gtc ccg gga tac att    1344
Val Asn Leu Pro Gly Leu Tyr Arg Cys Asp Cys Val Pro Gly Tyr Ile
cgc gtg gat gat ttc tct tgt aca gaa cat gac gaa tgt ggc agc ggg    1392
Arg Val Asp Asp Phe Ser Cys Thr Glu His Asp Glu Cys Gly Ser Gly
cag cac aac tgt gat gag aat gcc atc tgc acc aac act gtc cag gga    1440
Gln His Asn Cys Asp Glu Asn Ala Ile Cys Thr Asn Thr Val Gln Gly
cac agc tgc acc tgc aaa ccg ggc tac gtg ggg aat ggg acc agc tgc    1488
His Ser Cys Thr Cys Lys Pro Gly Tyr Val Gly Asn Gly Thr Ser Cys
aga gcg ttc tgc gaa gag ggc tgc aga tat ggc ggg aca tgc gtg gct    1536
Arg Ala Phe Cys Glu Glu Gly Cys Arg Tyr Gly Gly Thr Cys Val Ala
cct aac aaa tgt gtc tgt cct tct gga ttc aca gga agc cac tgt gag    1584
Pro Asn Lys Cys Val Cys Pro Ser Gly Phe Thr Gly Ser His Cys Glu
```

-continued

```
aaa gat att gat gaa tgt aca gag gga atc att gag tgc cac aac cat    1632
Lys Asp Ile Asp Glu Cys Thr Glu Gly Ile Ile Glu Cys His Asn His
tcc cgc tgc gtt aac ctg cca ggg tgg tac cac tgt gag tgc aga agc    1680
Ser Arg Cys Val Asn Leu Pro Gly Trp Tyr His Cys Glu Cys Arg Ser
ggt ttc cat gac gat ggg acc tat tca ctg tcc ggg gag tcc tgt att    1728
Gly Phe His Asp Asp Gly Thr Tyr Ser Leu Ser Gly Glu Ser Cys Ile
gac att gat gaa tgt gcc tta aga act cac acc tgt tgg aat gat tct    1776
Asp Ile Asp Glu Cys Ala Leu Arg Thr His Thr Cys Trp Asn Asp Ser
gcc tgc atc aac ttg gca ggg ggc ttc gac tgc ctg tgt ccc tca ggg    1824
Ala Cys Ile Asn Leu Ala Gly Gly Phe Asp Cys Leu Cys Pro Ser Gly
cca tcc tgc tct ggt gac tgc ccc cac gaa gga gga ctg aag cgc aac    1872
Pro Ser Cys Ser Gly Asp Cys Pro His Glu Gly Gly Leu Lys Arg Asn
ggg cag gtg tgg acc ctg aaa gaa gac agg tgt tct gtg tgt tcc tgc    1920
Gly Gln Val Trp Thr Leu Lys Glu Asp Arg Cys Ser Val Cys Ser Cys
aag gat ggg aag ata ttc tgc cga cgg aca gct tgt gat tgc cag aat    1968
Lys Asp Gly Lys Ile Phe Cys Arg Arg Thr Ala Cys Asp Cys Gln Asn
cca agc gtt gac ctt ttc tgt tgc cca gag tgt gac acc agg gtc aca    2016
Pro Ser Val Asp Leu Phe Cys Cys Pro Glu Cys Asp Thr Arg Val Thr
agt caa tgt tta gac caa aat gga cac aag ctc tat cga agt gga gac    2064
Ser Gln Cys Leu Asp Gln Asn Gly His Lys Leu Tyr Arg Ser Gly Asp
aat tgg act cac agc tgt cag cag tgc cgg gtg ctg gaa gga gag gta    2112
Asn Trp Thr His Ser Cys Gln Gln Cys Arg Val Leu Glu Gly Glu Val
gat tgc tgg cca ctc act tgc ccc aga ttg agc tgt gag tac aca gcc    2160
Asp Cys Trp Pro Leu Thr Cys Pro Arg Leu Ser Cys Glu Tyr Thr Ala
atc ttg gaa ggg gag tgt tgt cca cgc tgt gtc agc gac ccc tgc ctg    2208
Ile Leu Glu Gly Glu Cys Cys Pro Arg Cys Val Ser Asp Pro Cys Leu
gcg gat aac atc gtc tat gac atc aga gaa act tgc ctg gac agc tat    2256
Ala Asp Asn Ile Val Tyr Asp Ile Arg Glu Thr Cys Leu Asp Ser Tyr
gga gtt tca agg ctt agt ggc tca gtg tgg aca ttg gct gga tct ccc    2304
Gly Val Ser Arg Leu Ser Gly Ser Val Trp Thr Leu Ala Gly Ser Pro
tgc acg acc tgc aaa tgc aag aat gga agt gtc tgc tgt tct gtg gat    2352
Cys Thr Thr Cys Lys Cys Lys Asn Gly Ser Val Cys Cys Ser Val Asp
ttg gag tgt ctt cat aat aat tga aggatttaaa atggactcat gatcgccaga   2406
Leu Glu Cys Leu His Asn Asn  *
gaaaaatgga caaatgacca tccatgatga tgaaagaaca ggagttggtg ttttttttac  2466
cacagacaat taccaaagtc tccgtctgag gaaggtgttt gcaggttgcc ttttggacct  2526
cccactctgc tcattcttgc taacctagtc taggtgacct acagtgcatt tcagtctatg  2586
gttgttaaaa gaagttttcc gtgttgtaaa tcacgtttcc cttaccaggt cattgcaaat  2646
acatttaaat gatttcatgg taaatgttga tgtatttttt gggtttattt tgtgtactaa  2706
cataatagag attcagctgc ttttatttat ttttttcttg acttttggat caaattcaac  2766
aaataaagtt gcctgttgtg atttt                                       2791
```

*Equus caballus* NELL1 isoform 1 amino acid sequence (SEQ ID NO: 6)

```
Met Gly Phe Gly Met Asp Pro Asp Leu Gln Met Asp Ile Ile Thr Glu Leu
Asp Leu Val Asn Thr Thr Leu Gly Val Thr Gln Val Ser Gly Leu His Asn
Ala Ser Lys Ala Phe Leu Phe Gln Asp Val Glu Arg Glu Ile His Ala Ala
Pro His Val Ser Glu Lys Leu Ile Gln Leu Phe Arg Ala Asn Lys Ser Glu Phe
Thr Phe Leu Ala Thr Val Gln Gln Lys Pro Ser Thr Ser Gly Val Ile Leu
Ser Ile Arg Glu Leu Glu Asn Ser Tyr Phe Glu Leu Glu Ser Ser Gly Leu
Arg Asp Glu Ile Arg Tyr His Tyr Thr His Lys Gly Lys Pro Arg Thr Glu
Ala Leu Pro Tyr Arg Met Ala Asp Gly Arg Trp His Lys Val Ala Leu Ser
Val Ser Ala Ser His Leu Leu Leu His Ile Asp Cys Asn Arg Ile Tyr Glu
Arg Val Ile Asp Thr Pro Glu Thr Asn Leu Pro Pro Gly Ser Asn Leu Trp
Leu Gly Gln Arg Asn Gln Lys His Gly Leu Phe Lys Gly Ile Ile Gln Asp
Gly Lys Ile Ile Phe Met Pro Asn Gly Tyr Ile Thr Gln Cys Pro Asn Leu
Asn Arg Thr Cys Pro Thr Cys Ser Asp Phe Leu Ser Leu Val Gln Gly Ile
Met Asp Leu Gln Glu Leu Leu Ala Lys Met Thr Ala Lys Leu Asn Tyr Ala
Glu Thr Arg Leu Ser Gln Leu Glu Asn Cys His Cys Glu Lys Thr Cys Gln
Val Ser Gly Leu Leu Tyr Arg Asp Gln Asp Ser Trp Val Asp Gly Asp His
Cys Arg Asn Cys Thr Cys Lys Ser Gly Ala Val Glu Cys Arg Arg Met Ser
Cys Pro Pro Leu Asn Cys Ser Pro Asp Ser Leu Pro Val His Val Ala Gly
Gln Cys Cys Lys Val Cys Arg Pro Lys Cys Ile Tyr Gly Gly Lys Val Leu
Ala Glu Gly Gln Arg Ile Leu Thr Lys Ser Cys Arg Glu Cys Arg Gly Gly
Val Leu Val Lys Ile Thr Glu Ala Cys Pro Leu Ala Asn Cys Ser Asp Lys
Asp His Ile Leu Pro Glu Asn Gln Cys Cys Ser Val Cys Arg Gly His Asn
Phe Cys Ala Glu Gly Pro Lys Cys Gly Glu Asn Ser Glu Cys Lys Asn Trp
Asn Thr Lys Ala Thr Cys Glu Cys Lys Asn Gly Tyr Ile Ser Val Gln Gly
Asp Ser Ala Tyr Cys Glu Asp Ile Asp Glu Cys Ala Ala Lys Met His Tyr
Cys Arg Ala Asn Thr Val Cys Val Asn Leu Pro Gly Leu Tyr Arg Cys Asp
Cys Val Pro Gly Tyr Ile Arg Val Asp Asp Phe Ser Cys Thr Glu His Asp
Glu Cys Gly Ser Gly Gln His Asn Cys Asp Glu Asn Ala Ile Cys Thr Asn
Thr Val Gln Gly His Ser Cys Thr Cys Lys Pro Gly Tyr Val Gly Asn Gly
Thr Ser Cys Arg Ala Phe Cys Glu Glu Gly Cys Arg Tyr Gly Gly Thr Cys
Val Ala Pro Asn Lys Cys Val Cys Pro Ser Gly Phe Thr Gly Ser His Cys
Glu Lys Asp Ile Asp Glu Cys Thr Glu Gly Ile Ile Glu Cys His Asn His
Ser Arg Cys Val Asn Leu Pro Gly Trp Tyr His Cys Glu Cys Arg Ser Gly
Phe His Asp Asp Gly Thr Tyr Ser Leu Ser Gly Glu Ser Cys Ile Asp Ile
Asp Glu Cys Ala Leu Arg Thr His Thr Cys Trp Asn Asp Ser Ala Cys Ile
Asn Leu Ala Gly Gly Phe Asp Cys Leu Cys Pro Ser Gly Pro Ser Cys Ser
```

-continued

```
Gly Asp Cys Pro His Glu Gly Gly Leu Lys Arg Asn Gly Gln Val Trp Thr
Leu Lys Glu Asp Arg Cys Ser Val Cys Ser Cys Lys Asp Gly Lys Ile Phe
Cys Arg Arg Thr Ala Cys Asp Cys Gln Asn Pro Ser Val Asp Leu Phe Cys
Cys Pro Glu Cys Asp Thr Arg Val Thr Ser Gln Cys Leu Asp Gln Asn Gly
His Lys Leu Tyr Arg Ser Gly Asp Asn Trp Thr His Ser Cys Gln Gln Cys
Arg Cys Leu Glu Gly Glu Val Asp Cys Trp Pro Leu Thr Cys Pro Arg Leu
Ser Cys Glu Tyr Thr Ala Ile Leu Glu Gly Glu Cys Cys Pro Arg Cys Val
Ser Asp Pro Cys Leu Ala Asp Asn Ile Val Tyr Asp Ile Arg Glu Thr Cys
Leu Asp Ser Tyr Gly Val Ser Arg Leu Ser Gly Ser Val Trp Thr Leu Ala
Gly Ser Pro Cys Thr Thr Cys Lys Cys Lys Asn Gly Ser Val Cys Cys Ser
Val Asp Leu Glu Cys Leu His Asn Asn
```

*Equus caballus* NELL1 isoform 2 nucleotide sequence (SEQ ID NO: 7) and
translated amino acid sequence (SEQ ID NO: 8)

```
atg ggc ttt ggg atg gac ccc gac ctt caa atg gat att atc acc gag      48
Met Gly Phe Gly Met Asp Pro Asp Leu Gln Met Asp Ile Ile Thr Glu
ctc gac ctc gtg aac acc acc ctt gga gtc act cag gtg tcc gga ctg      96
Leu Asp Leu Val Asn Thr Thr Leu Gly Val Thr Gln Val Ser Gly Leu
cac aat gcc agc aaa gca ttt tta ttt caa gat gta gag aga gag atc     144
His Asn Ala Ser Lys Ala Phe Leu Phe Gln Asp Val Glu Arg Glu Ile
cat gca gcc cca cac gtg agt gag aaa tta att cag ctg ttc cgg aat     192
His Ala Ala Pro His Val Ser Glu Lys Leu Ile Gln Leu Phe Arg Asn
aag agt gaa ttc acc ttt ttg gcc act gtg cag cag aag ccg tca act     240
Lys Ser Glu Phe Thr Phe Leu Ala Thr Val Gln Gln Lys Pro Ser Thr
tca gga gtg ata ctg tcc att cga gaa ctg gaa aac agt tat ttt gaa     288
Ser Gly Val Ile Leu Ser Ile Arg Glu Leu Glu Asn Ser Tyr Phe Glu
ctg gag agc agt ggc ctg aga gat gag att cga tat cac tac aca cac     336
Leu Glu Ser Ser Gly Leu Arg Asp Glu Ile Arg Tyr His Tyr Thr His
aag ggg aag ccc agg aca gag gca ctt ccc tac cgg atg gcg gac gga     384
Lys Gly Lys Pro Arg Thr Glu Ala Leu Pro Tyr Arg Met Ala Asp Gly
cgg tgg cac aag gtg gcg ctg tca gtt agc gcc tct cat ctc ctg ctc     432
Arg Trp His Lys Val Ala Leu Ser Val Ser Ala Ser His Leu Leu Leu
cac atc gac tgc aac agg att tat gaa cgt gtg ata gac act cct gag     480
His Ile Asp Cys Asn Arg Ile Tyr Glu Arg Val Ile Asp Thr Pro Glu
acc aac ctc ccc cca gga agc aat ttg tgg ctg ggt cag cga aac caa     528
Thr Asn Leu Pro Pro Gly Ser Asn Leu Trp Leu Gly Gln Arg Asn Gln
aag cac ggc tta ttc aaa gga atc atc caa gat gga aaa atc atc ttc     576
Lys His Gly Leu Phe Lys Gly Ile Ile Gln Asp Gly Lys Ile Ile Phe
atg ccg aat gga tac ata aca cag tgt ccg aac ctc aat cgc act tgc     624
Met Pro Asn Gly Tyr Ile Thr Gln Cys Pro Asn Leu Asn Arg Thr Cys
cca acg tgc agt gat ttc tta agc ctg gtg caa gga atc atg gat tta     672
Pro Thr Cys Ser Asp Phe Leu Ser Leu Val Gln Gly Ile Met Asp Leu
caa gag ctt ctg gcc aag atg act gcg aaa cta aat tat gca gag aca     720
Gln Glu Leu Leu Ala Lys Met Thr Ala Lys Leu Asn Tyr Ala Glu Thr
cga ctt agt caa ttg gaa aac tgc cac tgc gag aag acc tgt caa gtg     768
Arg Leu Ser Gln Leu Glu Asn Cys His Cys Glu Lys Thr Cys Gln Val
agt gga ctg ctc tat aga gac cag gac tcc tgg gtt gat ggc gat cac     816
Ser Gly Leu Leu Tyr Arg Asp Gln Asp Ser Trp Val Asp Gly Asp His
tgt agg aac tgc acg tgc aaa agc ggc gct gtg gaa tgt cgg agg atg     864
Cys Arg Asn Cys Thr Cys Lys Ser Gly Ala Val Glu Cys Arg Arg Met
tct tgt cct cct ctc aat tgc tcc cca gac tcc ctc cct gtg cac gtc     912
Ser Cys Pro Pro Leu Asn Cys Ser Pro Asp Ser Leu Pro Val His Val
gcc ggc cag tgc tgt aag gtc tgc cga cca aaa tgt atc tac gga ggg     960
Ala Gly Gln Cys Cys Lys Val Cys Arg Pro Lys Cys Ile Tyr Gly Gly
aaa gtc ctt gca gaa ggc cag cgg att tta acc aag agc tgt cgg gaa    1008
Lys Val Leu Ala Glu Gly Gln Arg Ile Leu Thr Lys Ser Cys Arg Glu
tgc cga ggt gga gtt tta gtg aaa att aca gaa gcg tgc cct cct ttg    1056
Cys Arg Gly Gly Val Leu Val Lys Ile Thr Glu Ala Cys Pro Pro Leu
aac tgc tca gac aag gat cac att ctc cca gag aat cag tgc tgc agc    1104
Asn Cys Ser Asp Lys Asp His Ile Leu Pro Glu Asn Gln Cys Cys Ser
gtc tgc aga ggt cat aac ttt tgt gcg gaa gga cct aaa tgt ggt gaa    1152
Val Cys Arg Gly His Asn Phe Cys Ala Glu Gly Pro Lys Cys Gly Glu
aat tca gag tgc aaa aac tgg aat aca aaa gct act tgc gag tgc aag    1200
Asn Ser Glu Cys Lys Asn Trp Asn Thr Lys Ala Thr Cys Glu Cys Lys
aat ggt tat atc tct gtc cag ggg gac tcc gcc tac tgt gaa gat atc    1248
Asn Gly Tyr Ile Ser Val Gln Gly Asp Ser Ala Tyr Cys Glu Asp Ile
gat gag tgt gct gct aag atg cat tac tgt cgt gcc aat act gtg tgt    1296
Asp Glu Cys Ala Ala Lys Met His Tyr Cys Arg Ala Asn Thr Val Cys
gtc aac ctg cct ggg tta tat cgg tgt gac tgt gtc ccg gga tac att    1344
Val Asn Leu Pro Gly Leu Tyr Arg Cys Asp Cys Val Pro Gly Tyr Ile
cgc gtg gat gat ttc tct tgt aca gaa cat gac gaa tgt ggc agc ggg    1392
Arg Val Asp Asp Phe Ser Cys Thr Glu His Asp Glu Cys Gly Ser Gly
cag cac aac tgt gat gag aat gcc atc tgc acc aac act gtc cag gga    1440
Gln His Asn Cys Asp Glu Asn Ala Ile Cys Thr Asn Thr Val Gln Gly
cac agc tgc acc tgc aaa ccg ggc tac gtg ggg aat ggg acc agc tgc    1488
His Ser Cys Thr Cys Lys Pro Gly Tyr Val Gly Asn Gly Thr Ser Cys
aga gcg ttc tgc gaa gag ggc tgc aga tat ggc ggg aca tgc gtg gct    1536
Arg Ala Phe Cys Glu Glu Gly Cys Arg Tyr Gly Gly Thr Cys Val Ala
cct aac aaa tgt gtc tgt cct tct gga ttc aca gga agc cac tgt gag    1584
```

-continued

```
Pro Asn Lys Cys Val Cys Pro Ser Gly Phe Thr Gly Ser His Cys Glu
aaa gac att gat gaa tgt gcc tta aga act cac acc tgt tgg aat gat      1632
Lys Asp Ile Asp Glu Cys Ala Leu Arg Thr His Thr Cys Trp Asn Asp
tct gcc tgc atc aac ttg gca ggg ggc ttc gac tgc ctg tgt ccc tca      1680
Ser Ala Cys Ile Asn Leu Ala Gly Gly Phe Asp Cys Leu Cys Pro Ser
ggg cca tcc tgc tct ggt gac tgc ccc cac gaa gga gga ctg aag cgc      1728
Gly Pro Ser Cys Ser Gly Asp Cys Pro His Glu Gly Gly Leu Lys Arg
aac ggg cag gtg tgg acc ctg aaa gaa gac agg tgt tct gtg tgt tcc      1776
Asn Gly Gln Val Trp Thr Leu Lys Glu Asp Arg Cys Ser Val Cys Ser
tgc aag gat ggg aag ata ttc tgc cga cgg aca gct tgt gat tgc cag      1824
Cys Lys Asp Gly Lys Ile Phe Cys Arg Arg Thr Ala Cys Asp Cys Gln
aat cca agc gtt gac ctt ttc tgt tgc cca gag tgt gac acc agg gtc      1872
Asn Pro Ser Val Asp Leu Phe Cys Cys Pro Glu Cys Asp Thr Arg Val
aca agt caa tgt tta gac caa aat gga cac aag ctc tat cga agt gga      1920
Thr Ser Gln Cys Leu Asp Gln Asn Gly His Lys Leu Tyr Arg Ser Gly
gac aat tgg act cac agc tgt cag cag tgc cgg tgt ctg gaa gga gag      1968
Asp Asn Trp Thr His Ser Cys Gln Gln Cys Arg Cys Leu Glu Gly Glu
gta gat tgc tgg cca ctc act tgc ccc aga ttg agc tgt gag tac aca      2016
Val Asp Cys Trp Pro Leu Thr Cys Pro Arg Leu Ser Cys Glu Tyr Thr
gcc atc ttg gaa ggg gag tgt tgt cca cgc tgt gtc agc gac ccc tgc      2064
Ala Ile Leu Glu Gly Glu Cys Cys Pro Arg Cys Val Ser Asp Pro Cys
ctg gcg gat aac atc gtc tat gac atc aga gaa act tgc ctg gac agc      2112
Leu Ala Asp Asn Ile Val Tyr Asp Ile Arg Glu Thr Cys Leu Asp Ser
tat gga gtt tca agg ctt agt ggc tca gtg tgg aca ttg gct gga tct      2160
Tyr Gly Val Ser Arg Leu Ser Gly Ser Val Trp Thr Leu Ala Gly Ser
ccc tgc acg acc tgc aaa tgc aag aat gga agt gtc tgt tct gtg           2208
Pro Cys Thr Thr Cys Lys Cys Lys Asn Gly Ser Val Cys Cys Ser Val
gat ttg gag tgt ctt cat aat aat tga aggatttaaa atggactcat             2255
Asp Leu Glu Cys Leu His Asn Asn *
gatcgccaga gaaaaatgga caaatgacca                                      2285
```

*Equus caballus* NELL1 isoform 2 amino acid sequence (SEQ ID NO: 8)

```
Met Gly Phe Gly Met Asp Pro Asp Leu Gln Met Asp Ile Ile Thr Glu Leu
Asp Leu Val Asn Thr Thr Leu Gly Val Thr Gln Val Ser Gly Leu His Asn
Ala Ser Lys Ala Phe Leu Phe Gln Asp Val Glu Arg Glu Ile His Ala Ala
Pro His Val Ser Glu Lys Leu Ile Gln Leu Phe Arg Asn Lys Ser Glu Phe
Thr Phe Leu Ala Thr Val Gln Gln Lys Pro Ser Thr Ser Gly Val Ile Leu
Ser Ile Arg Glu Leu Glu Asn Ser Tyr Phe Glu Leu Glu Ser Ser Gly Leu
Arg Asp Glu Ile Arg Tyr His Tyr Thr His Lys Gly Lys Pro Arg Thr Glu
Ala Leu Pro Tyr Arg Met Ala Asp Gly Arg Trp His Lys Val Ala Leu Ser
Val Ser Ala Ser His Leu Leu Leu His Ile Asp Cys Asn Arg Ile Tyr Glu
Arg Val Ile Asp Thr Pro Glu Thr Asn Leu Pro Pro Gly Ser Asn Leu Trp
Leu Gly Gln Arg Asn Gln Lys His Gly Leu Phe Lys Gly Ile Ile Gln Asp
Gly Lys Ile Ile Phe Met Pro Asn Gly Tyr Ile Thr Gln Cys Pro Asn Leu
Asn Arg Thr Cys Pro Thr Cys Ser Asp Phe Leu Ser Leu Val Gln Gly Ile
Met Asp Leu Gln Glu Leu Leu Ala Lys Met Thr Ala Lys Leu Asn Tyr Ala
Glu Thr Arg Leu Ser Gln Leu Glu Asn Cys His Cys Glu Lys Thr Cys Gln
Val Ser Gly Leu Leu Tyr Arg Asp Gln Asp Ser Trp Val Asp Gly Asp His
Cys Arg Asn Cys Thr Cys Lys Ser Gly Ala Val Glu Cys Arg Arg Met Ser
Cys Pro Pro Leu Asn Cys Ser Pro Asp Ser Leu Pro Val His Val Ala Gly
Gln Cys Cys Lys Val Cys Arg Pro Lys Cys Ile Tyr Gly Gly Lys Val Leu
Ala Glu Gly Gln Arg Ile Leu Thr Lys Ser Cys Arg Glu Cys Arg Gly Gly
Val Leu Val Lys Ile Thr Glu Ala Cys Pro Pro Leu Asn Cys Ser Asp Lys
Asp His Ile Leu Pro Glu Asn Gln Cys Cys Ser Val Cys Arg Gly His Asn
Phe Cys Ala Glu Gly Pro Lys Cys Gly Glu Asn Ser Glu Cys Lys Asn Trp
Asn Thr Lys Ala Thr Cys Glu Cys Lys Asn Gly Tyr Ile Ser Val Gln Gly
Asp Ser Ala Tyr Cys Glu Asp Ile Asp Glu Cys Ala Ala Lys Met His Tyr
Cys Arg Ala Asn Thr Val Cys Val Asn Leu Pro Gly Leu Tyr Arg Cys Asp
Cys Val Pro Gly Tyr Ile Arg Val Asp Asp Phe Ser Cys Thr Glu His Asp
Glu Cys Gly Ser Gly Gln His Asn Cys Asp Glu Asn Ala Ile Cys Thr Asn
Thr Val Gln Gly His Ser Cys Thr Cys Lys Pro Gly Tyr Val Gly Asn Gly
Thr Ser Cys Arg Ala Phe Cys Glu Glu Gly Cys Arg Tyr Gly Gly Thr Cys
Val Ala Pro Asn Lys Cys Val Cys Pro Ser Gly Phe Thr Gly Ser His Cys
Glu Lys Asp Ile Asp Glu Cys Ala Leu Arg Thr His Thr Cys Trp Asn Asp
Ser Ala Cys Ile Asn Leu Ala Gly Gly Phe Asp Cys Leu Cys Pro Ser Gly
Pro Ser Cys Ser Gly Asp Cys Pro His Glu Gly Gly Leu Lys Arg Asn Gly
Gln Val Trp Thr Leu Lys Glu Asp Arg Cys Ser Val Cys Ser Cys Lys Asp
Gly Lys Ile Phe Cys Arg Arg Thr Ala Cys Asp Cys Gln Asn Pro Ser Val
Asp Leu Phe Cys Cys Pro Glu Cys Asp Thr Arg Val Thr Ser Gln Cys Leu
Asp Gln Asn Gly His Lys Leu Tyr Arg Ser Gly Asp Asn Trp Thr His Ser
Cys Gln Gln Cys Arg Cys Leu Glu Gly Glu Val Asp Cys Trp Pro Leu Thr
Cys Pro Arg Leu Ser Cys Glu Tyr Thr Ala Ile Leu Glu Gly Glu Cys Cys
Pro Arg Cys Val Ser Asp Pro Cys Leu Ala Asp Asn Ile Val Tyr Asp Ile
Arg Glu Thr Cys Leu Asp Ser Tyr Gly Val Ser Arg Leu Ser Gly Ser Val
Trp Thr Leu Ala Gly Ser Pro Cys Thr Thr Cys Lys Cys Lys Asn Gly Ser
Val Cys Cys Ser Val Asp Leu Glu Cys Leu His Asn Asn
```

*Mus musculus* NELL1 nucleotide sequence (SEQ ID NO: 9) and translated
amino acid sequence SEQ ID NO: 10)

```
gcgttggtgc gccctgcttg gcggggggcc tccggagcg atg ccg atg gat gtg        54
                                            Met Pro Met Asp Val
att tta gtt ttg tgg ttc tgt gtg tgc acc gcc agg aca gtg ctg ggc      102
Ile Leu Val Leu Trp Phe Cys Val Cys Thr Ala Arg Thr Val Leu Gly
ttt ggg atg gac cct gac ctt cag atg gac atc atc act gaa ctt gac      150
Phe Gly Met Asp Pro Asp Leu Gln Met Asp Ile Ile Thr Glu Leu Asp
ctt gtg aac acc acc ctg ggc gtc act cag gtg gct gga cta cac aat      198
Leu Val Asn Thr Thr Leu Gly Val Thr Gln Val Ala Gly Leu His Asn
gcc agt aag gca ttt ctg ttt caa gat gta cag aga gag atc cac tca      246
Ala Ser Lys Ala Phe Leu Phe Gln Asp Val Gln Arg Glu Ile His Ser
gcc cct cat gtg agt gag aag ctg atc cag cta ttc cgg aat aag agt      294
Ala Pro His Val Ser Glu Lys Leu Ile Gln Leu Phe Arg Asn Lys Ser
gag ttt acc ttt ttg gct aca gtg cag cag aag ccg tcc acc tca ggg      342
Glu Phe Thr Phe Leu Ala Thr Val Gln Gln Lys Pro Ser Thr Ser Gly
gtg ata ctg tcg atc cgg gag ctg gaa cac agc tat ttt gaa ctg gag      390
Val Ile Leu Ser Ile Arg Glu Leu Glu His Ser Tyr Phe Glu Leu Glu
agc agt ggc cca aga gaa gag atc cgc tat cat tac atc cat ggc ggc      438
Ser Ser Gly Pro Arg Glu Glu Ile Arg Tyr His Tyr Ile His Gly Gly
aag ccc agg act gag gcc ctt ccc tac cgc atg gcc gat gga cag tgg      486
Lys Pro Arg Thr Glu Ala Leu Pro Tyr Arg Met Ala Asp Gly Gln Trp
cac aag gtc gcg ctg tct gtg agc gcc tct cac ctc cta ctc cat gtc      534
His Lys Val Ala Leu Ser Val Ser Ala Ser His Leu Leu Leu His Val
gac tgc aat agg att tat gag cgt gtg ata gat cct ccg gag acc aac      582
Asp Cys Asn Arg Ile Tyr Glu Arg Val Ile Asp Pro Pro Glu Thr Asn
ctt cct cca gga agc aat cta tgg ctt ggg caa cgt aat caa aag cat      630
Leu Pro Pro Gly Ser Asn Leu Trp Leu Gly Gln Arg Asn Gln Lys His
ggc ttt ttc aaa gga atc atc caa gat ggc aag atc atc ttc atg ccg      678
Gly Phe Phe Lys Gly Ile Ile Gln Asp Gly Lys Ile Ile Phe Met Pro
aac ggc ttc atc aca cag tgt ccc aac cta aat cgc act tgc cca aca      726
Asn Gly Phe Ile Thr Gln Cys Pro Asn Leu Asn Arg Thr Cys Pro Thr
tgc agt gat ttc ctg agc ctg gtt caa gga ata atg gat ttg caa gag      774
Cys Ser Asp Phe Leu Ser Leu Val Gln Gly Ile Met Asp Leu Gln Glu
ctt ttg gcc aag atg act gca aaa ctg aat tat gca gag acg aga ctt      822
Leu Leu Ala Lys Met Thr Ala Lys Leu Asn Tyr Ala Glu Thr Arg Leu
ggt caa ctg gaa aat tgc cac tgt gag aag acc tgc caa gtg agt ggg      870
Gly Gln Leu Glu Asn Cys His Cys Glu Lys Thr Cys Gln Val Ser Gly
ctg ctc tac agg gac caa gac tcc tgg gta gat ggt gac aac tgc agg      918
Leu Leu Tyr Arg Asp Gln Asp Ser Trp Val Asp Gly Asp Asn Cys Arg
aac tgc aca tgc aaa agt ggt gct gtg gag tgc cga agg atg tcc tgt      966
Asn Cys Thr Cys Lys Ser Gly Ala Val Glu Cys Arg Arg Met Ser Cys
ccc cca ctc aac tgt tcc cca gac tca ctt cct gtg cat att tct ggc     1014
Pro Pro Leu Asn Cys Ser Pro Asp Ser Leu Pro Val His Ile Ser Gly
caa tgt tgt aaa gtt tgc aga cca aaa tgt atc tat gga gga aaa gtt     1062
Gln Cys Cys Lys Val Cys Arg Pro Lys Cys Ile Tyr Gly Gly Lys Val
ctt gct gag ggc cag cgg att tta acc aag acc tgc cgg gaa tgt cga     1110
Leu Ala Glu Gly Gln Arg Ile Leu Thr Lys Thr Cys Arg Glu Cys Arg
ggt gga gtc ttg gta aaa atc aca gaa gct tgc cct cct ttg aac tgc     1158
Gly Gly Val Leu Val Lys Ile Thr Glu Ala Cys Pro Pro Leu Asn Cys
tca gag aag gat cat att ctt ccg gag aac cag tgc tgc agg gtc tgc     1206
Ser Glu Lys Asp His Ile Leu Pro Glu Asn Gln Cys Cys Arg Val Cys
cga ggt cat aac ttc tgt gca gaa gca cct aag tgt gga gaa aac tcg     1254
Arg Gly His Asn Phe Cys Ala Glu Ala Pro Lys Cys Gly Glu Asn Ser
gaa tgc aaa aat tgg aat aca aaa gcg act tgt gag tgc aag aat gga     1302
Glu Cys Lys Asn Trp Asn Thr Lys Ala Thr Cys Glu Cys Lys Asn Gly
tac atc tct gtc cag ggc aac tct gca tac tgt gaa gat atc gat gag     1350
Tyr Ile Ser Val Gln Gly Asn Ser Ala Tyr Cys Glu Asp Ile Asp Glu
tgt gca gca aag atg cac tac tgt cat gcc aac acg gtg tgt gtc aac     1398
Cys Ala Ala Lys Met His Tyr Cys His Ala Asn Thr Val Cys Val Asn
ttg ccg ggg tta tat cgc tgt gac tgc atc cca gga tac atc cgt gtg     1446
Leu Pro Gly Leu Tyr Arg Cys Asp Cys Ile Pro Gly Tyr Ile Arg Val
gat gac ttc tct tgt acg gag cat gat gat tgt ggc agc gga caa cac     1494
Asp Asp Phe Ser Cys Thr Glu His Asp Asp Cys Gly Ser Gly Gln His
aac tgt gac aaa aat gcc atc tgt acc aac aca gtc cag gga cac agc     1542
Asn Cys Asp Lys Asn Ala Ile Cys Thr Asn Thr Val Gln Gly His Ser
tgt acc tgc cag cca ggc tac gtg gga aat ggt act gtc tgc aaa gca     1590
Cys Thr Cys Gln Pro Gly Tyr Val Gly Asn Gly Thr Val Cys Lys Ala
ttc tgt gaa gag ggt tgc aga tac gga ggt acc tgt gtg gcc cct aac     1638
Phe Cys Glu Glu Gly Cys Arg Tyr Gly Gly Thr Cys Val Ala Pro Asn
aaa tgt gtc tgt cct tct gga ttc aca gga agc cac tgt gag aaa gat     1686
Lys Cys Val Cys Pro Ser Gly Phe Thr Gly Ser His Cys Glu Lys Asp
att gat gaa tgt gca gag gga ttc gtt gag tgc cac aac cac tcc cgc     1734
Ile Asp Glu Cys Ala Glu Gly Phe Val Glu Cys His Asn His Ser Arg
tgc gtt aac ctt cca ggg tgg tac cac tgt gag tgc aga agc ggt ttc     1782
Cys Val Asn Leu Pro Gly Trp Tyr His Cys Glu Cys Arg Ser Gly Phe
```

-continued

```
cat gac gat ggg acc tat tca ctg tcc ggg gag tcc tgc att gat att      1830
His Asp Asp Gly Thr Tyr Ser Leu Ser Gly Glu Ser Cys Ile Asp Ile
gat gaa tgt gcc tta aga act cac act tgt tgg aat gac tct gcc tgc      1878
Asp Glu Cys Ala Leu Arg Thr His Thr Cys Trp Asn Asp Ser Ala Cys
atc aac tta gca gga gga ttt gac tgc ctg tgt ccc tct ggg ccc tcc      1926
Ile Asn Leu Ala Gly Gly Phe Asp Cys Leu Cys Pro Ser Gly Pro Ser
tgc tct ggt gac tgt ccc cac gaa ggg ggg ctg aag cat aat ggg cag      1974
Cys Ser Gly Asp Cys Pro His Glu Gly Gly Leu Lys His Asn Gly Gln
gtg tgg att ctg aga gaa gac agg tgt tca gtc tgt tcc tgt aag gat      2022
Val Trp Ile Leu Arg Glu Asp Arg Cys Ser Val Cys Ser Cys Lys Asp
ggg aag ata ttc tgc cgg cgg aca gct tgt gat tgc cag aat cca aat      2070
Gly Lys Ile Phe Cys Arg Arg Thr Ala Cys Asp Cys Gln Asn Pro Asn
gtt gac ctt ttc tgc tgc cca gag tgt gac acc agg gtc act agc caa      2118
Val Asp Leu Phe Cys Cys Pro Glu Cys Asp Thr Arg Val Thr Ser Gln
tgt tta gat caa agc gga cag aag ctc tat cga agt gga gac aac tgg      2166
Cys Leu Asp Gln Ser Gly Gln Lys Leu Tyr Arg Ser Gly Asp Asn Trp
acc cac agc tgc cag cag tgc cga tgt ctg gaa gga gag gca gac tgc      2214
Thr His Ser Cys Gln Gln Cys Arg Cys Leu Glu Gly Glu Ala Asp Cys
tgg cct cta gct tgc cct agt ttg agc tgt gaa tac aca gcc atc ttt      2262
Trp Pro Leu Ala Cys Pro Ser Leu Ser Cys Glu Tyr Thr Ala Ile Phe
gaa gga gag tgt tgt ccc cgc tgt gtc agt gac ccc tgc ctg gct gat      2310
Glu Gly Glu Cys Cys Pro Arg Cys Val Ser Asp Pro Cys Leu Ala Asp
aat att gcc tat gac atc aga aaa act tgc ctg gac agc tct ggt att      2358
Asn Ile Ala Tyr Asp Ile Arg Lys Thr Cys Leu Asp Ser Ser Gly Ile
tcg agg ctg agc ggc gca gtg tgg aca atg gct gga tct ccc tgt aca      2406
Ser Arg Leu Ser Gly Ala Val Trp Thr Met Ala Gly Ser Pro Cys Thr
acc tgt caa tgc aag aat ggg aga gtc tgc tgc tct gtg gat ctg gtg      2454
Thr Cys Gln Cys Lys Asn Gly Arg Val Cys Cys Ser Val Asp Leu Val
tgt ctt gag aat aac tga agattttaaa tggactcatc acatgagaaa            2502
Cys Leu Glu Asn Asn *
atggacaaaa tgaccatcca acctgaggaa gaggaggggc tgatttcttt ttctttttaa   2562
ccacagtcaa ttaccaaagt ctccatcaga ggaaggcgtt tgggttgcct ttaccacttt   2622
gctcatcctt gctgacctag tctagatgcc tgcagtaccg tgtatttcgg tcgatggttg   2682
ttgagtctcc gtgctgtaaa tcacatttcc cttgtcagat catttacaga tacatttaaa   2742
ggattccatg ataatgtta aagtaccttt tgtttatttt gtgtaccaac ataatagaga    2802
cttggcacca                                                         2812
```

Mus musculus NELL1 amino acid sequence (SEQ ID NO: 10)

```
Met Pro Met Asp Val Ile Leu Val Leu Trp Phe Cys Val Cys Thr Ala Arg
Thr Val Leu Gly Phe Gly Met Asp Pro Asp Leu Gln Met Asp Ile Ile Thr
Glu Leu Asp Leu Val Asn Thr Thr Leu Gly Val Thr Gln Val Ala Gly Leu
His Asn Ala Ser Lys Ala Phe Leu Phe Gln Asp Val Gln Arg Glu Ile His
Ser Ala Pro His Val Ser Glu Lys Leu Ile Glu Leu Phe Arg Asn Lys Ser
Glu Phe Thr Phe Leu Ala Thr Val Gln Gln Lys Pro Ser Thr Ser Gly Val
Ile Leu Ser Ile Arg Glu Leu Glu His Ser Tyr Phe Glu Leu Glu Ser Ser
Gly Pro Arg Glu Glu Ile Arg Tyr His Tyr Ile His Gly Gly Lys Pro Arg
Thr Glu Ala Leu Pro Tyr Arg Met Ala Asp Gly Trp His Lys Val Ala
Leu Ser Val Ser Ala Ser His Leu Leu Leu His Val Asp Cys Asn Arg Ile
Tyr Glu Arg Val Ile Asp Pro Pro Glu Thr Asn Leu Pro Pro Gly Ser Asn
Leu Trp Leu Gly Gln Arg Asn Gln Lys His Gly Phe Phe Lys Gly Ile Ile
Gln Asp Gly Lys Ile Ile Phe Met Pro Asn Gly Tyr Ile Thr Gln Cys Pro
Asn Leu Asn Arg Thr Cys Pro Thr Cys Ser Asp Phe Leu Ser Leu Val Gln
Gly Ile Met Asp Leu Gln Glu Leu Leu Ala Lys Met Thr Ala Lys Leu Asn
Tyr Ala Glu Thr Arg Leu Gly Gln Leu Glu Asn Cys His Cys Glu Lys Thr
Cys Gln Val Ser Gly Leu Leu Tyr Arg Asp Gln Asp Ser Trp Val Asp Gly
Asp Asn Cys Arg Asn Cys Thr Cys Lys Ser Gly Ala Val Glu Cys Arg Arg
Met Ser Cys Pro Pro Leu Asn Cys Ser Pro Asp Ser Leu Pro Val His Ile
Ser Gly Gln Cys Cys Lys Val Cys Arg Pro Lys Cys Ile Tyr Gly Gly Lys
Val Leu Ala Glu Gly Gln Arg Ile Leu Thr Lys Thr Cys Arg Glu Cys Arg
Gly Gly Val Leu Val Lys Ile Thr Glu Ala Cys Pro Pro Leu Asn Cys Ser
Glu Lys Asp His Ile Leu Pro Glu Asn Gln Cys Cys Arg Val Cys Arg Gly
His Asn Phe Cys Ala Glu Ala Pro Lys Cys Gly Glu Asn Ser Glu Cys Lys
Asn Trp Asn Thr Lys Ala Thr Cys Glu Cys Lys Asn Gly Tyr Ile Ser Val
Gln Gly Asn Ser Ala Tyr Cys Glu Asp Ile Asp Glu Cys Ala Ala Lys Met
His Tyr Cys His Ala Asn Thr Val Cys Val Asn Leu Pro Gly Leu Tyr Arg
Cys Asp Cys Ile Pro Gly Tyr Ile Arg Val Asp Asp Phe Ser Cys Thr Glu
His Asp Asp Cys Gly Ser Gly Gln His Asn Cys Asp Lys Asn Ala Ile Cys
Thr Asn Thr Val Gln Gly His Ser Cys Thr Cys Pro Tyr Val Gly
Asn Gly Thr Val Cys Lys Ala Phe Cys Glu Glu Gly Cys Arg Tyr Gly Gly
Thr Cys Val Ala Pro Asn Lys Cys Val Cys Pro Ser Gly Phe Thr Gly Ser
His Cys Glu Lys Asp Ile Asp Glu Cys Ala Glu Gly Phe Val Glu Cys His
Asn His Ser Arg Cys Val Asn Leu Pro Gly Trp Tyr His Cys Glu Cys Arg
Ser Gly Phe His Asp Asp Gly Thr Tyr Ser Leu Ser Gly Glu Ser Cys Ile
Asp Ile Asp Glu Cys Ala Leu Arg Thr His Thr Cys Trp Asn Asp Ser Ala
Cys Ile Asn Leu Ala Gly Gly Phe Asp Cys Leu Cys Pro Ser Gly Pro Ser
Cys Ser Gly Asp Cys Pro His Glu Gly Gly Leu Lys His Asn Gly Gln Val
Trp Ile Leu Arg Glu Asp Arg Cys Ser Val Cys Ser Cys Lys Asp Gly Lys
Ile Phe Cys Arg Arg Thr Ala Cys Asp Cys Gln Asn Pro Asn Val Asp Leu
Phe Cys Cys Pro Glu Cys Asp Thr Arg Val Thr Ser Gln Cys Leu Asp Gln
```

```
Ser Gly Gln Lys Leu Tyr Arg Ser Gly Asp Asn Trp Thr His Ser Cys Gln
Gln Cys Arg Cys Leu Glu Gly Glu Ala Asp Cys Trp Pro Leu Ala Cys Pro
Ser Leu Ser Cys Glu Tyr Thr Ala Ile Phe Glu Gly Glu Cys Cys Pro Arg
Cys Val Ser Asp Pro Cys Leu Ala Asp Asn Ile Ala Tyr Asp Ile Arg Lys
Thr Cys Leu Asp Ser Ser Gly Ile Ser Arg Leu Ser Gly Ala Val Trp Thr
Met Ala Gly Ser Pro Cys Thr Thr Cys Gln Cys Lys Asn Gly Arg Val Cys
Cys Ser Val Asp Leu Val Cys Leu Glu Asn Asn
```

*Rattus norvegicus* NELL1 nucleotide sequence (SEQ ID NO: 11) and
translated amino acid sequence (SEQ ID NO: 12)

```
aagcactggt tcttgttag cgttggtgcg ccctgcttgg cggggggttct ccggagcg            58
atg ccg atg gat gtg att tta gtt ttg tgg ttc tgt gta tgc acc gcc         106
Met Pro Met Asp Val Ile Leu Val Leu Trp Phe Cys Val Cys Thr Ala
agg aca gtg ttg ggc ttt ggg atg gac cct gac ctt cag ctg gac atc         154
Arg Thr Val Leu Gly Phe Gly Met Asp Pro Asp Leu Gln Leu Asp Ile
atc tca gag ctc gac ctg gtg aac acc acc ctg gga gtc acg cag gtg         202
Ile Ser Glu Leu Asp Leu Val Asn Thr Thr Leu Gly Val Thr Gln Val
gct gga ctg cac aac gcc agt aaa gca ttt cta ttt caa gat gta cag         250
Ala Gly Leu His Asn Ala Ser Lys Ala Phe Leu Phe Gln Asp Val Gln
aga gag atc cat tcg gcc cct cac gtg agt gag aag ctg atc cag cta         298
Arg Glu Ile His Ser Ala Pro His Val Ser Glu Lys Leu Ile Gln Leu
ttc cgg aat aag agc gag ttc acc ttt ttg gct aca gtg cag cag aaa         346
Phe Arg Asn Lys Ser Glu Phe Thr Phe Leu Ala Thr Val Gln Gln Lys
cca tcc acc tca ggg gtg ata ctg tcc atc cgg gag ctg gag cac agc         394
Pro Ser Thr Ser Gly Val Ile Leu Ser Ile Arg Glu Leu Glu His Ser
tat ttt gaa ctg gag agc agt ggc cca aga gaa ata cgc tac cat              442
Tyr Phe Glu Leu Glu Ser Ser Gly Pro Arg Glu Ile Arg Tyr His
tac ata cat ggt gga aag ccc agg act gag gcc ctt ccc tac cgc atg         490
Tyr Ile His Gly Gly Lys Pro Arg Thr Glu Ala Leu Pro Tyr Arg Met
gca gac gga caa tgg cac aag gtc gcg ctg tca gtg agc gcc tct cac         538
Ala Asp Gly Gln Trp His Lys Val Ala Leu Ser Val Ser Ala Ser His
ctc ctg ctc cac atc gac tgc aat agg att tac gag cgt gtg ata gac         586
Leu Leu Leu His Ile Asp Cys Asn Arg Ile Tyr Glu Arg Val Ile Asp
cct ccg gag acc aac ctt cct cca gga agc aat ctg tgg ctt ggg caa         634
Pro Pro Glu Thr Asn Leu Pro Pro Gly Ser Asn Leu Trp Leu Gly Gln
cgt aac caa aag cat ggc ttt ttc aaa gga atc atc caa gat ggt aag         682
Arg Asn Gln Lys His Gly Phe Phe Lys Gly Ile Ile Gln Asp Gly Lys
atc atc ttc atg ccg aat ggt ttc atc aca cag tgt ccc aac ctc aat         730
Ile Ile Phe Met Pro Asn Gly Phe Ile Thr Gln Cys Pro Asn Leu Asn
cgc act tgc cca aca tgc agt gac ttc ctg agc ctg gtt caa gga ata         778
Arg Thr Cys Pro Thr Cys Ser Asp Phe Leu Ser Leu Val Gln Gly Ile
atg gat ttg caa gag ctt ttg gcc aag atg act gca aaa ctg aat tat         826
Met Asp Leu Gln Glu Leu Leu Ala Lys Met Thr Ala Lys Leu Asn Tyr
gca gag acg aga ctt ggt caa ctg gaa aat tgc cac tgt gag aag acc         874
Ala Glu Thr Arg Leu Gly Gln Leu Glu Asn Cys His Cys Glu Lys Thr
tgc caa gtg agt ggg ctg ctc tac agg gac caa gac tcc tgg gtg gat         922
Cys Gln Val Ser Gly Leu Leu Tyr Arg Asp Gln Asp Ser Trp Val Asp
ggt gac aac tgt ggg aac tgc acg tgc aaa agt ggt gcc gtg gag tgc         970
Gly Asp Asn Cys Gly Asn Cys Thr Cys Lys Ser Gly Ala Val Glu Cys
cgc agg atg tcc tgt ccc ccg ctc aac tgt tcc ccg gac tca ctt cct        1018
Arg Arg Met Ser Cys Pro Pro Leu Asn Cys Ser Pro Asp Ser Leu Pro
gtg cac att tcc ggc cag tgt tgt aaa gtt tgc aga cca aaa tgt atc        1066
Val His Ile Ser Gly Gln Cys Cys Lys Val Cys Arg Pro Lys Cys Ile
tat gga gga aaa gtt ctt gct gag ggc cag cgg att tta acc aag acc        1114
Tyr Gly Gly Lys Val Leu Ala Glu Gly Gln Arg Ile Leu Thr Lys Thr
tgc cgg gaa tgt cga ggt gga gtc ttg gta aaa atc aca gaa gct tgc        1162
Cys Arg Glu Cys Arg Gly Gly Val Leu Val Lys Ile Thr Glu Ala Cys
cct cct ttg aac tgc tca gca aag gat cat att ctt cca gag aat cag        1210
Pro Pro Leu Asn Cys Ser Ala Lys Asp His Ile Leu Pro Glu Asn Gln
tgc tgc agg gtc tgc cca ggt cat aac ttc tgt gca gaa gca cct aag        1258
Cys Cys Arg Val Cys Pro Gly His Asn Phe Cys Ala Glu Ala Pro Lys
tgc gga gaa aac tcg gaa tgc aaa aat tgg aat aca aaa gca acc tgt        1306
Cys Gly Glu Asn Ser Glu Cys Lys Asn Trp Asn Thr Lys Ala Thr Cys
gag tgc aag aat tac atc tct gtc cag ggc aat tct gca tac tgt            1354
Glu Cys Lys Asn Gly Tyr Ile Ser Val Gln Gly Asn Ser Ala Tyr Cys
gaa gat att gat gag tgt gca gct aaa atg cac tat tgt cat gcc aac        1402
Glu Asp Ile Asp Glu Cys Ala Ala Lys Met His Tyr Cys His Ala Asn
acc gtg tgt gtc aac ttg ccg ggg ttg tat cgc tgt gac tgc gtc cca        1450
Thr Val Cys Val Asn Leu Pro Gly Leu Tyr Arg Cys Asp Cys Val Pro
ggg tac atc cgt gtg gat gac ttc tct tgt acg gag cat gat gat tgt        1498
Gly Tyr Ile Arg Val Asp Asp Phe Ser Cys Thr Glu His Asp Asp Cys
ggc agc gga caa cac aac tgc gac aaa aat gcc atc tgt acc aac aca        1546
Gly Ser Gly Gln His Asn Cys Asp Lys Asn Ala Ile Cys Thr Asn Thr
gtc cag gga cac agc tgc acc tgc cag ccg ggt tat gtg gga aat ggc        1594
Val Gln Gly His Ser Cys Thr Cys Gln Pro Gly Tyr Val Gly Asn Gly
acc atc tgc aaa gca ttc tgt gaa gag ggt tgc aga tac gga ggt acc        1642
Thr Ile Cys Lys Ala Phe Cys Glu Glu Gly Cys Arg Tyr Gly Gly Thr
tgt gtg gct cct aac aag tgt gtc tgt cct tct gga ttc acg gga agc        1690
Cys Val Ala Pro Asn Lys Cys Val Cys Pro Ser Gly Phe Thr Gly Ser
```

-continued

```
cac tgt gag aaa gat att gat gaa tgc gca gag gga ttc gtt gaa tgc    1738
His Cys Glu Lys Asp Ile Asp Glu Cys Ala Glu Gly Phe Val Glu Cys
cac aac tac tcc cgc tgt gtt aac ctg cca ggg tgg tac cac tgt gag    1786
His Asn Tyr Ser Arg Cys Val Asn Leu Pro Gly Trp Tyr His Cys Glu
tgc aga agc ggt ttc cat gac gat ggg acc tac tca ctg tcc gag        1834
Cys Arg Ser Gly Phe His Asp Asp Gly Thr Tyr Ser Leu Ser Gly Glu
tcc tgc att gat atc gat gaa tgt gcc tta aga act cac act tgt tgg    1882
Ser Cys Ile Asp Ile Asp Glu Cys Ala Leu Arg Thr His Thr Cys Trp
aat gat tct gcc tgc atc aac tta gca gga gga ttt gac tgc ctg tgt    1930
Asn Asp Ser Ala Cys Ile Asn Leu Ala Gly Gly Phe Asp Cys Leu Cys
ccc tct ggg ccc tcc tgc tct ggt gac tgt ccc cac gaa gga ggg ctg    1978
Pro Ser Gly Pro Ser Cys Ser Gly Asp Cys Pro His Glu Gly Gly Leu
aag cat aat ggg cag gtg tgg att ctg aga gaa gac agg tgt tca gtc    2026
Lys His Asn Gly Gln Val Trp Ile Leu Arg Glu Asp Arg Cys Ser Val
tgt tcc tgc aag gat ggg aag ata ttc tgc cgg cgg aca gct tgt gat    2074
Cys Ser Cys Lys Asp Gly Lys Ile Phe Cys Arg Arg Thr Ala Cys Asp
tgc cag aat cca aat gtt gac ctt ttt tgc tgc cca gag tgc gat acc    2122
Cys Gln Asn Pro Asn Val Asp Leu Phe Cys Cys Pro Glu Cys Asp Thr
agg gtc acc agc caa tgt tta gat caa agt gga cag aag ctc tat cga    2170
Arg Val Thr Ser Gln Cys Leu Asp Gln Ser Gly Gln Lys Leu Tyr Arg
agt gga gac aac tgg acc cac agc tgc cag cag tgc cga tgt ctg gaa    2218
Ser Gly Asp Asn Trp Thr His Ser Cys Gln Gln Cys Arg Cys Leu Glu
gga gag gca gac tgc tgg cct ctg gct tgc cct agt ttg ggc tgt gaa    2266
Gly Glu Ala Asp Cys Trp Pro Leu Ala Cys Pro Ser Leu Gly Cys Glu
tac aca gcc atg ttt gaa ggg gag tgt tgt ccc cga tgt gtc agt gac    2314
Tyr Thr Ala Met Phe Glu Gly Glu Cys Cys Pro Arg Cys Val Ser Asp
ccc tgc ctg gct ggt aat att gcc tat gac atc aga aaa act tgc ctg    2362
Pro Cys Leu Ala Gly Asn Ile Ala Tyr Asp Ile Arg Lys Thr Cys Leu
gac agc ttt ggt gtt tcg agg ctg agc gga gcc gtg tgg aca atg gct    2410
Asp Ser Phe Gly Val Ser Arg Leu Ser Gly Ala Val Trp Thr Met Ala
gga tct cct tgt aca acc tgc aaa tgc aag aat ggg aga gtc tgc tgc    2458
Gly Ser Pro Cys Thr Thr Cys Lys Cys Lys Asn Gly Arg Val Cys Cys
tct gtg gat ctg gag tgt att gag aat aac tga agattttaaa tggactcgtc  2511
Ser Val Asp Leu Glu Cys Ile Glu Asn Asn  *
acgtgagaaa atgggcaaaa tgatcatccc acctgaggaa gaagaggggc tgatttcttt   2571
ttctttttaa ccacagtcaa ttaccaaagt ctccatctga ggaaggcgtt tggattgcct   2631
ttgccacttt gctcatcctt gctgacctag tctagatgcc tgcagtaccg tgcatttcgg   2691
tcgatggttg ttgagtctca gtgttgtaaa tcgcatttcc ctcgtcagat catttacaga   2751
tacatttaaa ggggttccat gataaatgtt aatgtaactt tgtttattt tgtgtactga    2811
cataatagag acttggcacc attatttat ttttcttgat ttttggatca aattctaaaa   2871
ataaagttgc ctgttgcgaa aaaaaaaaaa aaaaaaaaaa aaaa                   2915
```

*Rattus norvegicus* NELL1 amino acid sequence (SEQ ID NO: 12)

```
Met Pro Met Asp Val Ile Leu Val Leu Trp Phe Cys Val Cys Thr Ala Arg
Thr Val Leu Gly Phe Gly Met Asp Pro Asp Leu Gln Leu Asp Ile Ile Ser
Glu Leu Asp Leu Val Asn Thr Thr Leu Gly Val Thr Gln Val Ala Gly Leu
His Asn Ala Ser Lys Ala Phe Leu Phe Gln Asp Val Gln Arg Glu Ile His
Ser Ala Pro His Val Ser Glu Lys Leu Ile Gln Leu Phe Arg Asn Lys Ser
Glu Phe Thr Phe Leu Ala Thr Val Gln Gln Lys Pro Ser Thr Ser Gly Val
Ile Leu Ser Ile Arg Glu Leu Glu His Ser Tyr Phe Glu Leu Glu Ser Ser
Gly Pro Arg Glu Ile Arg Tyr His Tyr Ile Gly Gly Lys Pro Arg
Thr Glu Ala Leu Pro Tyr Arg Met Ala Asp Gly Gln Trp His Lys Val Ala
Leu Ser Val Ser Ala Ser His Leu Leu Leu His Ile Asp Cys Asn Arg Ile
Tyr Glu Arg Val Ile Asp Pro Pro Glu Thr Asn Leu Pro Pro Gly Ser Asn
Leu Trp Leu Gly Gln Arg Asn Gln Lys His Gly Phe Phe Lys Gly Ile Ile
Gln Asp Gly Lys Ile Ile Phe Met Pro Asn Gly Phe Ile Thr Gln Cys Pro
Asn Leu Asn Arg Thr Cys Pro Thr Cys Ser Asp Phe Leu Ser Leu Val Gln
Gly Ile Met Asp Leu Gln Glu Leu Leu Ala Lys Met Thr Ala Lys Leu Asn
Tyr Ala Glu Thr Arg Leu Gly Gln Leu Glu Asn Cys His Cys Glu Lys Thr
Cys Gln Val Ser Gly Leu Leu Tyr Arg Asp Gln Asp Ser Trp Val Asp Gly
Asp Asn Cys Gly Asn Cys Thr Cys Lys Ser Gly Ala Val Glu Cys Arg Arg
Met Ser Cys Pro Pro Leu Asn Cys Ser Pro Asp Ser Leu Pro Val His Ile
Ser Gly Gln Cys Cys Lys Val Cys Arg Pro Lys Cys Ile Tyr Gly Gly Lys
Val Leu Ala Glu Gly Gln Arg Ile Leu Thr Lys Thr Cys Arg Cys Tyr Arg
Gly Gly Val Leu Val Lys Ile Thr Glu Ala Cys Pro Pro Leu Asn Cys Ser
Ala Lys Asp His Ile Leu Pro Glu Asn Gln Cys Cys Arg Val Cys Pro Gly
His Asn Phe Cys Ala Glu Ala Pro Lys Cys Gly Glu Asn Ser Glu Cys Lys
Asn Trp Asn Thr Lys Ala Thr Cys Glu Cys Lys Asn Gly Tyr Ile Ser Val
Gln Gly Asn Ser Ala Tyr Cys Glu Asp Ile Asp Glu Cys Ala Ala Lys Met
His Tyr Cys His Ala Asn Thr Val Cys Val Asn Leu Pro Gly Leu Tyr Arg
Cys Asp Cys Val Pro Gly Tyr Ile Arg Val Asp Asp Phe Ser Cys Thr Glu
His Asp Asp Cys Gly Ser Gly Gln His Asn Cys Asp Lys Asn Ala Ile Cys
Thr Asn Thr Val Gln Gly His Ser Cys Thr Cys Lys Pro Gly Tyr Val Gly
Asn Gly Thr Ile Cys Lys Ala Phe Cys Glu Glu Gly Cys Arg Tyr Gly Gly
Thr Cys Val Ala Pro Asn Lys Cys Val Cys Pro Ser Gly Phe Thr Gly Ser
His Cys Glu Lys Asp Ile Asp Glu Cys Ala Glu Gly Phe Val Glu Cys His
Asn Tyr Ser Arg Cys Val Asn Leu Pro Gly Trp Tyr Cys Glu Cys Arg
Ser Gly Phe His Asp Asp Gly Thr Tyr Ser Leu Ser Gly Glu Ser Cys Ile
Asp Ile Asp Glu Cys Ala Leu Arg Thr His Thr Cys Trp Asn Asp Ser Ala
```

```
Cys Ile Asn Leu Ala Gly Gly Phe Asp Cys Leu Cys Pro Ser Gly Pro Ser
Cys Ser Gly Asp Cys Pro His Glu Gly Gly Leu Lys His Asn Gly Gln Val
Trp Ile Leu Arg Glu Asp Arg Cys Ser Val Cys Ser Cys Lys Asp Gly Lys
Ile Phe Cys Arg Arg Thr Ala Cys Asp Cys Gln Asn Pro Asn Val Asp Leu
Phe Cys Cys Pro Glu Cys Asp Thr Arg Val Thr Ser Gln Cys Leu Asp Gln
Ser Gly Gln Lys Leu Tyr Arg Ser Gly Asp Asn Trp Thr His Ser Cys Gln
Gln Cys Arg Cys Leu Glu Gly Glu Ala Asp Cys Trp Pro Leu Ala Cys Pro
Ser Leu Gly Cys Glu Tyr Thr Ala Met Phe Glu Gly Glu Cys Cys Pro Arg
Cys Val Ser Asp Pro Cys Leu Ala Gly Asn Ile Ala Tyr Asp Ile Arg Lys
Thr Cys Leu Asp Ser Phe Gly Val Ser Arg Leu Ser Gly Ala Val Trp Thr
Met Ala Gly Ser Pro Cys Thr Thr Cys Lys Cys Lys Asn Gly Arg Val Cys
Cys Ser Val Asp Leu Glu Cys Ile Glu Asn Asn
```

*Felis catus* NELL1 isoform 1 amino acid sequence (SEQ ID NO: 13)
```
Met Pro Arg Asp Val Ile Leu Val Val Trp Phe Cys Val Cys Thr Ala Arg
Thr Val Val Gly Phe Gly Thr Asp Pro Asp Leu Gln Val Asp Ile Ile Ala
Glu Leu Asp Leu Val Asn Thr Thr Ala Gly Val Thr Gln Val Ser Gly Leu
His Asn Ala Ser Lys Ala Tyr Leu Phe Gln Glu Thr Glu Arg Glu Ile His
Ala Ala Pro His Val Ser Glu Lys Leu Ile Gln Leu Phe Arg Asn Lys Ser
Glu Phe Ser Phe Leu Ala Thr Val Gln Gln Lys Pro Ser Thr Ser Gly Val
Ile Leu Ser Ile Arg Glu Leu Glu His Ser Tyr Phe Glu Leu Glu Ser Ser
Gly Leu Arg Asp Glu Ile Arg Tyr His Tyr Ile His Asn Gly Lys Pro Arg
Thr Glu Ala Leu Pro Tyr Arg Met Ala Asp Gly Gln Trp His Lys Val Ala
Leu Ser Ile Ser Ala Ser His Leu Leu Leu His Val Asp Cys Asn Arg Ile
Tyr Glu Arg Val Ile Asp Pro Pro Glu Thr Asn Leu Pro Pro Gly Ser Asn
Val Trp Leu Gly Gln Arg Asn Gln Lys His Gly Leu Phe Lys Gly Ile Ile
Gln Asp Gly Lys Ile Ile Phe Met Pro Asn Gly Tyr Ile Thr Gln Cys Pro
Asn Leu Asn Arg Thr Cys Pro Thr Cys Ser Asp Phe Leu Ser Leu Val Gln
Gly Ile Met Asp Leu Gln Glu Leu Leu Ala Lys Met Thr Ala Lys Leu Asn
Tyr Ala Glu Thr Arg Leu Asn Gln Leu Glu Asn Cys His Cys Glu Lys Thr
Cys Gln Val Ser Gly Leu Leu Tyr Arg Asp Gln Asp Ser Trp Val Asp Gly
Asp His Cys Arg Asn Cys Thr Cys Lys Ser Gly Ala Val Glu Cys Arg Arg
Met Ser Cys Pro Pro Leu Asn Cys Ser Pro Asp Ser Leu Pro Val His Ile
Ala Gly Gln Cys Cys Lys Val Cys Arg Pro Cys Ile Tyr Gly Gly Lys
Val Leu Ala Glu Gly Gln Arg Ile Leu Thr Lys Ser Cys Arg Glu Cys Arg
Gly Gly Val Leu Val Lys Ile Thr Asp Ala Cys Pro Pro Leu Asn Cys Ser
Glu Lys Asp His Ile Leu Pro Glu Asn Gln Cys Cys Ser Val Cys Arg Gly
His Ser Phe Cys Ala Glu Gly Pro Thr Cys Gly Asp Asn Ser Glu Cys Lys
Asn Trp Asn Thr Lys Ala Thr Cys Glu Cys Lys Asn Gly Tyr Ile Ser Val
Gln Gly Asp Ser Ala Tyr Cys Glu Asp Ile Asp Glu Cys Ala Ala Lys Met
His Tyr Cys His Ala Asn Thr Val Cys Val Asn Leu Pro Gly Leu Tyr Arg
Cys Asp Cys Val Pro Gly Tyr Ile Arg Val Asp Asp Phe Ser Cys Thr Glu
His Asp Glu Cys Gly Ser Gly Gln His Asn Cys Asp Ser Asn Ala Ile Cys
Thr Asn Thr Val Gln Gly His Ser Cys Thr Cys Lys Pro Gly Tyr Val Gly
Asn Gly Thr Ile Cys Arg Ala Phe Cys Gln Glu Gly Cys Arg Tyr Gly Gly
Thr Cys Val Ser Pro Asn Lys Cys Val Cys Pro Ser Gly Phe Thr Gly Ser
His Cys Glu Lys Asp Ile Asp Glu Cys Thr Cys Ile Glu Cys His
Asn His Ser Arg Cys Val Asn Leu Pro Gly Trp Tyr His Cys Glu Cys Arg
Ser Gly Phe His Asp Asp Gly Thr Tyr Ser Leu Ser Gly Glu Ser Cys Ile
Asp Ile Asp Glu Cys Ala Leu Arg Thr His Thr Cys Trp Asn Asp Ser Ala
Cys Ile Asn Leu Ala Gly Gly Phe Asp Cys Leu Cys Pro Ser Gly Pro Ser
Cys Ser Gly Asp Cys Pro His Glu Gly Gly Leu Lys Arg Asn Gly Gln Val
Trp Thr Leu Lys Glu Asp Arg Cys Ser Val Cys Ser Cys Lys Asp Gly Lys
Ile Phe Cys Arg Arg Thr Ala Cys Asp Cys Gln Asn Pro Ser Val Asp Leu
Phe Cys Cys Pro Glu Cys Asp Thr Arg Val Thr Ser Gln Cys Leu Asp Gln
Asn Gly His Lys Leu Tyr Arg Ser Gly Asp Asn Trp Thr His Ser Cys Gln
Gln Cys Arg Cys Leu Glu Gly Glu Val Asp Cys Trp Pro Leu Thr Cys Pro
Asn Leu Ser Cys Glu Tyr Thr Ala Met Leu Glu Gly Glu Cys Cys Pro Arg
Cys Val Ser Asp Pro Cys Leu Ala Asp Asn Ile Ala Tyr Asp Ile Arg Lys
Thr Cys Leu Asp Ser Tyr Gly Ile Ser Arg Leu Ser Gly Ala Val Trp Thr
Met Ala Gly Ser Pro Cys Thr Thr Cys Lys Cys Lys Asn Gly Ser Val Cys
Cys Ser Val Asp Leu Glu Cys Leu His Asn Asn
```

*Felis catus* NELL1 isoform 2 amino acid sequence (SEQ ID NO: 14)
```
Met Pro Arg Asp Val Ile Leu Val Val Trp Phe Cys Val Cys Thr Ala Arg
Thr Val Val Gly Phe Gly Thr Asp Pro Asp Leu Gln Val Asp Ile Ile Ala
Glu Leu Asp Leu Val Asn Thr Thr Ala Gly Val Thr Gln Val Ser Gly Leu
His Asn Ala Ser Lys Ala Tyr Leu Phe Gln Glu Thr Glu Arg Glu Ile His
Ala Ala Pro His Val Ser Glu Lys Leu Ile Gln Leu Phe Arg Asn Lys Ser
Glu Phe Ser Phe Leu Ala Thr Val Gln Gln Lys Pro Ser Thr Ser Gly Val
Iel Leu Ser Ile Arg Glu Leu Glu His Ser Tyr Phe Glu Leu Glu Ser Ser
Gly Leu Arg Asp Glu Ile Arg Tyr His Tyr Ile His Asn Gly Lys Pro Arg
Thr Glu Ala Leu Pro Tyr Arg Met Ala Asp Gly Gln Trp His Lys Val Ala
Leu Ser Ile Ser Ala Ser His Leu Leu Leu His Val Asp Cys Asn Arg Ile
Tyr Glu Arg Val Ile Asp Pro Pro Glu Thr Asn Leu Pro Pro Gly Ser Asn
Val Trp Leu Gly Gln Arg Asn Gln Lys His Gly Leu Phe Lys Gly Ile Ile
Gln Asp Gly Lys Ile Ile Phe Met Pro Asn Gly Tyr Ile Thr Gln Cys Pro
Asn Leu Asn Arg Thr Cys Pro Thr Cys Ser Asp Phe Leu Ser Leu Val Gln
Gly Ile Met Asp Leu Gln Glu Leu Leu Ala Lys Met Thr Ala Lys Leu Asn
```

```
Tyr Ala Glu Thr Arg Leu Asn Gln Leu Glu Asn Cys His Cys Glu Lys Thr
Cys Gln Val Ser Gly Leu Leu Tyr Arg Asp Gln Asp Ser Trp Val Asp Gly
Asp His Cys Arg Asn Cys Thr Cys Lys Ser Gly Ala Val Glu Cys Arg Arg
Met Ser Cys Pro Pro Leu Asn Cys Ser Pro Asp Ser Leu Pro Val His Ile
Ala Gly Gln Cys Cys Lys Val Cys Arg Pro Lys Cys Ile Tyr Gly Gly Lys
Val Leu Ala Glu Gly Gln Arg Ile Leu Thr Lys Ser Cys Arg Glu Cys Arg
Gly Gly Val Leu Val Lys Ile Thr Asp Ala Cys Pro Pro Leu Asn Cys Ser
Glu Lys Asp His Ile Leu Pro Glu Asn Gln Cys Cys Ser Val Cys Arg Gly
His Asn Phe Cys Ala Glu Gly Pro Thr Cys Gly Glu Asn Ser Glu Cys Lys
Asn Trp Asn Thr Lys Ala Thr Cys Glu Cys Lys Asn Gly Tyr Ile Ser Val
Gln Gly Asp Ser Ala Tyr Cys Glu Asp Ile Asp Glu Cys Ala Ala Lys Met
His Tyr Cys His Ala Asn Thr Val Cys Val Asn Leu Pro Gly Leu Tyr Arg
Cys Asp Cys Val Pro Gly Tyr Ile Arg Val Asp Phe Ser Cys Thr Glu
His Asp Glu Cys Gly Ser Gly Gln His Asn Cys Asp Glu Asn Ala Ile Cys
Thr Asn Thr Val Gln Gly His Ser Cys Thr Cys Lys Pro Gly Tyr Val Gly
Asn Gly Thr Ile Cys Arg Ala Phe Cys Gln Glu Gly Cys Arg Tyr Gly Gly
Thr Cys Val Ser Pro Asn Lys Cys Val Cys Pro Ser Gly Phe Thr Gly Ser
His Cys Glu Lys Asp Ile Asp Glu Cys Ala Leu Thr His Thr Cys Trp
Asn Asp Ser Ala Cys Ile Asn Leu Ala Gly Gly Phe Asp Cys Leu Cys Pro
Ser Gly Pro Ser Cys Ser Gly Asp Cys Pro His Glu Gly Gly Leu Lys Arg
Asn Gly Gln Val Trp Thr Leu Lys Glu Asp Arg Cys Ser Val Cys Ser Cys
Lys Asp Gly Lys Ile Phe Cys Arg Arg Thr Ala Cys Asp Cys Gln Asn Pro
Ser Val Asp Leu Phe Cys Cys Pro Glu Cys Asp Thr Arg Val Thr Ser Gln
Cys Leu Asp Gln Asn Gly His Lys Leu Tyr Arg Ser Gly Asp Asn Trp Thr
His Ser Cys Gln Gln Cys Arg Cys Leu Glu Gly Glu Val Asp Cys Trp Pro
Leu Thr Cys Pro Asn Leu Ser Cys Glu Tyr Thr Ala Met Leu Glu Gly Glu
Cys Cys Pro Arg Cys Val Ser Asp Pro Cys Leu Ala Asp Asn Ile Ala Tyr
Asp Ile Arg Lys Thr Cys Leu Asp Ser Tyr Gly Ile Ser Arg Leu Ser Gly
Ala Val Trp Thr Met Ala Gly Ser Pro Cys Thr Thr Cys Lys Cys Lys Asn
Gly Ser Val Cys Cys Ser Val Asp Leu Glu Cys Leu His Asn Asn

Canis lupis familiaris NELL1 amino acid sequence (SEQ ID NO: 15)
Met Thr Ser Thr Ser Phe Leu Leu Trp Leu Gly Cys Val His Asn Thr Lys
Phe Pro Phe Pro Leu Val Leu Val Thr Arg Ala Ile Val Val Val Val Val
Glu Val Val Gly Val Gly Ser Pro Gly Val Arg Ile Arg Ser Thr Gly Cys
Asp Ile Leu Leu Leu Tyr Glu Val Leu Glu His Leu Leu Gly Ile Arg Phe
Leu Cys Val Asp Gln Gly Glu Asn Ser Cys His His Gly Gln Cys Ala Cys
Arg Leu Gln Val Ile Val Pro Lys Ala Leu Met Ser Val Phe Glu Ala Lys
Thr Ala Val Cys Phe Phe Pro Val Val Gly Phe Gly Thr Asp Pro Asp Leu
Gln Met Asp Ile Ile Thr Glu Leu Asp Leu Val Asn Ile Ser Leu Gly Val
Thr Gln Val Ser Gly Leu His Asn Ala Ser Lys Ala Tyr Val Phe Gln Asp
Thr Ala Arg Glu Ile His Ala Ala Pro His Val Ser Glu Lys Leu Ile Gln
Leu Phe Arg Asn Lys Ser Asp Phe Thr Phe Leu Ala Thr Val Gln Gln Lys
Pro Ser Thr Ser Gly Val Ile Leu Ser Ile Arg Glu Leu Glu His Ser Tyr
Phe Glu Leu Glu Ser Ser Gly Leu Arg Asp Glu Ile Arg Tyr His Tyr Met
His Asn Gly Lys Pro Arg Thr Glu Ala Leu Pro Tyr Arg Leu Ala Asp Gly
Gln Trp His Lys Val Ala Leu Ser Val Ser Ala Ser His Leu Leu Leu His
Ile Asp Cys Asn Arg Ile Tyr Glu Arg Val Ile Asp Pro Pro Glu Thr Asn
Leu Pro Pro Gly Ser Asn Leu Trp Leu Gly Gln Arg Asn Gln Lys His Gly
Phe Phe Lys Gly Ile Ile Gln Asp Gly Lys Ile Ile Phe Met Pro Asn Gly
Tyr Ile Thr Gln Cys Pro Asn Leu Asn Arg Thr Cys Pro Thr Cys Ser Asp
Phe Leu Ser Leu Val Gln Gly Ile Met Asp Leu Gln Glu Leu Leu Ala Lys
Met Thr Ala Lys Leu Asn Tyr Ala Glu Thr Arg Leu Ser Gln Leu Glu Asn
Cys His Cys Glu Lys Thr Cys Gln Val Ser Gly Leu Leu Tyr Arg Asp Gln
Asp Ser Trp Val Asp Gly Asp His Cys Arg Asn Cys Thr Cys Lys Ser Gly
Ala Val Glu Cys Arg Arg Met Ser Cys Pro Pro Leu Asn Cys Ser Pro Asp
Ser Leu Pro Val His Ile Ala Gly Gln Cys Cys Lys Val Cys Arg Pro Lys
Cys Ile Tyr Gly Gly Arg Val Leu Ala Glu Gly Gln Arg Ile Leu Thr Lys
Ser Cys Arg Glu Cys Arg Gly Gly Val Leu Val Ile Thr Asp Ala Cys
Pro Pro Leu Asn Cys Ser Glu Lys Asp His Ile Leu Pro Glu Asn Gln Cys
Cys Ser Val Cys Arg Gly His Asn Phe Cys Ala Glu Gly Pro Lys Cys Gly
Glu Asn Ser Glu Cys Lys Asn Trp Asn Thr Lys Ala Thr Cys Glu Cys Lys
Asn Gly Tyr Ile Ser Val Gln Gly Asp Ser Ala Tyr Cys Glu Asp Ile Asp
Glu Cys Ala Ala Lys Met His Tyr Cys His Ala Ala Asn Thr Val Cys Val Asn
Leu Pro Gly Leu Tyr Arg Cys Asp Cys Val Pro Gly Tyr Ile Arg Val Asp
Asp Phe Ser Cys Thr Glu His Asp Glu Cys Gly Ser Gly Gln His Asn Cys
Asp Glu Asn Ala Ile Cys Thr Asn Thr Val Arg Gly His Ser Cys Thr Cys
Lys Pro Gly Tyr Val Gly Asn Gly Thr Ile Cys Arg Ala Phe Cys Gln Glu
Gly Cys Arg Tyr Gly Gly Ser Cys Val Ser Pro Asn Lys Cys Val Cys Pro
Ser Gly Phe Thr Gly Ser His Cys Glu Lys Asp Ile Asp Glu Cys Thr Glu
Gly Ile Ile Glu Cys His Asn His Ser Arg Cys Val Asn Leu Pro Gly Trp
Tyr His Cys Glu Cys Arg Ser Gly Phe His Asp Asp Gly Thr Tyr Ser Leu
Ser Gly Glu Ser Cys Ile Asp Ile Asp Glu Cys Ala Leu Arg Thr His Thr
Cys Trp Asn Asp Ser Ala Cys Ile Asn Leu Ala Gly Gly Phe Asp Cys Leu
Cys Pro Ser Gly Pro Ser Cys Ser Gly Asp Cys Pro His Glu Gly Gly Leu
Lys Arg Asn Gly Gln Val Trp Thr Leu Lys Glu Asp Arg Cys Ser Val Cys
Ser Cys Lys Asp Gly Lys Ile Leu Cys Arg Arg Thr Ala Cys Asp Cys Gln
Asn Pro Ser Val Asp Leu Phe Cys Cys Pro Glu Cys Asp Thr Arg Val Thr
Ser Gln Cys Leu Asp Gln Asn Gly His Lys Leu Tyr Arg Ser Gly Asp Asn
```

-continued

```
Trp Thr His Ser Cys Gln Gln Cys Arg Cys Leu Glu Gly Glu Val Asp Cys
Trp Pro Leu Thr Cys Pro Asn Leu Ser Cys Glu Tyr Thr Ala Ile Leu Glu
Gly Glu Cys Cys Pro Arg Cys Val Ser Asp Pro Cys Leu Ala Asp Asn Ile
Ala Tyr Asp Ile Arg Lys Thr Cys Leu Asp Ser Tyr Gly Ile Ser Arg Leu
Ser Gly Ser Val Trp Thr Met Ala Gly Ser Pro Cys Thr Thr Cys Lys Cys
Lys Asn Gly Ser Val Cys Cys Ser Val Asp Leu Glu Cys Leu His Asn Asn
```

*Ovis aries* NELL1 amino acid sequence (SEQ ID NO: 16)
```
Met Pro Arg Gly Val Ile Leu Val Val Cys Phe Cys Val Cys Ala Ala Arg
Thr Val Val Gly Phe Gly Met Asp Pro Asp Leu Gln Leu Asp Ile Ile Thr
Glu Leu Asp Leu Val Asn Thr Thr Leu Gly Val Thr Gln Val Ser Gly Leu
His Asn Thr Ser Lys Ala Phe Leu Phe Gln Asp Ala Glu Arg Glu Ile His
Ala Ala Pro His Val Ser Glu Lys Leu Ile Gln Leu Phe Arg Asn Lys Ser
Glu Phe Thr Phe Leu Ala Thr Val Gln Gln Lys Pro Ser Thr Ser Gly Val
Ile Leu Ser Ile Arg Glu Leu Glu His Ser Tyr Phe Glu Leu Glu Ser Ser
Gly Leu Arg Asp Glu Ile Arg Tyr His Tyr Met His Ser Gly Arg Pro Arg
Thr Glu Ala Leu Pro Tyr Arg Leu Ala Asp Gly Gln Trp His Arg Val Ala
Leu Ser Val Ser Ala Ser His Leu Leu Leu His Ile Asp Cys Asn Arg Ile
Tyr Glu Arg Val Ile Asp Pro Pro Glu Thr Asn Leu Pro Pro Gly Ser Asn
Leu Trp Leu Gly Gln Arg Asn Gln Lys His Gly Leu Phe Lys Gly Ile Ile
Gln Asp Gly Lys Ile Ile Phe Met Pro Asn Gly Tyr Ile Thr Gln Cys Pro
Asn Leu Asn Arg Thr Cys Pro Thr Cys Ser Asp Phe Leu Ser Leu Val Gln
Gly Ile Met Asp Leu Gln Glu Leu Leu Ala Lys Met Thr Ala Lys Leu Asn
Tyr Ala Glu Thr Arg Leu Ser Gln Leu Glu Asn Cys His Cys Glu Lys Thr
Cys Gln Val Ser Gly Leu Leu Tyr Arg Asp Gln Asp Ser Trp Val Asp Gly
Asp His Cys Arg Asn Cys Thr Cys Lys Ser Gly Ala Val Glu Cys Arg Arg
Met Ser Cys Pro Pro Leu Asn Cys Ser Pro Asp Ser Leu Pro Val His Ile
Ala Gly Gln Cys Cys Lys Val Cys Arg Pro Lys Cys Ile Tyr Gly Gly Lys
Val Leu Ala Glu Gly Gln Arg Ile Leu Ser Lys Asn Cys Gln Glu Cys Arg
Gly Val Leu Val Lys Ile Thr Glu Ala Cys Pro Leu Leu Asn Cys Ser
Glu Lys Asp His Ile Leu Pro Glu Asn Gln Cys Cys Ser Val Cys Arg Gly
His Asn Phe Cys Ala Glu Gly Pro Lys Cys Gly Glu Asn Ser Glu Cys Lys
Asn Trp Asn Thr Lys Ala Thr Cys Glu Cys Lys Asn Gly Tyr Ile Ser Val
Gln Gly Asp Ser Ala Tyr Cys Glu Asp Ile Asp Cys Ala Ala Lys Met
His Tyr Cys His Ala Asn Thr Val Cys Val Asn Leu Pro Gly Leu Tyr Arg
Cys Asp Cys Val Pro Gly Tyr Ile Arg Val Asp Asp Phe Ser Cys Thr Glu
His Asp Asp Cys Gly Ser Gly Gln His Asn Cys Asp Glu Asn Ala Ile Cys
Thr Asn Thr Val Gln Gly His Ser Cys Thr Cys Lys Pro Gly Tyr Val Gly
Asn Gly Thr Ile Cys Arg Ala Phe Cys Glu Glu Gly Cys Arg Tyr Gly Gly
Thr Cys Met Ala Pro Asn Lys Cys Val Cys Pro Ser Gly Phe Thr Gly Ser
His Cys Glu Lys Asp Ile Asp Glu Cys Ala Gly Ile Ile Glu Cys His
Ser His Ser Arg Cys Val Asn Leu Pro Gly Trp Tyr His Cys Glu Cys Arg
Ser Gly Phe His Asp Asp Gly Thr Tyr Ser Leu Glu Gly Ser Cys Val
Asp Ile Asp Glu Cys Ala Leu Arg Thr His Thr Cys Trp Asn Asp Ser Ala
Cys Ile Asn Leu Ala Gly Gly Phe Asp Cys Leu Cys Pro Ser Gly Pro Ser
Cys Ser Gly Asp Cys Pro His Glu Gly Gly Leu Lys Arg Asn Gly Gln Val
Trp Thr Leu Lys Glu Asp Arg Cys Ser Val Cys Ser Cys Lys Asp Gly Lys
Ile Phe Cys Arg Arg Thr Ala Cys Asp Cys Gln Asn Pro Ser Val Asp Leu
Phe Cys Cys Pro Glu Cys Asp Thr Arg Val Thr Ser Gln Cys Leu Asp Gln
Asn Gly Asn Lys Leu Tyr Arg Ser Gly Asp Asn Trp Thr His Ser Cys Gln
Gln Cys Arg Cys Leu Glu Gly Glu Val Asp Cys Trp Pro Leu Thr Cys Pro
Ser Leu Ser Cys Glu Tyr Thr Thr Ile Leu Glu Gly Glu Cys Cys Pro Arg
Cys Val Ser Asp Pro Cys Leu Ala Asp Asn Ile Ala Tyr Asp Ile Arg Lys
Thr Cys Leu Asp Ser Tyr Gly Leu Ser Arg Leu Ser Gly Ser Val Trp Thr
Met Ala Gly Ser Pro Cys Thr Thr Cys Lys Cys Lys Asn Gly Ser Val Cys
Cys Ser Val Asp Leu Glu Cys Leu His Asn Asn
```

*Homo sapiens* NELL1 fragment amino acid sequence (SEQ ID NO: 17)
```
Phe Gly Met Asp Pro Asp Leu Gln Met Asp Ile Val Thr Glu Leu Asp Leu
Val Asn Thr Thr Leu Gly Val Ala Gln Val Ser Gly Met His Asn Ala Ser
Lys Ala Phe Leu Phe Gln Asp Ile Glu Arg Glu Ile His Ala Ala Pro His
Val Ser Glu Lys Leu Ile Gln Leu Phe Arg Asn Lys Ser Glu Phe Thr Ile
Leu Ala Thr Val Gln Gln Lys Pro Ser Thr Ser Gly Val Ile Leu Ser Ile
Arg Glu Leu Glu His Ser Tyr Phe Glu Leu Glu Ser Ser Gly Leu Arg Asp
Glu Ile Arg Tyr His Tyr Ile His Asn Gly Lys Pro Arg Thr Glu Ala Leu
Pro Tyr Arg Met Ala Asp Gly Gln Trp His Lys Val Ala Leu Ser Val Ser
Ala Ser His Leu Leu Leu His Val Asp Cys Asn Arg Ile Tyr Glu Arg Val
Ile Asp Pro Pro Asp Thr Asn Leu Pro Pro Gly Ile Ala Asn Leu Trp Leu Gly
Gln Arg Asn Gln Lys His Gly Leu Phe Lys Gly Ile Ile Gln Asp Gly Lys
Ile Ile Phe Met Pro Asn Gly Tyr Ile Thr Gln Cys Pro Asn Leu Asn His
Thr Cys Pro Thr Cys Ser Asp Phe Leu Ser Leu Val Gln Gly Ile Met Asp
Leu Gln Glu Leu Leu Ala Lys Met Thr Ala Lys Leu Asn Tyr Ala Glu Thr
Arg Leu Ser Gln Leu Glu Asn Cys His Cys Glu Lys Thr Cys Gln Val Ser
Gly Leu Leu Tyr Arg Asp Gln Asp Ser Trp Val Asp Gly Asp His Cys Arg
Asn Cys Thr Cys Lys Ser Gly Ala Val Glu Cys Arg Arg Met Ser Cys Pro
Pro Leu Asn Cys Ser Pro Asp Ser Leu Pro Val His Ile Ala Gly Gln Cys
Cys Lys Val Cys Arg Pro Lys Cys Ile Tyr Gly Gly Lys Val Leu Ala Glu
Gly Gln Arg Ile Leu Thr Lys Ser Cys Arg Glu Cys Arg Gly Gly Val Leu
Val Lys Ile Thr Glu Met Cys Pro Pro Leu Asn Cys Ser Glu Lys Asp His
```

-continued

Ile Leu Pro Glu Asn Gln Cys Cys Arg Val Cys Arg Gly His Asn Phe Cys
Ala Glu Gly Pro Lys Cys Gly Glu Asn Ser Glu Cys Lys Asn Trp Asn Thr
Lys Ala Thr Cys Glu Cys Lys Ser Gly Tyr Ile Ser Val Gln Gly Asp Ser
Ala Tyr Cys Glu Asp Ile Asp Glu Cys Ala Ala Lys Met His Tyr Cys His
Ala Asn Thr Val Cys Val Asn Leu Pro Gly Leu Tyr Arg Cys Asp Cys Val
Pro Gly Tyr Ile Arg Val Asp Asp Phe Ser Cys Thr Glu His Asp Glu Cys
Gly Ser Gly Gln His Asn Cys Asp Glu Asn Ala Ile Cys Thr Asn Thr Val
Gln Gly His Ser Cys Thr Cys Lys Pro Gly Tyr Val Gly Asn Gly Thr Ile
Cys Arg Ala Phe Cys Glu Glu Gly Cys Arg Tyr Gly Gly Thr Cys Val Ala
Pro Asn Lys Cys Val Cys Pro Ser Gly Phe Thr Gly Ser His Cys Glu Lys
Asp Ile Asp Glu Cys Ser Glu Gly Ile Ile Glu Cys His Asn His Ser Arg
Cys Val Asn Leu Pro Gly Trp Tyr His Cys Glu Cys Arg Ser Gly Phe His
Asp Asp Gly Thr Tyr Ser Leu Ser Gly Glu Ser Cys Ile Asp Ile Asp Glu
Cys Ala Leu Arg Thr His Thr Cys Trp Asn Asp Ser Ala Cys Ile Asn Leu
Ala Gly Gly Phe Asp Cys Leu Cys Pro Ser Gly Pro Ser Cys Ser

*Equus caballus* NELL1 fragment amino acid sequence (SEQ ID NO: 18)
Phe Gly Met Asp Pro Asp Leu Gln Met Asp Ile Ile Thr Glu Leu Asp Leu
Val Asn Thr Thr Leu Gly Val Thr Gln Val Ser Gly Leu His Asn Ala Ser
Lys Ala Phe Leu Phe Gln Asp Val Glu Arg Glu Ile His Ala Ala Pro His
Val Ser Glu Lys Leu Ile Gln Leu Phe Arg Asn Lys Ser Glu Phe Thr Phe
Leu Ala Thr Val Gln Gln Lys Pro Ser Thr Ser Gly Val Ile Leu Ser Ile
Arg Glu Leu Glu Asn Ser Tyr Phe Glu Leu Glu Ser Ser Gly Leu Arg Asp
Glu Ile Arg Tyr His Tyr Thr His Lys Gly Lys Pro Arg Thr Glu Ala Leu
Pro Tyr Arg Met Ala Asp Gly Arg Trp His Lys Val Ala Leu Ser Val Ser
Ala Ser His Leu Leu Leu His Ile Asp Cys Asn Arg Ile Tyr Glu Arg Val
Ile Asp Thr Pro Glu Thr Asn Leu Pro Pro Gly Ser Asn Leu Trp Leu Gly
Gln Arg Asn Gln Lys His Gly Leu Phe Lys Gly Ile Ile Gln Asp Gly Lys
Ile Ile Phe Met Pro Asn Gly Tyr Ile Thr Gln Cys Pro Asn Leu Asn Arg
Thr Cys Pro Thr Cys Ser Asp Phe Leu Ser Leu Val Gln Gly Ile Met Asp
Leu Gln Glu Leu Leu Ala Lys Met Thr Ala Lys Leu Asn Tyr Ala Glu Thr
Arg Leu Ser Gln Leu Glu Asn Cys His Cys Glu Lys Thr Cys Gln Val Ser
Gly Leu Leu Tyr Arg Asp Gln Asp Ser Trp Val Asp Gly Asp His Cys Arg
Asn Cys Thr Cys Lys Ser Gly Ala Val Glu Cys Arg Arg Met Ser Cys Pro
Pro Leu Asn Cys Ser Pro Asp Ser Leu Pro Val His Val Ala Gly Gln Cys
Cys Lys Val Cys Arg Pro Lys Cys Ile Tyr Gly Gly Lys Val Leu Ala Glu
Gly Gln Arg Ile Leu Thr Lys Ser Cys Arg Glu Cys Arg Gly Gly Val Leu
Val Lys Ile Thr Glu Ala Cys Pro Pro Leu Asn Cys Ser Asp Lys Asp His
Ile Leu Pro Glu Asn Gln Cys Cys Ser Val Cys Arg Gly His Asn Phe Cys
Ala Glu Gly Pro Lys Cys Gly Glu Asn Ser Glu Cys Lys Asn Trp Asn Thr
Lys Ala Thr Cys Glu Cys Lys Asn Gly Tyr Ile Ser Val Gln Gly Asp Ser
Ala Tyr Cys Glu Asp Ile Asp Glu Cys Ala Ala Lys Met His Tyr Cys Arg
Ala Asn Thr Val Cys Val Asn Leu Pro Gly Leu Tyr Arg Cys Asp Cys Val
Pro Gly Tyr Ile Arg Val Asp Asp Phe Ser Cys Thr Glu His Asp Glu Cys
Gly Ser Gly Gln His Asn Cys Asp Glu Asn Ala Ile Cys Thr Asn Thr Val
Gln Gly His Ser Cys Thr Cys Lys Pro Gly Tyr Val Gly Asn Gly Thr Ser
Cys Arg Ala Phe Cys Glu Glu Gly Cys Arg Tyr Gly Gly Thr Cys Val Ala
Pro Asn Lys Cys Val Cys Pro Ser Gly Phe Thr Gly Ser His Cys Glu Lys
Asp Ile Asp Glu Cys Thr Glu Gly Ile Ile Glu Cys His Asn His Ser Arg
Cys Val Asn Leu Pro Gly Trp Tyr His Cys Glu Cys Arg Ser Gly Phe His
Asp Asp Gly Thr Tyr Ser Leu Ser Gly Glu Ser Cys Ile Asp Ile Asp Glu
Cys Ala Leu Arg Thr His Thr Cys Trp Asn Asp Ser Ala Cys Ile Asn Leu
Ala Gly Gly Phe Asp Cys Leu Cys Pro Ser Gly Pro Ser Cys Ser

*Bos taurus* NELL1 amino acid sequence (SEQ ID NO: 19)
Met Ala Leu Cys Ser Phe Ser Val Val Gly Phe Gly Leu Asp Pro Asp Leu
Gln Leu Asp Ile Ile Thr Glu Leu Asp Leu Val Asn Thr Thr Leu Gly Val
Thr Gln Val Ser Gly Leu His Asn Thr Ser Lys Ala Phe Leu Phe Gln Asp
Ala Glu Arg Glu Ile His Ala Ala Pro His Val Ser Glu Lys Leu Ile Gln
Leu Phe Arg Asn Lys Ser Glu Phe Thr Phe Leu Ala Thr Val Gln Gln Lys
Pro Ser Thr Ser Gly Val Ile Leu Ser Ile Arg Glu Leu Glu His Ser Tyr
Phe Glu Leu Glu Ser Ser Gly Leu Arg Asp Glu Ile Arg Tyr His Tyr Val
His Ser Gly Arg Pro Arg Thr Glu Ala Leu Pro Tyr Arg Leu Ala Asp Gly
Gln Trp His Arg Val Ala Leu Ser Val Ser Ala Ser His Leu Leu Leu His
Ile Asp Cys Asn Arg Ile Tyr Glu Arg Val Ile Asp Pro Pro Glu Thr Asn
Leu Pro Pro Gly Ser Asn Leu Trp Leu Gly Gln Arg Asn Gln Lys His Gly
Leu Phe Lys Gly Ile Ile Gln Asp Gly Lys Ile Ile Phe Met Pro Asn Gly
Tyr Ile Thr Gln Cys Pro Asn Leu Asn Arg Thr Cys Pro Thr Cys Ser Asp
Phe Leu Ser Leu Val Gln Gly Ile Met Asp Leu Gln Glu Leu Leu Ala Lys
Met Thr Ala Lys Leu Asn Tyr Ala Glu Thr Arg Leu Ser Gln Leu Glu Asn
Cys His Cys Glu Lys Thr Cys Gln Val Ser Gly Leu Leu Tyr Arg Asp Gln
Asp Ser Trp Val Asp Gly Asp His Cys Arg Asn Cys Thr Cys Lys Ser Gly -continued

```
Ala Val Glu Cys Arg Arg Met Ser Cys Pro Pro Leu Asn Cys Ser Pro Asp
Ser Leu Pro Val His Ile Ala Gly Glu Cys Cys Lys Val Cys Arg Pro Lys
Cys Ile Tyr Gly Gly Lys Val Leu Ala Glu Gly Gln Arg Ile Leu Ser Lys
Ser Cys Gln Glu Cys Arg Gly Gly Val Leu Val Lys Ile Thr Glu Ala Cys
Pro Leu Asn Cys Ser Glu Lys Asp His Ile Leu Pro Glu Asn Gln Cys
Cys Ser Val Cys Arg Gly His Asn Phe Cys Ala Glu Gly Pro Lys Cys Gly
Glu Asn Ser Glu Cys Lys Asn Trp Asn Thr Lys Ala Thr Cys Glu Cys Lys
Asn Gly Tyr Ile Ser Val Gln Gly Asp Ser Ala Tyr Cys Glu Asp Ile Asp
Glu Cys Ala Ala Lys Met His Tyr Cys His Ala Asn Thr Val Cys Val Asn
Leu Pro Gly Leu Tyr Arg Cys Asp Cys Val Pro Gly Tyr Ile Arg Val Asp
Asp Phe Ser Cys Thr Glu His Asp Asp Cys Gly Ser Gly Gln His Asn Cys
Asp Glu Asn Ala Ile Cys Thr Asn Thr Val Gln Gly His Ser Cys Thr Cys
Lys Pro Gly Tyr Val Gly Asn Gly Thr Ile Cys Arg Gly Met Pro Glu Val
Gly Pro Pro Arg Ala Leu Leu Asn Ser Leu Asp Leu Gly Phe Leu Ser Phe
Ser Lys Glu Ala Leu Ala Val Gly Met Ile Thr Leu Glu Gly Asn Ile Val
Ala Lys Ser Phe Thr Asp Asp Glu Thr Leu Val Glu Arg Gly Arg Glu Lys
Val Ile Ala Leu Leu Phe Ser Trp Leu His Lys Glu Lys Leu Ser Leu Glu
Asn Leu Arg Asp Ile Tyr Cys Lys Ala Asn Ser Leu Val Gly Leu Asp His
Leu Pro Gln Arg
```

EXAMPLES

The present invention, thus generally described, will be understood more readily by reference to the following Examples, which are provided by way of illustration and are not intended to be limiting of the instant invention. The Examples are not intended to represent that the experiments below are all experiments performed.

Example 1

Cloning and Expression of Recombinant Horse NELL1 Peptides

Various Nell1 polypeptides were designed based on the horse (*Equus caballus*) reference sequence: XP_001505306.1 GI: 149719523 (Aug. 14, 2013). The horse protein sequence has recently been updated in the NCBI database as XP_014597419 (Nov. 20, 2015).

The "full-length" version coding sequence begins at amino acid (aa) #3 which is the start of the signaling sequence till the last amino acid (#791) and contains all predicted conserved protein domains. Three variant NELL1 proteins were designed such that certain specific N-or C-terminal domain(s) was/were missing and the alternative form was shorter in size than the full-length version (Table 2). These four different recombinant NELL1 proteins were manufactured using a high-throughput wheat germ cell-free translation system (commercial Cell-Free System (CFS) In Vitro Wheat Germ System developed by Abnova Corporation, Taipei, Taiwan). The gene sequence was cloned in a plasmid vector that was transcribed and then translated in vitro in a wheat germ extract containing all 20 different amino acids. This protein expression system was pioneered by Yaeta Endo and later developed into a high throughput format (Madin et al. (2000) *Proc. Natl. Acad. Sci. U.S.A.* 97(2):559-564; Sawasaki et al. (2000) *Nucleic Acids Symp Ser* 44:9-10; Sawasaki et al. (2002) *Proc. Natl. Acad. Sci. U.S.A.* 99(23):14652-14657; and Endo and Sawasaki (2003) *Biotechnol. Adv.* 21(8):695-713). Purification of the products was accomplished by binding of the NELL1 protein tagged with glutathione S-transferase (GST) to an anti-GST resin. The products were eluted in 50 mM Tris-HCl, 10 mM reduced glutathione, pH 8.0.

TABLE 2

Description of recombinant horse NELL1 peptides.

| NELL1 Protein Description | Deleted Domains | MW (kDa)* | Concentration (µg/µl) | Purity (%) |
|---|---|---|---|---|
| NELL1 aa 3-791 (full-length) | None | 112.42 | 0.09 | 87.22 |
| NELL1 aa 252-791 | Entire N-terminal thrombospondin domain | 85.03 | 0.05 | 56.27 |
| NELL1 aa 3-612 | Two C-terminal von Willebrand factor C (VWC) domains | 92.73 | 0.13 | 89.44 |
| NELL1 aa 34-612 | Initial part of N-terminal thrombospondin domain and 2 C-terminal VWC domains | 89.32 | 0.17 | 65.82 |

*includes GST-tag of 26 kDa

To determine purity, 0.5 microgram protein was loaded in a lane on a 12.5% SDS-PAGE gel and stained with Coomassie Blue. BioSpectrum AC® Imaging System with software-Vision WorksLS V6.8 was employed to determine the purities by calculating the ratio of the major expected band for each protein variant relative to other minor bands. The value of concentration is the index of yield. The higher the concentration, the more yield is obtained. If a polypeptide has <0.1 µg/µl, the protein is considered difficult to produce and purify.

The full-length horse NELL1 protein (aa 3-791) has both lower concentration/yield and purity (0.09 µg/µl; 87.22%), compared to the NELL1 variant with 3-612 amino acid sequence (0.13 µg/µl; 89.44%). The other NELL1 variants (MW=85.03 kDa and MW=89.32) have very low concentration/yield and/or purity and were not deemed optimal for testing further for biological activity in vivo.

Additional independent preparations of variant and full-length NELL1 proteins were produced and utilized to check biological activity using in vitro (e.g. elution of protein from two scaffolds and wound healing scratch assays) and in vivo experiments (e.g. horse body wound healing study). Several preparations of amounts ranging from 20 micrograms-2.5 milligrams consistently yielded levels of concentration and purities similar to those obtained in the first experiment→90% for the NELL1 variant #3-612 and 85-87% for the full-length (FIGS. 2A-2D).

Example 2

Effects of NELL1 Peptide on an In Vitro Model of Tendon Injury and Repair

There are several in vitro systems that can be utilized to demonstrate the efficacy of NELL1 in tendon repair and regeneration. These strategies make use of precursor or stem cells that give rise to tendons and can show that addition of NELL1 protein stimulates proliferation, differentiation, gene expression of key genes in tendon formation and/or migration of these cells.

The effects of NELL1 in the in vitro model of tendon injury and repair as described in Nemoto et al. (2013) *J Equine Sci* 24(2): 17-24 are determined as follows. Fibroblasts are obtained from tendon explants dissected and minced into pieces from the superficial digital flexor tendon of healthy adult horses at the time of slaughter. Treatment with 0.1% type I collagenase (37 degrees, 20 minutes) will degrade the collagen holding cells in the tendon ECM, thereby releasing cells. Cells are cultured on Dulbecco's Modified Eagle Medium [with 10% fetal bovine serum, 100U/ml penicillin G, 100 microgram/ml streptomycin] at 5% $CO_2$, 37° C. to sub-confluence. Cell cultures are dispersed with 0.1% trypsin in PBS and sub-cultured close to confluence (~4 days in 12-well plates), then used for the classic scratch assay. Five parallel 0.1 mm "scratches" are made (1000 microliter blue pipette tip) in each cell culture plate, simulating a "wound gap" or injury in the cell sheet.

NELL1 protein, at varying doses, is added to three cultures per dose (15 gaps or wounds per dose measured). Three cultures are designated as negative controls. Initial doses for testing based on other in vitro studies with NELL1 are (ng/ml): 10, 31.6, 100, 316, 1000, and 3160.

The gaps are examined and measured every other day until they are closed. Data is analyzed to determined rates of closure and which treatment(s) exhibited the best and fastest healing.

The experiment described above is repeated and instead of quantitative measurements of gap closure, samples are cultured and harvested at various time points (after 0, 12, 24, 28 and 78 hrs post NELL1 treatment) for RNA extraction, cDNA synthesis and gene expression analysis. Genes that are biomarkers for tendon proliferation and migration are assessed. Examples of such genes are: Collagen 1, Collagen III, Tenascin C, and COMP.

Example 3

NELL1 Peptide Promotes Cell Migration and Wound Healing in Human Fibroblasts In Vitro The effects of two NELL1 proteins (full-length and variant 3-612aa) on cell migration and wound healing were tested and compared using in vitro models of primary human fibroblasts: adult dermal fibroblasts, type 1 diabetes dermal fibroblasts, and ligament fibroblasts. Three doses of both NELL1 proteins (full-length and variant 3-612aa) were tested on wound healings assays for each cell type using 4-6 replicates per dose: 100 ng/ml, 200 ng/ml, 300 ng/ml. Human fibroblasts were cultured in typical fibroblast growth media (FGM) supplemented with fetal bovine serum (FBS) and various growth factors. Cells in the logarithmic growing phase were cultured overnight in 96-well plates to make cell monolayers. Wound areas (750-micron wide) were generated in the middle of the cell monolayers in a consistent manner using an IncuCyte WoundMaker® 96 (Essen Bioscience, Michigan, U.S.A.). After treatment, cells were incubated and observed in an IncuCyte® Live-Cell Analysis System (Essen Bioscience, Michigan, U.S.A.). Images of cell migration and wound closure were captured using phase contrast microscopy each hour over a 24-hour period. Wound areas, cell confluence and healing rates (average velocity of cells moving into gap) were measured and data was analyzed using GraphPad Prism 7.0.

Figure 3A:
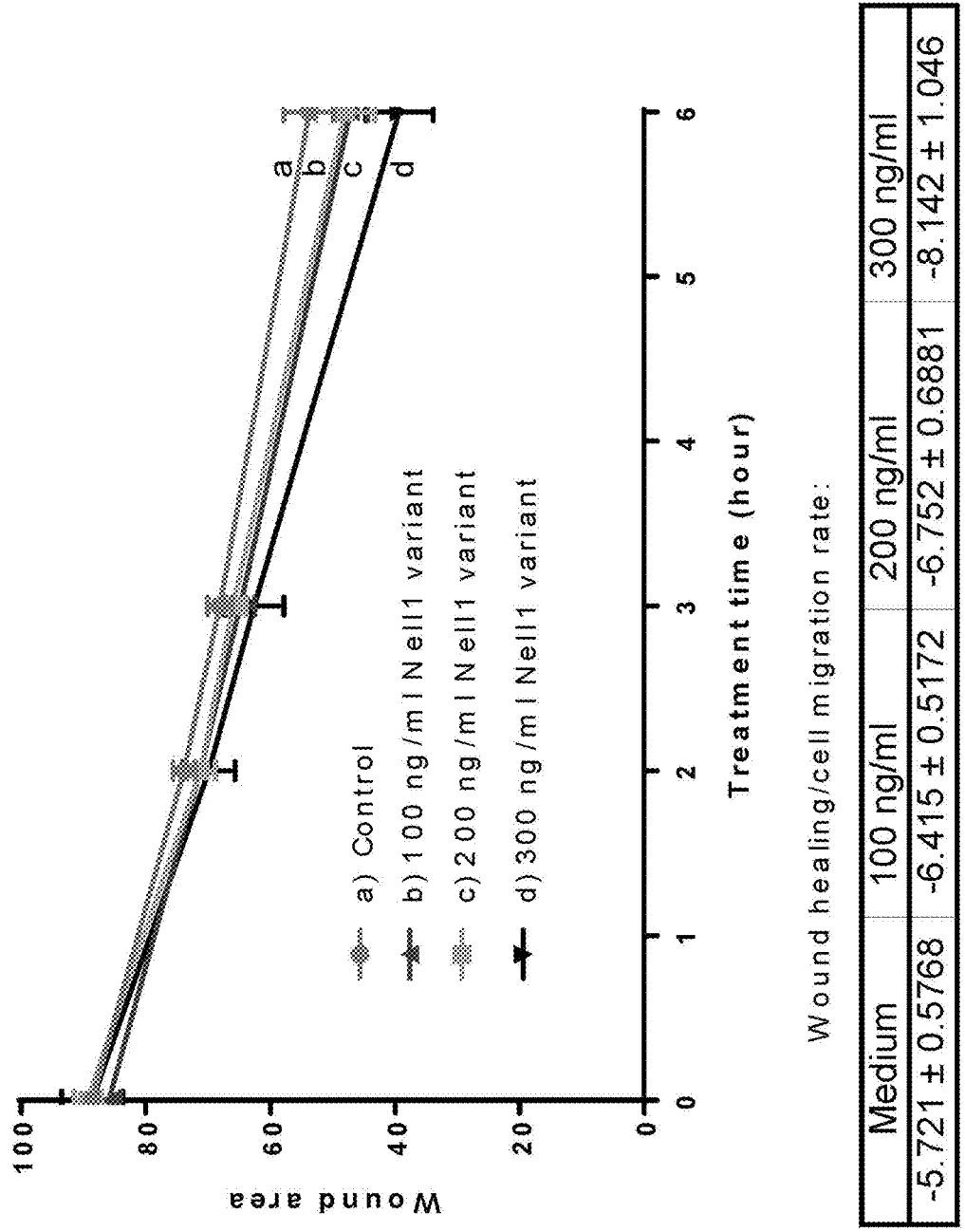
FIGS. 3A-3D depict effects of full-length NELL1 protein (aa3-791) or a NELL1 protein variant (aa3-612) on wound healing assays using diabetic dermal fibroblasts (FIGS. 3A and 3B), normal dermal fibroblasts (FIG. 3C), and normal ligament fibroblasts (FIG. 3D).
Figure 3B:
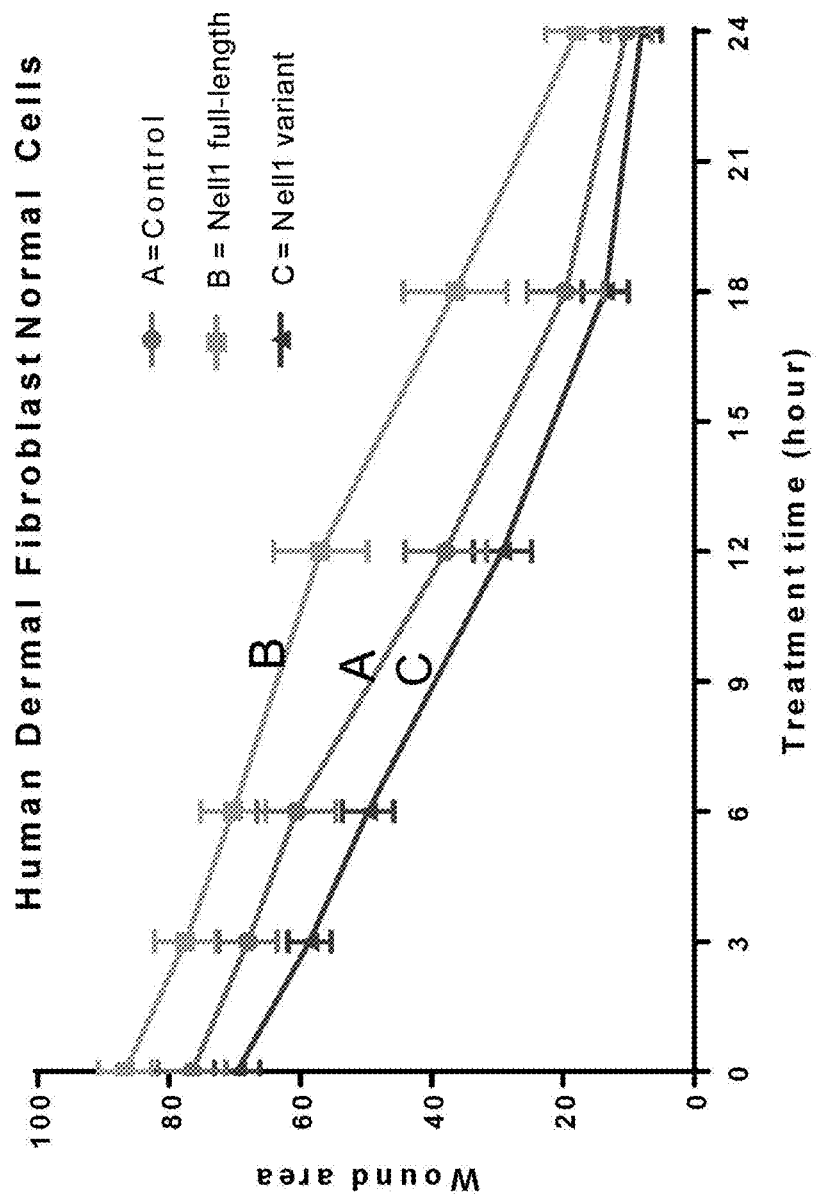
Figure 3C:
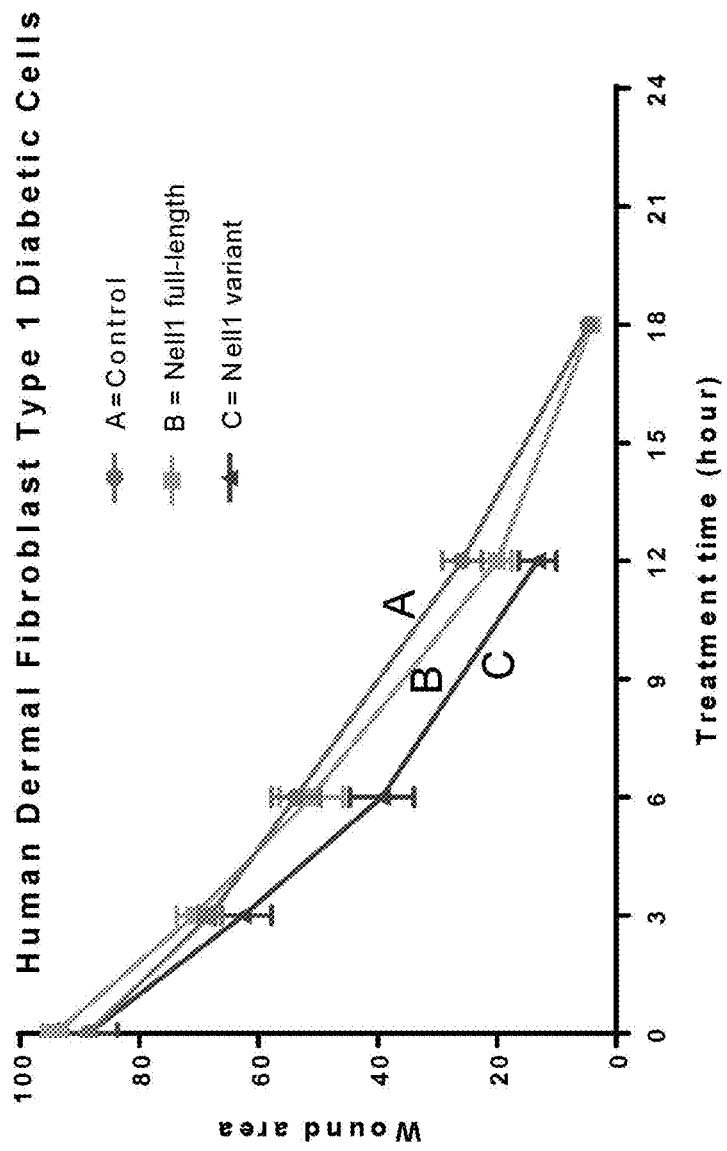
Figure 3D:
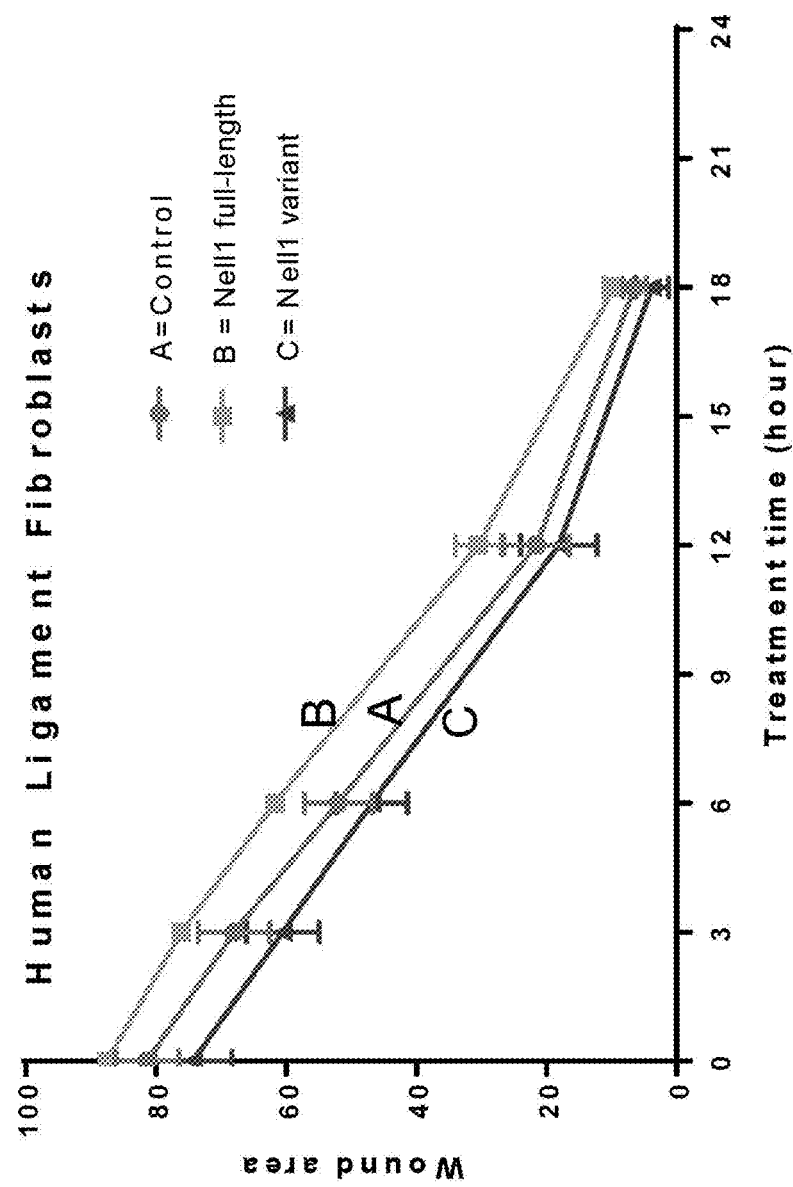

Not only did the NELL1 variant protein increase the rate of normal human dermal fibroblast cell migration, but also the migration of type 1 diabetes dermal fibroblast cells and in a dose dependent manner compared to the full-length NELL1 protein and control untreated cells, with the highest dose tested showing the highest increase in wound closure (FIGS. 3A-3C). The mean migration rates were: 5.7, 6.4, 6.8, and 8.1 for medium control, 100, 200, and 300 ng/ml of NELL1 variant, respectively. Treatment with the NELL1 variant at the highest dose tested (300 ng/ml) also showed increased wound healing in ligament-derived fibroblasts compared to untreated controls (FIG. 3D).

Although full-length NELL1 protein did not promote closure of the wound areas in these initial studies, an alternative dosage of full-length NELL1 protein or alternative culture conditions, for example, growth of the fibroblasts in serum-free medium, might be necessary in order to exhibit such an effect.

Methods

Cells. The following primary cells were purchased: normal human dermal fibroblasts (ixcells Biotech, Cat. #10HU-014), type 1 diabetes human dermal fibroblasts (ixcells Biotech, Cat. #10HU-014), and normal human ligament fibroblasts (ScienCell Research Lab, Inc., Cat. #2630).

Primary cultures of these human fibroblasts were established in complete Fibroblast Growth Medium (FGM; ScienCell Research Laboratories; Cat. #2301) and incubated in a humidified 37° C., 5% $CO_2$ incubator. The FGM was supplemented with 10% heat-inactivated fetal bovine serum (FBS), penicillin (100 units/ml), streptomycin (100 µg/ml), and other growth factors, according to the protocol of the cell suppliers.

Human fibroblast monolayer scratch (wound healing) assay. 96-well plates were coated with a thin layer of biomatrix according to cell types. The cell numbers were optimized/titrated per well in the plate for each type of cells. Cells were seeded in the log growing phase into each well (maximum of 100 µL per well) on 96-well microplates and cells were incubated overnight in a humidified 37° C., $CO_2$ incubator to form 100% confluent cell monolayers.

An IncuCyte® WoundMaker device/platform was used to create homogeneous, 750-micron wide scratch wounds in the middle of the cell monolayers on 96-well microplates, by strictly following the IncuCyte® WoundMaker protocol. The medium with cell debris was removed immediately after wounding/scratching by gentle aspiration on the side of each well. Each well was carefully replenished with 100 µL per well of fresh pre-warmed medium and any cell debris removed by gentle aspiration on the side of each well. Each well (free of debris) was replenished with 50 µL per well of fresh pre-warmed medium, or 50 µL per well of fresh medium with NELL1 protein (full-length or NELL1 3-612aa variant) with the appropriate concentration to achieve the required dose in each well. Four dosages were tested in at least 4 replicates per treatment: untreated Control (0), 100 ng/ml, 200 ng/ml and 300 ng/ml for each of the NELL1 full-length protein and the NELL1 variant protein. Plates were gently tapped to mix.

The plate with cells was incubated in an IncuCyte® Live-Cell Analysis System. Phase contrast images of cell migration towards the empty space in the wounded area were captured/recorded (10× magnification, digitally zoomed) at time of 0 (start), and then every other hour post wounding and treatments. The time courses of migration of cells in an IncuCyte® Live-Cell Analysis System were recorded. The total pixel of cells in the wounded area before and after treatments was measured using the IncuCyte™ Software. The following calculations were made from the data:

Wound area at timepoints (Tn) = the area between wound boundaries over time

Cell confluence area = Wound area (T0) − Wound area (Tn)

Relative cell confluence in the wound =

Cell confluence in the wound/total wound area * 100

Wound healing rate = the average velocity at which the cells collectively move into the wound gap; is the absoute value of the slope of curve fitting of cell confluence areas over the times (dA/dt) before 50% cell confluency.

Data were analyzed and plotted out using GraphPad Prism 7.0 (San Diego, CA).

Example 4

Effects of NELL1 Peptide on an In Vivo Model of Equine Tendon/Ligament Injury

Tendon injury animal models are well established in horses because of the great demand for treatments of tendon damage, especially in valuable racehorses and show/dressage horses (Schramme et al. (2010) *Vet Comp Orthop Traumatol* 358-365; Estrada et al. (2014) *Vet Comp Orthop Traumatol* 358-365; Nixon et al. (2008) *Am J Vet Res* 69:928-937; Watts et al. (2012) *EVJ* 44(5):576-586). The most common model of damage to the Superficial Digital Flexor Tendon (SDFT) is a good model for the human Achilles tendon, a significant and common injury in human patients. Equine SDFT tendonitis can be created chemically using collagenase or via surgical means.

The following study is performed on a surgically induced SDFT tendonitis equine model.

Twenty-four healthy adult horses are selected and randomly assigned into four groups with six horses per group. The dosing of NELL1 is extrapolated from wound healing studies in horses based on the amount of protein per area of injury. Group 1 is administered saline solution as a control. Group 2 is administered dose 1 (400 micrograms of NELL1). Group 3 is administered dose 2 (800 micrograms of NELL1) and Group 4 is administered dose 3 (1600 micrograms of NELL1).

After general anesthesia, a core lesion of 8 cm in the SDFT of a randomized forelimb is generated with a 3.5 mm synovial resector under ultrasound imaging. Operated limbs are bandaged for two weeks post-operation until sutures are removed. Horses are confined to a stall during this two week period.

NELL1 treatment is administered under sedation via intralesional injection guided by ultrasound imaging, once at seven days post-injury.

Rehabilitation is performed on a treadmill after two weeks with the length of time walking steadily increasing (10 mins/day during weeks 3-6, 20 mins/day during weeks 7-10, 30 mins/day during weeks 11-14, 40 mins/day during weeks 15-20). During weeks 21-22, rehabilitation will be 35 mins/day walking and 5 mins/day trotting. Rehab during weeks 23-24 will consist of 30 mins/day walking and 10 mins/day trotting.

Healing is assessed by a variety of techniques: a) regular ultrasound evaluation at 2-weeks, 4-weeks, 6-weeks, 8-weeks, 12-weeks, 16-weeks, 20-weeks and 24-weeks; b) histological examination of tendons at the end of study; and c) gene expression via quantitative RTPCR techniques of tendon-specific genes (collagen types I, III, decorin, cartilage oligomeric protein (COMP) and Tenascin C.

Example 5

NELL1 Peptide Promotes Healing of Body Wounds in Horse

In order to test the efficacy of the NELL1 protein in healing soft tissue injuries in a large animal model with economic/commercial veterinary significance, purified, recombinant, horse NELL1, full-length protein (NFL) and a variant domain-specific form (NV1) were administered to body wounds of horses. NFL spans amino acids 3-791 of the horse NELL1 protein and contains all the known/predicted domains of the horse NELL1 protein, while NVI contains amino acids 3-612 and does not contain the last two von willebrand factor domains at the C-terminus of the protein.

Six circular 4-cm diameter wounds (3/side) were created surgically on the thorax of 8 adult female horses to evaluate wound healing. Two days after wounding, during the first dressing change, wounds were treated with one of the following: control—volume equal to that of sterile saline that was used to dilute the stock NELL1 protein; dose 1 (95.2 μg/4-cm wound) of NFL or NV1; or dose 2 (190.4 μg/4-cm wound) of NFL or NV1. NELL1 was delivered by directly infusing a biodegradable, commercially available calcium alginate dressing. Wound healing was assessed over a period of 42 days using a 3-D imaging system (Eykona camera; Bowling et al. (2008) The Eykona Wound Measurement System: Modernizing Wound Measurement for the 21$^{st}$ Century. 12$^{th}$ *Malvern Diabetic Foot Conference*, UK8, May 14-16; and Bowling et al. (2009) *Diabetic Medicine* 26(1):93-96). Researchers administering the treatment and performing the regular wound healing measurements were blinded to the treatment and dosage given to a wound.

Statistical analyses indicated significant healing effects for the variant NELL1 protein that enhanced healing based on the remaining inner unhealed wound area at the end of the study (Day 42 post-treatment). In contrast, there were no statistically significant differences observed between untreated control wounds and those treated with the full-length NELL1 protein (NFL). Interestingly, from days 3-14 post-treatment, wounds treated with NFL had consistently lower unhealed areas compared to controls, but these effects were not increased or sustained until the end of the study.

Six general health parameters were monitored daily throughout the study to evaluate safety: body temperature, pulse rate, respiratory rates, defecation, appetite and behavior/attitude (irritability, aggressiveness or unusual behavior). Results indicated that both NFL and NV1 NELL1 proteins did not elicit adverse effects in the test subjects and therefore, is a safe product to use for wound healing in horses.

This initial equine study suggested that healing effects might be boosted with a second application of the NELL1 protein within the second week. There were strong trends of increased wound healing observed from days 3-14 with both NELL1 proteins, but these trends were not sustained for the full-length NELL1. Future wide range dose optimization studies might provide a statistically significant effect with full-length NELL1 and also enhance the observed effects of the variant NELL1 protein.

Methods

Horses. Eight mixed-breed, female adult horses, 8 to 15 years old, weighing 453-589 kgs, free of any clinically detectable medical disorder, were housed in individual stalls and were kept under constant conditions (i.e., temperature, feeding, cleaning) throughout the study. They were examined daily for signs of discomfort, lameness, and illness. Horses were randomly assigned numbers (referred to as treatment identification numbers) 1 through 8, and based on their number, received pre-determined grid pattern of wounds, outlined in FIG. 4, and treatments, listed in Table 3.

Figure 4:
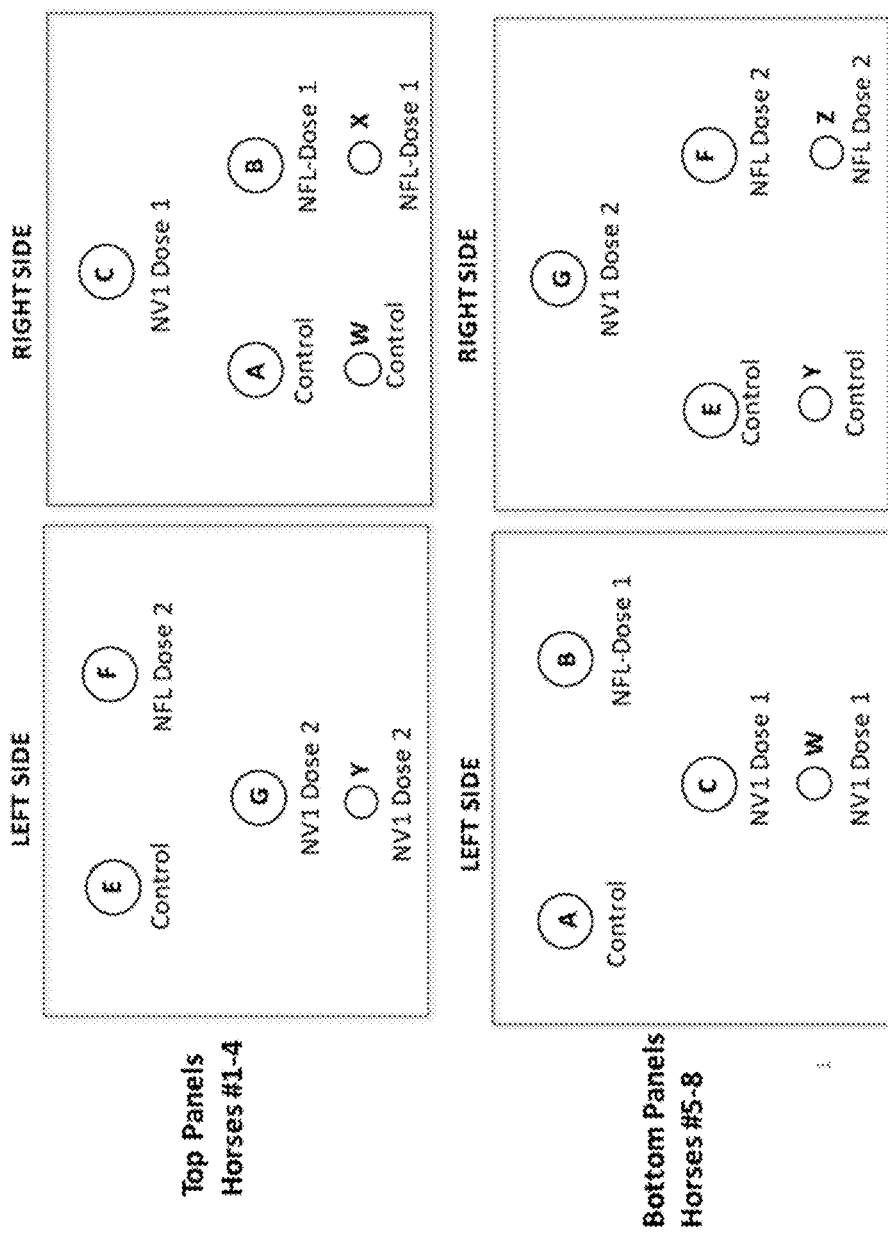
FIG. 4 provides an illustration of the wound grid on each side of the horses indicating the three 4-cm diameter (A, B, C or E, F, G) and the 2-cm diameter cutaneous wounds (W, Y, W and X, or Y and Z) and treatments with control, full-length NELL1 (NFL), or NELL1 variant (NV1). Top grids were for horses 1-4 and the bottom grids were for horses 5-8.
Figure 5:
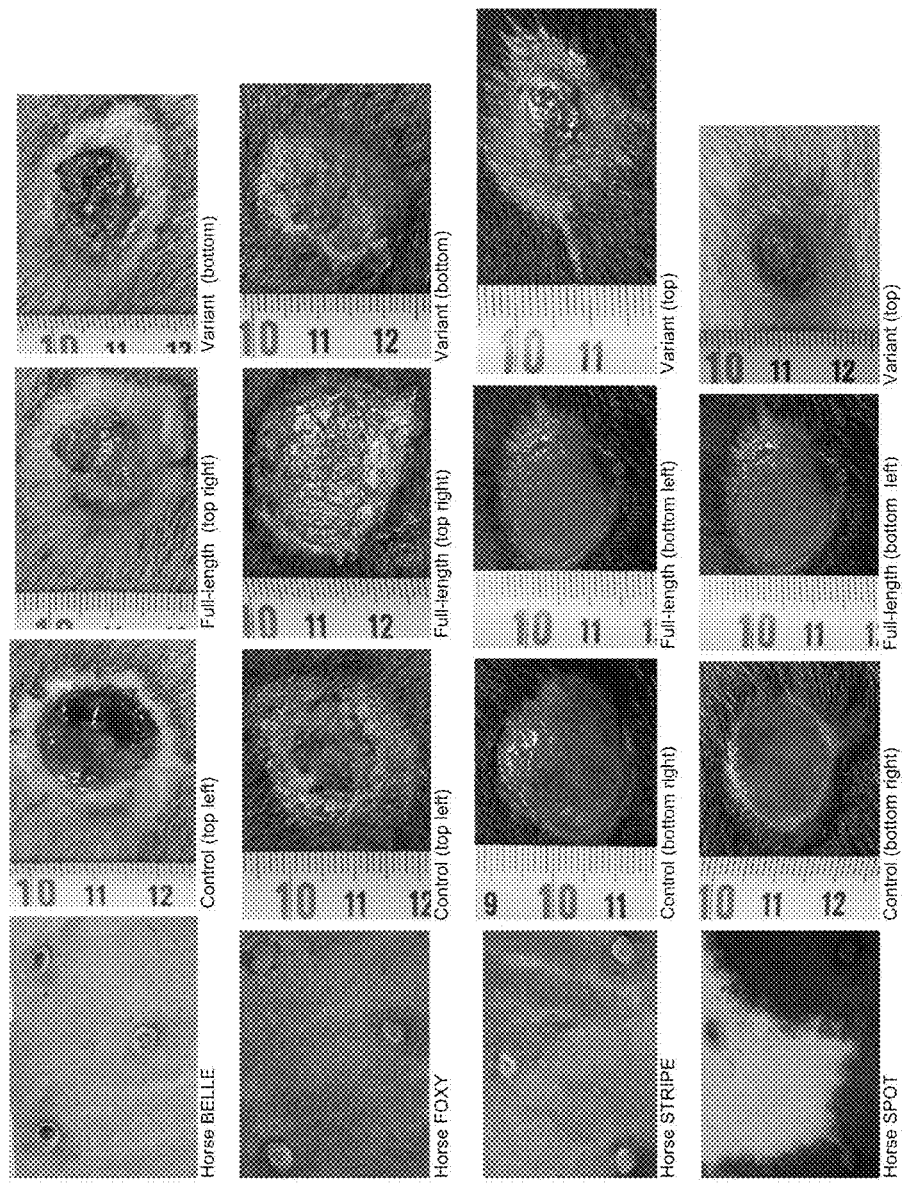
FIG. 5 shows horse body wounds at day 42 post-treatment showing improved healing with NELL1 variant (NV1) compared to full-length NELL1 (NFL) and controls.

Wounding Protocol and Treatment Groups. All procedures were carried out according to approved IACUC protocol (UTK-IACUC No. 2247-0314). The wound model used was a modification of an established equine model (Schumacher et al. (1992) *Am J Vet Res* 53(9):1568-1571; Gomez et al. (2004) *The Canadian Journal of Veterinary Research* 68:49-55; and Morgan et al. (2009) *J Am Vet Med Assoc* 234(9): 1-8). On day 0, each horse was sedated with detomidine HCl (0.006-0.012 mg/kg) and butorphanol (0.006-0.012 mg/kg). Hair on the right and left sides of the thorax was removed with clippers, and the sides of the thorax were prepared for aseptic surgery. Sites of wounds were desensitized with a local anesthetic (2% mepivacaine HCl) subcutaneously. Three, 4-cm diameter and one or two, 2-cm diameter, circular, full-thickness, cutaneous defects were created on the dorsal aspect of the right and left sides of the thorax (FIG. 4). The 4-cm diameter wounds were created at least 8 cm apart from each other, and 2-cm diameter biopsy wounds were created at least 4 cm ventral to the most ventral 4-cm diameter wound(s). All wounds were created using sterilized, 4-cm and 2-cm diameter, stainless steel, custom-made, biopsy punches. 4-cm diameter wounds were allowed to heal over 42 days and were assessed qualitatively and by quantitative measurements (FIG. 5). The large wounds were arranged in a triangular pattern, as illustrated in FIG. 4, designed to prevent solutions applied to the dorsally located wounds from migrating by gravity to the ventral wounds. The smaller wounds generated for biopsy were located directly ventral to the ventral large wounds and were treated identically to the large wounds. Biopsy tissues were collected for future molecular analyses.

Wounds were covered with a sterile, alginate dressing cut to the size of the wound. The dressings were held in place with a sterile, non-adhesive dressing (Telfa Pad, Johnson & Johnson, New Brunswick, NJ), which was stapled to the skin beneath it. Each side of the thorax was covered with a large, sterile combine to compress the wound and to absorb exudate, if any, from the wound. The dressings and the combines were held in place with a custom-made, belly bandage (Boa Abdominal Bandage; Wire 2 Wire Vet Products, LLC, Lexington, KY) positioned over the right and left sides over the thorax, directly over the wounds. Horses received phenylbutazone (2.2 mg/kg, IV) before surgery and for 1 day after surgery (2.2 mg/kg, orally, q12h).

On day 2 after wounding, the alginate dressings were carefully removed. NELL1 protein of the appropriate dose (FIG. 4, Table 3) or sterile isotonic saline solution (control) was loaded into the alginate dressing cut to the size of the wound. The NELL1-soaked dressing or the isotonic saline solution-soaked dressing was laid directly on the wound and covered with a fresh, sterile, non-absorbent non-adhesive dressing, which was stapled to the skin beneath it. The dressings were removed 2 days later, and thereafter, the wounds were dressed twice weekly with a sterile combine pad applied to each side of the thorax and held in place with the belly bandage. FIG. 4 illustrates the position and designations of the wounds, and Table 3 indicates the treatment applied to each wound.

TABLE 3

NELL1 form and dosage for treatment of horse wounds.

| Horse # | 4-cm diameter wound | 2-cm diameter wound for biopsy | Treatment | Dose |
|---|---|---|---|---|
| 1-4 | A-right side | | Control | NA |
| | B-right side | | NELL1, full-length (NFL) | 1 = 95.2 μg |
| | C-right side | | NELL1, Variant 1 (NV1) | 1 = 95.2 μg |
| | | W-right side | Control | NA |
| | | X-right side | NFL | 1 = 23.7 μg |
| | E-left side | | Control | NA |
| | F-left side | | NFL | 2 = 190.4 μg |
| | G-left side | | NV1 | 2 = 190.4 μg |
| | | Y-left side | NV1 | 2 = 47.4 μg |
| 5-8 | A-left side | | control | |
| | B-left side | | NFL | 1 = 95.2 μg |
| | C-left side | | NV1 | 1 = 95.2 μg |
| | | W-left side | NV1 | 1 = 23.7 μg |
| | E-right side | | Control | NA |
| | F-right side | | NFL | 2 = 190.4 μg |
| | G-right side | | NV1 | 2 = 190.4 μg |
| | | Y-right side | Control | NA |
| | | Z-right side | NFL | 2 = 47.4 μg |

Following the treatment groups shown in Table 3, the total samples per group were:

Control=16 big (4-cm) wounds
NFL Dose 1=8 big wounds
NV1 Dose 1=8 big wounds
NFL Dose 2=8 big wounds
NV1 Dose 2=8 big wounds Horse NELL1 protein and variants. Purified recombinant horse NELL1 proteins were manufactured as described in Example 1. The efficacy of two forms of NELL1 protein in treating equine wounds was tested. These two forms were the full-length protein (aa3-791), designated as NFL, and one shorter domain-specific variant (aa3-612), designated as NV1. The NELL1 proteins were stored in buffered solution and shipped frozen in dry ice from Abnova Corp. for storage at −80° C. until ready for use. These proteins were used within 4 weeks of delivery.

Dosage and Delivery. Wounds were treated with a control (isotonic saline solution), NELL1 full-length protein, or the NELL1 variant protein two days after wounding, during the first dressing change. Control treatment was phosphate buffered saline (PBS). Dose 1 (i.e., NELL1 full-length protein) was 95.2 micrograms per 4-cm diameter circular wound, and Dose 2 (i.e., NELL1 variant protein) was 190.4 micrograms per 4-cm diameter wound.

NELL1 proteins were thawed on ice, proper concentrations were prepared, and the buffered NELL1 proteins were loaded/pipetted directly into the selected dressing. The NELL1 protein was loaded in a volume of 2400 μL for application to each of all of the 4-cm diameter wounds, and in a volume of 600 μL for application to each of the 2-cm diameter wounds. These volumes were determined by loading the dressings cut to the sizes of the wounds and by testing various volumes of phosphate-buffered isotonic saline solution to determine maximum loading volume without the solution dripping from the dressing. A 100-mm diameter sterile plastic Petri dish was used for each dressing, and all protein-soaked dressings were prepared under sterile conditions in a tissue culture hood. Each Petri dish was labelled with the horse treatment identification number and the type and dose of the protein applied.

Evaluation of Wound Healing 3-D Imaging. Wound measurements were taken from images obtained from a digital, 3-D wound imaging device that enables rapid, secure, repeatable collection of wound data (TOMI 3D, Eykona Medical, USA). Images were acquired at the following time points: time of wounding, initial treatment, each dressing change (i.e., twice weekly), and at the termination of study.

Data Analyses. All images were downloaded onto a computer with image analysis software developed by Eykona. The images were then analyzed individually using a trace-area function in the software. The outer most margin of the wound was measured first and the area recorded in $mm^2$. These values were recorded over the various time points to determine the rate of wound contraction. The inner area, or non-epithelialized area, was then measured in similar fashion by tracing the area outlined by the epithelial margin. These values were recorded over time and used to calculate the rate of epithelialization.

Because there was some degree of variation in the initial size of the wounds, all measurements were normalized on a percent scale so that the initial wound measurement reflected 100% of the size of the wound. Changes in the overall area of the wound and of the epithelialized area were then subsequently expressed as a percentage. Rates of contraction and epithelialization were expressed as $mm^2$/day.

Rate of contraction was calculated by subtracting the area of the wound at one time-point from the determined area of the wound at the previous time-point and then dividing the difference in area by the number of days between those two time-points. An overall rate of contraction was calculated by subtracting the final area of the wound from the initial area of the wound and dividing the difference by the total number of days between those two time-points. The area of epithelialization for each 4-cm diameter wound was calculated by subtracting the area of the wound from the area of granulation tissue, and the rate of epithelialization was then calculated in similar fashion by subtracting the area of epithelialization at one time-point from the area of epithelialization at the previous time-point and then dividing the difference in area by the number of days between those two time-points.

Results and Discussion

Overall Health Effects of NELL1 Protein. All horses were monitored daily throughout the study period. No adverse effects on the health and behavior of the horses were observed. The temperature, pulse and respiratory rates, defecation, appetite, and attitude of the horses were monitored daily and were within normal limits throughout the 42-day study.

Delivery of NELL1 protein via calcium alginate dressing. This study is the first in which NELL1 protein was administered into soft tissue injuries in horses using a calcium alginate dressing. The selection of this dressing was based upon a previous in vitro study comparing the release of NELL1 protein from a collagen and a calcium alginate commercial dressing. The elution profiles suggested that in a calcium alginate carrier, the NELL1 protein is released within 2-3 days. In this in vivo study, at day 3 post-treatment there was no visual evidence of the dressing and no abnormal acute inflammatory reactions were observed.

Effects of NELL1 on Wound Healing (Days 3-42, rates of wound healing, epithelialization and contraction). For all data analyses, at a given time point, the total area of the wound, the inner area (i.e. the area filled with granulation tissue) and the epithelialized area (i.e., the difference between the total area and the inner area) were calculated for each 4-cm diameter wound of each horse from images obtained at the time of each bandage change. Each measurement was represented as a change in $mm^2$ relative to the previous measurement.

Data was also normalized to account for variation in wound sizes at day 0 and considers that all wounds are at 100% value (all unhealed areas) before treatment.

Figure 6:
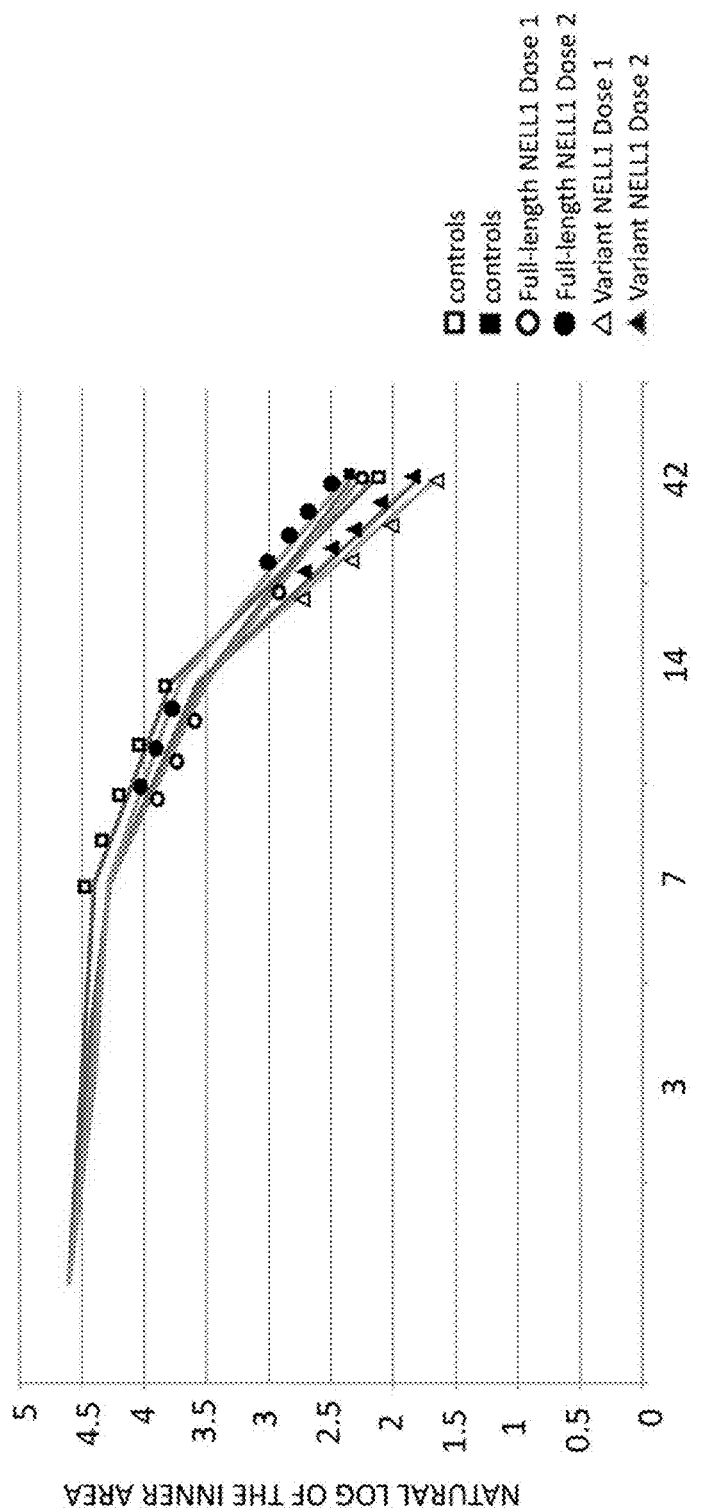
FIG. 6 shows a graph of the natural log values of the inner area in horse wounds that remain unhealed on days post-treatment with full-length (lines 3 and 4) or variant NELL1 protein (lines 5 and 6) and untreated control wounds (lines 1 and 2).

For statistical analyses, cumulative data from each treatment group were analyzed. Initially, standard T-TEST using Microsoft Excel (Windows 7) was used to compare these changes, and the p values were calculated. At day 42 (last day of observation/end of experimental part), analyses of normalized data of inner area (unhealed) indicated strong trends in the wounds treated with the variant NELL1 form (p=0.08 for both Dose 1 and Dose 2; p=0.04 for all wounds treated with the variant regardless of dose). Data shows that horse wounds at Day 42 treated with NELL1 variant showed faster healing (smaller unhealed inner area) compared to control. The wounds have smaller areas that remain unhealed and the variation/standard deviation was consistently lower in wounds treated with the smaller NELL1 variant compared to controls and those treated with the full-length form (FIGS. 5 and 6 and Table 4).

TABLE 4

Healing of 4-cm horse body wounds based on the remaining unhealed inner area at various days post-treatment with a degradable calcium alginate dressing infused with saline solution (untreated controls), full-length (amino acids #3-791) or variant (amino acids #3-612) horse NELL1 protein.

| | OBSERVATIONS (N) | MEAN ($mm^2$) | STANDARD DEVIATION |
|---|---|---|---|
| CONTROL (UNTREATED) | | | |
| Day 3 (T3) | 16 | 90.1 | 5.9 |
| Day 7 (T7) | 16 | 76.7 | 10.5 |
| Day 14 (T14) | 16 | 39.2 | 9.5 |
| Day 42 (T42) | 16 | 9.8 | 5.4 |
| FULL-LENGTH NELL1: DOSE 1 | | | |
| T3 | 8 | 85.8 | 4.9 |
| T7 | 8 | 71.1 | 9.7 |
| T14 | 8 | 32.1 | 6.2 |
| T42 | 8 | 10.3 | 7.9 |
| FULL-LENGTH NELL1: DOSE 2 | | | |
| T3 | 8 | 81.7 | 7.5 |
| T7 | 8 | 72.3 | 10.9 |
| T14 | 8 | 41.0 | 6.5 |
| T42 | 8 | 11.0 | 9.9 |

TABLE 4-continued

Healing of 4-cm horse body wounds based on the remaining unhealed inner area at various days post-treatment with a degradable calcium alginate dressing infused with saline solution (untreated controls), full-length (amino acids #3-791) or variant (amino acids #3-612) horse NELL1 protein.

| | OBSERVATIONS (N) | MEAN (mm²) | STANDARD DEVIATION |
|---|---|---|---|
| VARIANT NELL1 (aa #3-612): DOSE 1 | | | |
| T3 | 8 | 85.3 | 8.6 |
| T7 | 8 | 72.3 | 8.4 |
| T14 | 8 | 31.2 | 14.6 |
| T42 | 8 | 5.5 | 3.9 |
| VARIANT NELL1 (aa #3-612): DOSE 2 | | | |
| T3 | 8 | 86.8 | 5.7 |
| T7 | 8 | 72.2 | 4.3 |
| T14 | 8 | 35.5 | 4.0 |
| T42 | 8 | 6.2 | 2.8 |

Wounds treated with full-length NELL1 did not show significant differences or trend towards better healing at day 42. Interestingly, wounds treated with full-length NELL1 showed significant differences in having a smaller inner unhealed area with Dose 2 at 3 days post-treatment (p=0.03) Because wound healing is not a linear process and previous reports suggested plotting log-transformed values, data was converted into log values and plotted (Gelfand et al. (2002) *The Society for Investigative Dermatology* 119:1420-1425). These log values were then used for graphical representation of the data (FIG. 6). Consistent with the initial analyses, the graphs for wounds treated with the smaller variant showed a trend for better healing from the controls and at after day 14, these wounds start to heal faster than the other treatment groups.

In addition to the standard T-test, additional statistical tools and approaches were used to analyze the data. A mixed-model ANOVA was used to analyze the data to factor in fixed and random effects and the study design where a single horse was given several different treatments (2 NELL1 protein forms and 2 doses per form).

When treatments were analyzed individually, there are significant differences by the mean rate of healing through time and these time patterns differ by treatment. This was also observed for the other parameters such as rate of contraction, rate of epithelialization, and overall healing rate. The mixed model ANOVA analyses confirmed the earlier results where treatment with NELL1 variant showed faster healing (smaller unhealed inner area) compared to control.

SUMMARY AND CONCLUSIONS

NELL1 horse proteins did not elicit any adverse effects on the wounds, over-all health and behavior of the horses. Horse NELL1 protein is deemed to be a safe product in the manner delivered and dosages tested in this study. This is the first known application of the horse NELL1 protein into an animal model.

NELL1 protein can be effectively and efficiently delivered into horse body wounds via a calcium alginate biodegradable dressing. The dressing enables delivery into the soft tissue injury within three days, wherein the entire dressing was completely absorbed into the wounds (by visual/macroscopic examination). This study represents the first known test in vivo of a calcium alginate dressing to administer NELL1 protein into soft tissue injuries.

NELL1 variant protein exhibited effects that promoted wound healing as measured by the remaining inner unhealed area assessed at day 42 post-treatment. The standard deviation for treatment at both doses was very low compared to either control or full-length NELL. There was no statistically significant difference between the two tested doses.

There were no statistically significant effects nor strong trends for control wounds or those treated with full-length NELL1 (except for day 3 post-treatment for NFL Dose 2, p=0.03) and the variations were large for both of these groups compared to the NELL1 variant form.

The mixed model analysis indicated that the pattern of healing over time was significantly different between the various treatment groups. The log graphs of inner unhealed area size for the different groups showed that the NELL1 variant treated wounds started differentiation or separation from the other treatments after day 14. These data suggested that perhaps a re-application of the NELL1 protein (before the end of 14 days) might sustain the effects beyond the initial weeks and 5 yield more dramatic effects than initially observed in this study.

Those skilled in the art will further appreciate that the present invention may be embodied in other specific forms without departing from the spirit or central attributes thereof. In that the foregoing description of the present invention discloses exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. A complementary DNA (cDNA) encoding a NELL1 peptide fragment or variant thereof, having at least 95% sequence identity to SEQ ID NO: 17 or 18, wherein said NELL1 peptide fragment or variant thereof has at least one of the properties selected from the group consisting of:
   a) enhanced efficacy in tissue regeneration,
   b) enhanced promotion of wound healing,
   c) easier purification,
   d) higher yield, and
   e) less aggregate formation,
when compared to the fragment's respective full-length NELL1 protein; and wherein said NELL1 peptide fragment or variant thereof lacks the carboxy-terminal 179 amino acid residues of the fragment's respective full-length NELL1 protein.

2. The cDNA of claim 1, wherein said NELL1 peptide fragment comprises the amino acid sequence set forth in SEQ ID NO: 17 or 18.

3. The cDNA of claim 1, wherein said NELL1 peptide fragment consists of the amino acid sequence set forth in SEQ ID NO: 17 or 18.

4. The cDNA of claim 1, wherein said NELL1 peptide fragment or variant thereof exhibits enhanced promotion of wound healing when compared to the fragment's respective full-length NELL1 protein.

5. A pharmaceutical composition comprising the cDNA of claim 1.

6. The pharmaceutical composition of claim 5, wherein said cDNA is incorporated into liposomes or nanoparticles.

7. A complementary DNA (cDNA) encoding a NELL1 peptide fragment or variant thereof having at least 99% sequence identity to SEQ ID NO: 17 or 18, wherein said NELL1 peptide fragment or variant thereof exhibits enhanced promotion of wound healing when compared to the fragment's respective full-length NELL1 protein.

8. The cDNA of claim 7, wherein said NELL1 peptide fragment comprises the amino acid sequence set forth in SEQ ID NO: 17 or 18.

9. The cDNA of claim 7, wherein said NELL1 peptide fragment consists of the amino acid sequence set forth in SEQ ID NO: 17 or 18.

10. A pharmaceutical composition comprising the cDNA of claim 7.

11. The pharmaceutical composition of claim 10, wherein said cDNA is incorporated into liposomes or nanoparticles.

12. A host cell comprising a heterologous nucleic acid sequence encoding a NELL1 peptide fragment or variant thereof, having at least 95% sequence identity to SEQ ID NO: 17 or 18, wherein said NELL1 peptide fragment or variant thereof has at least one of the properties selected from the group consisting of:
   a) enhanced efficacy in tissue regeneration,
   b) enhanced promotion of wound healing,
   c) easier purification,
   d) higher yield, and
   e) less aggregate formation,
when compared to the fragment's respective full-length NELL1 protein; and wherein said NELL1 peptide fragment or variant thereof lacks the carboxy-terminal 179 amino acid residues of the fragment's respective full-length NELL1 protein.

13. The host cell of claim 12, wherein said NELL1 peptide fragment comprises the amino acid sequence set forth in SEQ ID NO: 17 or 18.

14. The host cell of claim 12, wherein said NELL1 peptide fragment consists of the amino acid sequence set forth in SEQ ID NO: 17 or 18.

15. The host cell of claim 12, wherein said heterologous nucleic acid sequence is a complementary DNA (cDNA).

16. The host cell of claim 12, wherein said NELL1 peptide fragment or variant thereof exhibits enhanced promotion of wound healing when compared to the fragment's respective full-length NELL1 protein.

17. A pharmaceutical composition comprising the host cell of claim 12.

18. The pharmaceutical composition of claim 17, wherein said host cell is incorporated into a matrix.

19. A host cell comprising a heterologous nucleic acid sequence encoding a NELL1 peptide fragment or variant thereof having at least 99% sequence identity to SEQ ID NO: 17 or 18, wherein said NELL1 peptide fragment or variant thereof exhibits enhanced promotion of wound healing when compared to the fragment's respective full-length NELL1 protein.

20. The host cell of claim 19, wherein said NELL1 peptide fragment comprises the amino acid sequence set forth in SEQ ID NO: 17 or 18.

21. The host cell of claim 19, wherein said NELL1 peptide fragment consists of the amino acid sequence set forth in SEQ ID NO: 17 or 18.

22. The host cell of claim 19, wherein said heterologous nucleic acid sequence is a complementary DNA (cDNA).

23. A pharmaceutical composition comprising the host cell of claim 19.

24. The pharmaceutical composition of claim 23, wherein said host cell is incorporated into a matrix.

\* \* \* \* \*